United States Patent
Aukerman et al.

(10) Patent No.: US 8,337,851 B2
(45) Date of Patent: Dec. 25, 2012

(54) METHODS OF MONITORING THE EFFICACY OF ANTI-CD40 ANTIBODIES IN TREATING A SUBJECT FOR A CD40-EXPRESSING CANCER

(75) Inventors: Sharon Lea Aukerman, Mosaga, CA (US); Bahija Jallal, Emeryville, CA (US); Mohammad Luqman, Danville, CA (US)

(73) Assignees: Novartis AG, Basel (CH); Xoma Technology Ltd., Berkeley, CA (US)

( * ) Notice: Subject to any disclaimer, the term of this patent is extended or adjusted under 35 U.S.C. 154(b) by 1036 days.

(21) Appl. No.: 11/914,714

(22) PCT Filed: May 18, 2006

(86) PCT No.: PCT/US2006/019414
§ 371 (c)(1), (2), (4) Date: Jul. 11, 2008

(87) PCT Pub. No.: WO2006/125413
PCT Pub. Date: Nov. 23, 2006

(65) Prior Publication Data
US 2009/0041773 A1    Feb. 12, 2009

Related U.S. Application Data

(60) Provisional application No. 60/682,582, filed on May 18, 2005, provisional application No. 60/749,285, filed on Dec. 9, 2005.

(51) Int. Cl.
*A61K 39/395* (2006.01)
*C12Q 1/00* (2006.01)
*C12Q 1/68* (2006.01)
*G01N 33/53* (2006.01)

(52) U.S. Cl. ............... 424/144.1; 424/143.1; 424/153.1; 424/155.1; 424/173.1; 424/174.1; 435/4; 435/6.1; 435/7.1; 435/7.2

(58) Field of Classification Search .................. None
See application file for complete search history.

(56) References Cited

U.S. PATENT DOCUMENTS

| 6,444,233 | B1 * | 9/2002 | Arntzen et al. | 424/725 |
| 7,288,252 | B2 * | 10/2007 | Chu et al. | 424/153.1 |
| 2002/0009444 | A1 | 1/2002 | Grillo-Lopez | |
| 2003/0211100 | A1 | 11/2003 | Bedian et al. | |
| 2004/0219616 | A1 * | 11/2004 | Seery et al. | 435/7.23 |
| 2007/0098718 | A1 * | 5/2007 | Long et al. | 424/144.1 |
| 2007/0254850 | A1 * | 11/2007 | Lieberman et al. | 514/44 |
| 2007/0292439 | A1 * | 12/2007 | Luqman | 424/172.1 |
| 2008/0254026 | A1 * | 10/2008 | Long et al. | 424/133.1 |
| 2009/0215895 | A1 * | 8/2009 | Ferrante et al. | 514/560 |

FOREIGN PATENT DOCUMENTS

| WO | WO 01/80884 A1 | 11/2001 |
| WO | WO 03/040170 A2 | 5/2003 |
| WO | WO 2004/053497 A2 | 6/2004 |
| WO | WO 2005/044306 | * 5/2005 |
| WO | WO 2005/044854 | * 5/2005 |

OTHER PUBLICATIONS

Biomarkers Definitions Working Groups., Clin. Pharmacol. Ther. 69: 89-95, 2001.*
Alexandroff et al., Molecular Immunology 37: 515-526, 2000.*
Wang et al., British Journal of Haematology 97: 409-417, 1997.*
Cherukuri et al., Blood 106, 11, Part 1: p. 832A, Abstract 2965, Nov. 16, 2005.*
Hase, H., et al., "Roles of Co-stimulatory Molecules: Mechanism of Anti-apoptotic Effect of B Cell Apoptosis by CD27 and CD40 Signaling," *Clin. Immunol.*, 2003, vol. 4, No. 5, pp. 487-493.
Yasui, T., et al., "Signal transduction and gene—CD40 Signal," *Genetic Medicine*, 1999, vol. 3, No. 2, pp. 64-69.

* cited by examiner

*Primary Examiner* — Phillip Gambel
(74) *Attorney, Agent, or Firm* — Alston & Bird LLP

(57) ABSTRACT

Methods for identifying subjects having a cancer or pre-malignant condition that will benefit from anti-CD40 therapeutic agents that modulate CD40L-mediated CD40 signaling are provided. The methods comprise the use of biomarkers of cellular apoptosis, cell proliferation and survival, and CD40 signaling pathways to monitor ex vivo response to one or more anti-CD40 therapeutic agents of interest that modulate CD40 signaling on CD40-expressing neoplastic cells. The ex vivo prognostic assays can be used alone or in conjunction with other prognostic assays to identify candidate subjects who will benefit from treatment with anti-CD40 therapeutic agents. Methods of the invention also comprise the use of these biomarkers to monitor in vivo efficacy of treatment with an anti-CD40 therapeutic agent.

62 Claims, 27 Drawing Sheets

METHODS OF MONITORING THE EFFICACY OF ANTI-CD40 ANTIBODIES IN TREATING A SUBJECT FOR A CD40-EXPRESSING CANCER

CROSS-REFERENCE TO RELATED APPLICATIONS

This application is a national stage of International Patent Application No. PCT/US2006/019414, filed May 18, 2006, which claims the benefit of U.S. Provisional Application No. 60/682,582, filed May 18, 2005, and U.S. Provisional Application No. 60/749,285, filed Dec. 9, 2005.

FIELD OF THE INVENTION

The invention relates to the field of diagnostic and prognostic medicine, more particularly to methods for determining efficacy of therapeutic agents in treatment of proliferative disorders, including cancers and pre-malignant conditions, associated with aberrant CD40 signaling.

BACKGROUND OF THE INVENTION

Many members of the tumor necrosis factor (TNF) family of ligands and their corresponding receptors regulate growth of normal cells by inducing apoptosis or enhancing cell survival and proliferation. It is this balance between apoptotic signals and survival and proliferation signals that maintains normal cellular homeostasis. At least 26 TNF family receptors and 18 TNF family ligands have been identified to date. The biologically active forms of both the receptors and ligands are self-assembled protein trimers. Transmembrane and soluble forms of both the receptors and ligands have been identified. Though the intracellular domains of the receptors share no sequence homology, their extracellular domains comprise 40-amino-acid, cysteine-rich repeats. Their cytoplasmic tails signal by interacting with two major groups of intracellular proteins: TNF receptor-associated factors (TRAFs) and death domain (DD)-containing proteins. Interaction between at least six human TRAFs and TRAF-binding sites on the cytoplasmic tail of some of these receptors initiates several signaling pathways, including AKT (the serine/threonine kinase referred to as protein kinase B or PKB), nuclear factor-κb (NF-κB), and mitogen-activated protein kinases (MAPK). See, for example, the review by Younes and Kadin (2003) *J. Clin. Oncol.* 18:3526-3534.

The TNF family receptor member CD40 is a 50-55 kDa cell-surface antigen present on the surface of both normal and neoplastic human B cells, dendritic cells, monocytes, macrophages, $CD8^+$ T cells, endothelial cells, monocytic and epithelial cells, some epithelial carcinomas, and many solid tumors, including lung, breast, ovary, urinary bladder, and colon cancers. Binding of the CD40 ligand to the CD40 antigen on the B cell membrane provides a positive costimulatory signal that stimulates B cell activation and proliferation, resulting in B cell maturation into a plasma cell that secretes high levels of soluble immunoglobulin. CD40 activates TRAF-1, TRAF-2, -3, -5, and -6, which upregulate diverse signaling pathways following engagement of CD40 with CD40L (either membrane-bound CD40L or soluble CD40L), including extracellular signal-regulated kinase (ERK), c-jun amino terminal kinase (JNK), p38 mitogen-activated protein kinase (MAPK), AKT, and NF-κB (see, for example, Younes and Carbone (1999) *Int. J. Biol. Markers* 14:135-143; van Kooten and Banchereau (2000) *J. Leukoc. Biol.* 67:2-17).

Malignant B cells from tumor types of B-cell lineage express CD40 and appear to depend on CD40 signaling for survival and proliferation. Transformed cells from patients with low- and high-grade B-cell lymphomas, B-cell acute lymphoblastic leukemia, multiple myeloma, chronic lymphocytic leukemia, Walsdenstrom's Macroglobulinemia, and Hodgkin's disease express CD40. CD40 expression is also detected in two-thirds of acute myeloblastic leukemia cases and 50% of AIDS-related lymphomas.

A number of carcinomas and sarcomas also exhibit high levels of CD40 expression, though the role of CD40 signaling in relation to CD40 expression on these cancer cells is less well understood. CD40-expressing carcinomas include urinary bladder carcinoma (Paulie et al. (1989) *J. Immunol.* 142:590-595; Braesch-Andersen et al. (1989) *J. Immunol.* 142:562-567), breast carcinoma (Hirano et al. (1999) *Blood* 93:2999-3007; Wingett et al. (1998) *Breast Cancer Res. Treat.* 50:27-36); prostate cancer (Rokhlin et al. (1997) *Cancer Res.* 57:1758-1768), renal cell carcinoma (Kluth et al. (1997) *Cancer Res.* 57:891-899), undifferentiated nasopharyngeal carcinoma (UNPC) (Agathanggelou et al. (1995) *Am. J. Pathol.* 147:1152-1160), squamous cell carcinoma (SCC) (Amo et al. (2000) *Eur. J. Dermatol.* 10:438-442; Posner et al. (1999) *Clin. Cancer Res.* 5:2261-2270), thyroid papillary carcinoma (Smith et al. (1999) *Thyroid* 9:749-755), cutaneous malignant melanoma (van den Oord et al. (1996) *Am. J. Pathol.* 149:1953-1961), gastric carcinoma (Yamaguchi et al. (2003) *Int. J. Oncol.* 23(6):1697-702), and liver carcinoma (see, for example, Sugimoto et al. (1999) *Hepatology* 30(4): 920-26, discussing human hepatocellular carcinoma). For CD40-expressing sarcomas, see, for example, Lollini et al. (1998) *Clin. Cancer Res.* 4(8):1843-849, discussing human osteosarcoma and Ewing's sarcoma.

CD40 signaling protects immature B-cells and B-cell lymphomas from apoptosis induced by IgM or Fas (see, for example, Wang et al. (1995) *J. Immunol.* 155:3722-3725). Mantel cell lymphoma cells express a high level of CD40, and the addition of exogenous CD40 ligand was shown to enhance their survival and rescue them from fludarabin-induced apoptosis (Clodi et al. (1998) *Brit. J. Haematol.* 103: 217-219).

The role of CD40 signaling in malignant B cell survival and proliferation renders the CD40 antigen a potential target for anti-cancer therapy. Indeed, antagonist anti-CD40 antibodies inhibit proliferation and/or differentiation of malignant human B cells in vitro (see, for example, U.S. Patent Application Publication No. 20040109857). Further, murine models of aggressive human lymphomas have demonstrated the in vivo efficacy of anti-CD40 antibodies in promoting animal survival. See, for example, Funakoshi et al. (1994) *Blood* 83:2787-2794; Tutt et al. (1998) *J. Immunol.* 161:3176-3185; and Szocinski et al. (2002) *Blood* 100: 217-223.

The CD40 ligand (CD40L), also known as CD154, is a 32-33 kDa transmembrane protein that also exists in two smaller biologically active soluble forms, 18 kDa and 31 kDa, respectively (Graf et al. (1995) *Eur. J. Immunol.* 25:1749-1754; Mazzei et al. (1995) *J. Biol. Chem.* 270:7025-7028; Pietravalle et al. (1996) *J. Biol. Chem.* 271:5965-5967). CD40L is expressed on activated, but not resting, $CD4^+$ T-helper cells (Lane et al. (1992) *Eur. J. Immunol.* 22:2573-2578; Spriggs et al. (1992) *J. Exp. Med.* 176:1543-1550; and Roy et al. (1993) *J. Immunol.* 151:1-14). Both CD40 and CD40L have been cloned and characterized (Stamenkovi et al. (1989) *EMBO J.* 8:1403-1410; Armitage et al. (1992) *Nature* 357:80-82; Lederman et al. (1992) *J. Exp. Med.* 175: 1091-1101; and Hollenbaugh et al. (1992) *EMBO J.* 11:4313-4321). See also U.S. Pat. No. 5,945,513, describing human CD40L. Cells transfected with the CD40L gene and expressing the CD40L protein on their surface can trigger B-cell proliferation, and together with other stimulatory signals, can induce antibody production (Armitage et al. (1992) supra; and U.S. Pat. No. 5,945,513). Patients with lymphoid malignancies, autoimmune disease, cardiovascular disease, and essential thrombocythemia have elevated serum levels of soluble CD40L (sCD40L) that are not seen in healthy subjects. Constitutive expression of CD40L has been observed in a subset of patients with several B-cell lymphoid malignancies, including mantle-cell lymphoma, follicular lymphoma, marginal zone lymphoma, chronic lymphocytic leukemia (CLL), diffuse large B-cell lymphoma (DLBCL), follicular lymphoma (FL), and HIV-infected B-cell lymphoma. See, for example, Clodi et al. (1998) *Br. J. Haematol.* 103:270-275; Schattner et al. (1998) *Blood* 91:2689-2697; Moses et al. (1997) *Nat. Med.* 3:1242-1249; Trentin et al. (1997) *Cancer Res.* 57:4940-4947; and Pham et al. (2002) *Immunity* 16:37-50). CD40L may play an important role in the cell contact-dependent interaction of CD40-expressing tumor B-cells within the neoplastic follicles or CD40-expressing Reed-Sternberg cells in Hodgkin's disease areas (Carbone et al. (1995) *Am. J. Pathol.* 147:912-922). However, the mechanism of CD40L-mediated CD40 signaling leading to survival versus cell death responses of malignant B-cells is not completely known. For example, in follicular lymphoma cells, down-regulation of apoptosis-inducing TRAIL molecule (APO-2L) (Ribeiro et al. (1998) *British J. Haematol.* 103: 684-689) and overexpression of Bcl-2, and in the case of B-CLL, down-regulation of CD95 (Fas/APO-1) (Laytragoon-Lewin et al. (1998) *Eur. J. Haematol.* 61:266-271) have been proposed as mechanisms of survival. In contrast, evidence in follicular lymphoma indicates that CD40 activation leads to up-regulation of TNF (Worm et al. (1994) *International Immunol.* 6:1883-1890) and CD95 molecules (Plumas et al. (1998) *Blood* 91:2875-2885).

Given the important role of CD40 signaling in survival and proliferation of neoplastic cells, methods for identifying individuals who would be responsive to treatment regimens that target CD40-expressing tumors and more specifically CD40 signaling are needed.

BRIEF SUMMARY OF THE INVENTION

Methods for identifying subjects having a cancer or pre-malignant condition that will benefit from anti-CD40 therapeutic agents including those that modulate CD40L-mediated signaling and/or modulate antibody-dependent cellular cytotoxicity (ADCC) are provided. Such anti-CD40 therapeutic agents include, but are not limited to, antagonist anti-CD40 antibodies, antagonist anti-CD40L antibodies, and pharmacologic agents that block or interfere with CD40/CD40L interaction, particularly CD40L-mediated CD40 signaling, as well as antagonist anti-CD40 antibodies that additionally, or alternatively, have ADCC activity as a mode of action. In some embodiments, the methods comprise the use of biomarkers of cellular apoptosis, cell proliferation and survival, and CD40 signaling pathways to monitor ex vivo cellular response to one or more anti-CD40 therapeutic agents of interest. These ex vivo prognostic assays comprise providing a test biological sample and a control biological sample from a candidate subject, where these biological samples comprise CD40-expressing neoplastic cells that have been stimulated with a CD40 ligand, either in vivo or ex vivo; contacting the test biological sample with the anti-CD40 therapeutic agent of interest; detecting the expression level of at least one biomarker within the test biological sample; and comparing the expression level of the biomarker(s) with the corresponding expression level detected in the control biological sample, which has not been contacted with the anti-CD40 therapeutic agent of interest. Biomarkers for use in these ex vivo prognostic assays include proteins and/or genes whose expression levels are prognostic indicators of responsiveness to treatment intervention, including biomarkers of cellular apoptosis, biomarkers of CD40L-mediated CD40 signaling pathways, and biomarkers of cell proliferation or survival, depending upon the mode of action of the anti-CD40 therapeutic agent. Where the anti-CD40 therapeutic agent has its mode of action via disruption of CD40L-mediated CD40 signaling, biomarkers of cellular apoptosis, CD40L-mediated CD40 signaling pathways, and cell proliferation or survival can be used in these ex vivo prognostic assays. In some embodiments, additional markers of CD40L-mediated CD40 signaling can be assayed, including, but not limited to, cytokines that are upregulated via CD40L-CD40 interaction, for example, vascular endothelial growth factor (VEGF), interleukin (IL)-6, IL-8, IL-10, granulocyte monocyte colony-stimulating factor (GM-CSF), tumor necrosis factor-α (TNF-α), monocyte chemoattractant protein-1 (MCP-1), and macrophage inflammatory protein-1 (MIP-1β). Where the anti-CD40 therapeutic agent has its mode of action via ADCC, for example, an anti-CD40 antibody, biomarkers of cellular apoptosis can be used in these ex vivo prognostic assays.

In other embodiments of the invention, candidate subjects are screened for the expression level of one or more CD40-related factors that are predictive of an individual, or a subpopulation of individuals, who will benefit from intervention with anti-CD40 therapeutic agents. Thus, in one embodiment, biological samples collected from candidate subjects, for example, subjects having a cancer or pre-malignant condition of B-cell lineage, are screened for one or more CD40-related factors selected from the group consisting of expression level of cell-surface CD40 antigen on neoplastic cells, expression level of cell-surface CD40L on neoplastic cells, circulating level of soluble CD40 (sCD40), and circulating level of soluble CD40L (sCD40L). These CD40-related factors can be prognostic indicators of the disease, and can further be used to identify subjects who would or would not respond to therapeutic intervention with anti-CD40 therapeutic agents, regardless of the mode of action of the anti-CD40 therapeutic agent. An elevated level of expression of one or more of these CD40-related factors within a biological sample when compared to a control or reference standard would be indicative of an individual who would benefit from therapeutic intervention with an anti-CD40 therapeutic agent that modulates CD40L-mediated CD40 signaling, modulates ADCC, or both. Candidate subjects identified with this screening process can be treated with an anti-CD40 therapeutic agent of interest, or can be further screened for responsiveness to anti-CD40 therapeutic agents using the ex vivo prognostic assays described herein.

In yet other embodiments, candidate subjects are screened for the presence or absence of one or more clinically useful prognostic markers in order to define subpopulations of candidate subjects who have a poor prognosis with other classes of cancer therapeutics but who will benefit from intervention with anti-CD40 therapeutic agents. In this manner, biological samples collected from candidate subjects are screened for one or more clinically useful prognostic markers known to be indicators of poor prognosis with current therapeutics whose mode of action is not via CD40 targeting or CD40L-mediated CD40 signaling. Any clinically useful prognostic marker for a given cancer or pre-malignant condition can be included in the screening process. In some embodiments, the subpopulation of candidate subjects represents patients with chronic lymphocytic leukemia (CLL) for whom current therapies of treatment are not curative, and the clinically useful prognostic markers included in the screening process are selected from the group consisting of ZAP-70, CD38, β2 microglobulin, and cytogenetic markers, for example, p53 mutational status, ATM mutational status, and chromosome deletions, such as the chromosome 17p deletion and the chromosome 11q deletion. Candidate subjects within a subpopulation identified with this screening process can be further screened for responsiveness to anti-CD40 therapeutic agents using the ex vivo prognostic assays described herein.

The present invention also provides methods for monitoring efficacy of an anti-CD40 therapeutic agent in treatment of a subject having a cancer comprising CD40-expressing neoplastic cells, and in treatment of a subject having a pre-malignant condition at risk of developing into a malignancy associated with aberrant CD40 expression and/or signaling. In this manner, a subject undergoing therapy with an anti-CD40 therapeutic agent, who may or may not have been previously screened using an ex vivo prognostic assay disclosed herein, is monitored for in vivo changes in the expression of at least one biomarker of cellular apoptosis, cell proliferation and survival, and/or one or more CD40L-mediated CD40 signaling pathways following treatment with the anti-CD40 therapeutic agent. The particular biomarkers to be assayed can be chosen based on mode of action of the therapeutic agent as noted above. Alternatively, or additionally, the subject can be monitored for in vivo changes in the expression level of one or more CD40-related factors selected from the group consisting of cell-surface CD40 antigen on neoplastic cells, cell-surface CD40L on neoplastic cells, circulating level of sCD40, and circulating level of sCD40L following treatment with the anti-CD40 therapeutic agent. In this manner, a first biological sample is obtained from the subject and assayed for the expression level of one or more of these biomarkers and/or CD40-related factors to obtain a baseline level of expression for each factor assayed, and then one or more subsequent biological samples is obtained from the subject and assayed for the same biomarker(s) and/or CD40-related factor(s), where the subsequent biological sample is obtained following the administration of at least one dose of the anti-CD40 therapeutic agent of interest. Monitoring can occur at a single point in time, or at multiple points in time, to ascertain efficacy of any given treatment protocol wherein the anti-CD40 therapeutic agent is administered to the subject. Depending upon the biomarker being assayed, a decrease or increase in the expression level of the biomarker between any two time points can be indicative of efficacy of the anti-CD40 therapeutic agent in treatment of the cancer or pre-malignant condition. Where monitoring reveals a decrease in the expression level of one or more of the CD40-related factors, such a result can be indicative of efficacy of the anti-CD40 therapeutic agent in treatment of the cancer or pre-malignant condition.

Expression level of these various biomarkers and CD40-related factors, and any clinically useful prognostic markers in a biological sample can be detected at the protein or nucleic acid level, using, for example, immunohistochemistry techniques or nucleic acid-based techniques such as in situ hybridization and RT-PCR. In some embodiments, an elevated level or an increase in expression of at least one biomarker is indicative of a positive therapeutic response to treatment with an anti-CD40 therapeutic agent. In other embodiments, a diminished level or a decrease in expression of at least one biomarker is indicative of a positive therapeutic response to treatment with the anti-CD40 therapeutic agent.

DETAILED DESCRIPTION OF THE INVENTION

Figure 1:
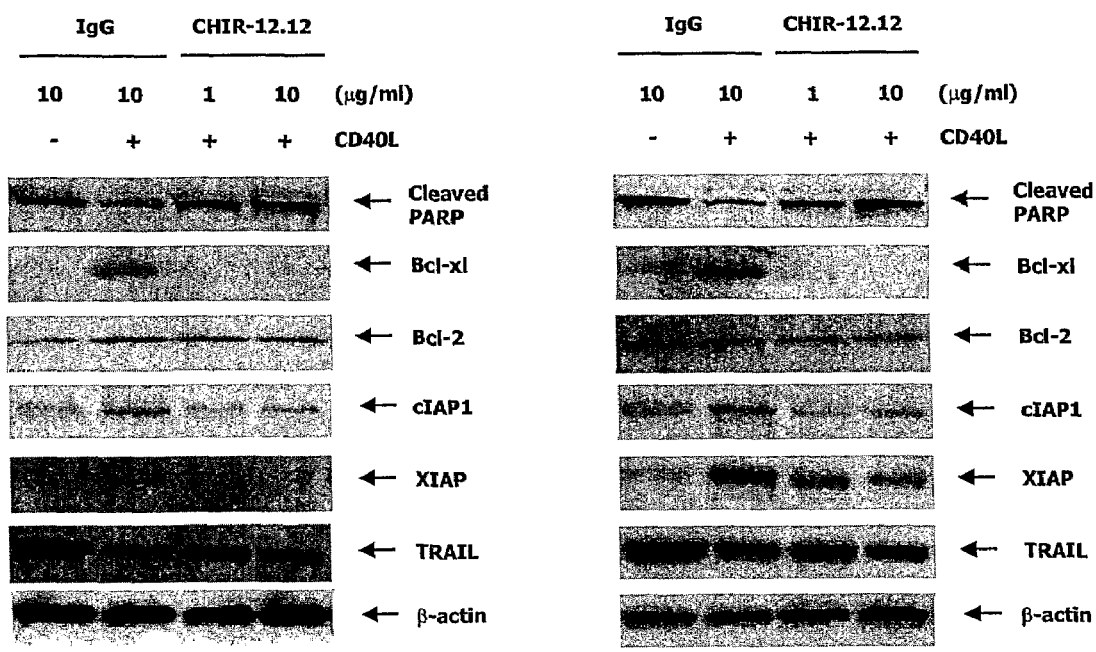
FIG. 1 shows inhibition of CD40 ligand (CD40L)-mediated survival by CHIR-12.12 in B-CLL cells obtained from B-CLL patients.

The present invention is directed to methods for identifying subjects having a cancer or pre-malignant condition that would benefit from treatment with anti-CD40 therapeutic agents that target the CD40 receptor and which modulate ADCC, interfere with CD40 signaling, particularly CD40 signaling pathways that are mediated by interaction of CD40 with the CD40 ligand (CD40L), or both. In one embodiment, the methods comprise the use of ex vivo prognostic assays to monitor the effects of antagonist anti-CD40 therapeutic agents that block or interfere with CD40L-mediated CD40 signaling on the expression level of three classes of biomarkers that are associated with CD40L-mediated CD40 signaling, particularly biomarkers of cell proliferation or survival and cell apoptotic pathways and biomarkers of key CD40L-mediated CD40 signaling pathways, including the AKT, NF-κB, and mitogen-activated protein kinase (MAPK) signaling pathways. Additional markers that can serve to monitor effects of antagonist anti-CD40 therapeutic agents that block or interfere with CD40L-mediated CD40 signaling include cytokines that are upregulated via CD40L-mediated CD40 signaling, as noted herein below. Biomarkers for cell apoptotic pathways can also serve to monitor effects of anti-CD40 therapeutic agents that modulate ADCC, for example, anti-CD40 antibodies having ADCC as a mode of action. Therapeutic agents that act as antagonists of CD40 signaling, referred to herein as "CD40 antagonists," can interfere with one or more of the signaling cues normally triggered by binding of CD40L to the CD40 receptor. The ex vivo prognostic assays of the present invention can be used to discriminate between subjects who would benefit from intervention with CD40 antagonists and therapeutic agents that target CD40 and modulate ADCC and those for whom intervention with these types of therapeutic agents would not be beneficial. Candidate subjects can additionally, or alternatively, be screened for the presence or absence of, or elevated or diminished levels of, one or more CD40-related factors and/or one or more clinically useful prognostic markers to define individuals or subpopulations of candidate subjects who would benefit from therapeutic intervention with anti-CD40 therapeutic agents that modulate CD40L-mediated CD40 signaling and/or ADCC. Subjects identified in these screening methods can be further screened using the ex vivo prognostic assays described herein. The biomarkers and CD40-related factors described herein also find use in monitoring efficacy of treatment with anti-CD40 therapeutic agents that modulate CD40 signaling and/or ADCC, and in determining the basis for drug responsiveness in individual cancer patients or subpopulations of cancer patients.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include, but are not limited to, lymphoma and leukemia, and solid tumors. By "B cell-related cancer" or "cancer of B-cell lineage" is intended any type of cancer in which the dysregulated or unregulated cell growth is associated with B cells.

By "refractory" in the context of a cancer is intended the particular cancer is resistant to, or non-responsive to, therapy with a particular therapeutic agent. A cancer can be refractory to therapy with a particular therapeutic agent either from the onset of treatment with the particular therapeutic agent (i.e., non-responsive to initial exposure to the therapeutic agent), or as a result of developing resistance to the therapeutic agent, either over the course of a first treatment period with the therapeutic agent or during a subsequent treatment period with the therapeutic agent.

By "CD40 antigen," "CD40 cell surface antigen," "CD40 receptor," or "CD40" is intended a transmembrane glycoprotein that belongs to the tumor necrosis factor (TNF) receptor family (see, for example, U.S. Pat. Nos. 5,674,492 and 4,708,871; Stamenkovic et al. (1989) *EMBO* 8:1403; Clark (1990) *Tissue Antigens* 36:33; Barclay et al. (1997) *The Leucocyte Antigen Facts Book* (2d ed.; Academic Press, San Diego)). Two isoforms of human CD40, encoded by alternatively spliced transcript variants of this gene, have been identified. The first isoform (also known as the "long isoforms" or "isoform 1") is expressed as a 277-amino-acid precursor polypeptide (SEQ ID NO:12 (first reported as GenBank Accession No. CAA43045, and identified as isoform 1 in GenBank Accession No. NP_001241), encoded by SEQ ID NO:11 (see GenBank Accession Nos. X60592 and NM_001250)), which has a signal sequence represented by the first 19 residues. The second isoform (also known as the "short isoforms" or "isoform 2") is expressed as a 203-amino-acid precursor polypeptide (SEQ ID NO:10 (GenBank Accession No. NP_690593), encoded by SEQ ID NO:9 (GenBank Accession No. NM_152854)), which also has a signal sequence represented by the first 19 residues. The precursor polypeptides of these two isoforms of human CD40 share in common their first 165 residues (i.e., residues 1-165 of SEQ ID NO:10 and SEQ ID NO:12). The precursor polypeptide of the short isoform (shown in SEQ ID NO:10) is encoded by a transcript variant (SEQ ID NO:9) that lacks a coding segment, which leads to a translation frame shift; the resulting CD40 isoform contains a shorter and distinct C-terminus (residues 166-203 of SEQ ID NO:10) from that contained in the long isoform of CD40 (C-terminus shown in residues 166-277 of SEQ ID NO:12). For purposes of the present invention, the term "CD40 antigen," "CD40 cell surface antigen," "CD40 receptor," or "CD40" encompasses both the short and long isoforms of CD40.

The CD40 antigen is displayed on the surface of a variety of cell types, as described elsewhere herein. By "displayed on the surface" and "expressed on the surface" is intended that all or a portion of the CD40 antigen is exposed to the exterior of the cell. The displayed or expressed CD40 antigen may be fully or partially glycosylated.

By "agonist activity" is intended that a substance functions as an agonist. An agonist combines with a receptor on a cell and initiates a reaction or activity that is similar to or the same as that initiated by the receptor's natural ligand. An agonist of CD40 induces any or all of, but not limited to, the following responses: B cell proliferation and differentiation, antibody production, intercellular adhesion, B cell memory generation, isotype switching, up-regulation of cell-surface expression of MHC Class II and CD80/86, and secretion of pro-inflammatory cytokines such as VEGF, IL-8, IL-12, and TNF. By "antagonist activity" is intended that the substance functions as an antagonist. An antagonist of CD40 prevents or reduces induction of any of the responses induced by binding of the CD40 receptor to an agonist ligand, particularly CD40L. The antagonist may reduce induction of any one or more of the responses to agonist binding by 5%, 10%, 15%, 20%, 25%, 30%, 35%, preferably 40%, 45%, 50%, 55%, 60%, more preferably 70%, 80%, 85%, and most preferably 90%, 95%, 99%, or 100%. Methods for measuring CD40 ligand binding specificity and antagonist activity of an anti-CD40 therapeutic agent, for example, an anti-CD40 antibody, are known in the art and include, but are not limited to, standard competitive binding assays, assays for monitoring immunoglobulin secretion by B cells, B cell proliferation assays, Banchereau-Like-B cell proliferation assays, T cell helper assays for antibody production, co-stimulation of B cell proliferation assays, and assays for up-regulation of B cell activation markers. See, for example, such assays disclosed in WO 00/75348 and U.S. Pat. No. 6,087,329, herein incorporated by reference. Also see, provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety.

By "significant" agonist activity is intended an agonist activity of at least 30%, 35%, 40%, 45%, 50%, 60%, 70%, 75%, 80%, 85%, 90%, 95%, or 100% greater than the agonist activity induced by a neutral substance or negative control as measured in an assay of a B cell response. Preferably, "significant" agonist activity is an agonist activity that is at least 2-fold greater or at least 3-fold greater than the agonist activity induced by a neutral substance or negative control as measured in an assay of a B cell response. Thus, for example, where the B cell response of interest is B cell proliferation, "significant" agonist activity would be induction of a level of B cell proliferation that is at least 2-fold greater or at least 3-fold greater than the level of B cell proliferation induced by a neutral substance or negative control. In one embodiment, a non-specific immunoglobulin, for example IgG1, that does not bind to CD40 serves as the negative control. A substance "free of significant agonist activity" would exhibit an agonist activity of not more than about 25% greater than the agonist activity induced by a neutral substance or negative control, preferably not more than about 20% greater, 15% greater, 10% greater, 5% greater, 1% greater, 0.5% greater, or even not more than about 0.1% greater than the agonist activity induced by a neutral substance or negative control as measured in an assay of a B cell response.

In some embodiments of the invention, the anti-CD40 therapeutic agent is an antagonist anti-CD40 antibody. Such antibodies are free of significant agonist activity as noted above when bound to a CD40 antigen on a human cell. In one embodiment of the invention, the antagonist anti-CD40 antibody is free of significant agonist activity in one cellular response. In another embodiment of the invention, the antagonist anti-CD40 antibody is free of significant agonist activity in assays of more than one cellular response (e.g., proliferation and differentiation, or proliferation, differentiation, and, for B cells, antibody production). In some embodiments of the invention, the anti-CD40 therapeutic agent of interest is an antagonist anti-CD40 antibody, for example, the fully human monoclonal antibody CHIR-12.12 or CHIR-5.9, or antigen-binding fragment thereof, as noted herein below.

Any of the assays known in the art can be used to determine whether an anti-CD40 therapeutic agent acts as an antagonist of one or more B cell responses. In some embodiments, the therapeutic agent is an anti-CD40 antibody that acts as an antagonist of at least one B cell response selected from the group consisting of B cell proliferation, B cell differentiation, antibody production, intercellular adhesion, B cell memory generation, isotype switching, up-regulation of cell-surface expression of MHC Class II and CD80/86, and secretion of pro-inflammatory cytokines such as VEGF, IL-8, IL-12, and TNF. Of particular interest are antagonist anti-CD40 antibodies that free of significant agonist activity with respect to B cell proliferation when bound to the human CD40 antigen on the surface of a human B cell.

In one such embodiment, the anti-CD40 antibody is an antagonist of B cell proliferation as measured in a B cell proliferation assay such as that described in Example 6 herein below, and the antagonist anti-CD40 antibody stimulates B cell proliferation at a level that is not more than about 25% greater than the B cell proliferation induced by a neutral substance or negative control, preferably not more than about 20% greater, 15% greater, 10% greater, 5% greater, 1% greater, 0.5% greater, or even not more than about 0.1% greater than the B cell proliferation induced by a neutral substance or negative control.

In other embodiments, the anti-CD40 antibody is an antagonist of B cell proliferation that is induced by another anti-CD40 antibody, for example, the S2C6 anti-CD40 antibody, as measured in a B cell proliferation assay such as that described in Example 6 herein below, and the level of B cell proliferation stimulated by the other anti-CD40 antibody in the presence of the antagonist anti-CD40 antibody is not more than about 25% of the B cell proliferation induced by the other anti-CD40 antibody in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by the other anti-CD40 antibody in the absence of the antagonist anti-CD40 antibody.

In yet other embodiments, the anti-CD40 antibody is an antagonist of B cell proliferation that is induced by the cell line EL4B5 as measured in the B cell activation assay described in Example 6 herein below, and the level of B cell proliferation stimulated by the EL4B5 cell line in the presence of the antagonist anti-CD40 antibody is not more than about 25% of the B cell proliferation induced by this cell line in the absence of the antagonist anti-CD40 antibody (i.e., at least 75% inhibition), preferably not more than about 20%, 15%, 10%, 5%, 1%, 0.5%, or even not more than about 0.1% of the B cell proliferation induced by this cell line in the absence of the antagonist anti-CD40 antibody.

In still other embodiments, the anti-CD40 antibody is an antagonist of human T-cell-induced antibody production by human B cells as measured in the human T-cell helper assay for antibody production by B cells described in Example 6 herein below. In this manner, the level of IgG antibody production, IgM antibody production, or both IgG and IgM antibody production by B cells stimulated by T cells in the presence of the antagonist anti-CD40 antibody is not more than about 50% of the respective antibody production by B cells stimulated by T cells in the absence of the antagonist anti-CD40 antibody (i.e., at least 75% inhibition), preferably not more than about 25%, 20%, 15%, 10%, 5%, 1%, 0.5%, or even not more than about 0.1% of the respective antibody production by B cells stimulated by T cells in the absence of the antagonist anti-CD40 antibody.

By "CD40 ligand" is intended any peptide, polypeptide, or protein that can bind to and activate one or more CD40 signaling pathways. Thus, "CD40 ligands" include, but are not limited to, full-length CD40 ligand proteins and variants and fragments thereof that retain sufficient activity to carry out the function of binding to and stimulating CD40 signaling on CD40-expressing cells. Modifications to a native CD40 ligand, for example, human CD40 ligand (CD40L; also known as CD154), include, but are not limited to, substitutions, deletions, truncations, extensions, fusion proteins, fragments, peptidomimetics, and the like. In some embodiments of the invention, the ex vivo prognostic assays include the use of soluble CD40L, for example, soluble recombinant human CD40L (Alexis Corporation, Bingham, Nottinghamshire, UK) to stimulate CD40 signaling on CD40-expressing neoplastic cells of a biological sample.

By "CD40L-mediated CD40 signaling" is intended any of the biological activities that result from interaction of the cell-surface receptor CD40 with a CD40 ligand. Examples of CD40 signaling are signals that lead to proliferation and survival of CD40-expressing cells, and stimulation of one or more CD40-signaling pathways within CD40-expressing cells. A CD40 "signaling pathway" or "signal transduction pathway" is intended to mean at least one biochemical reaction, or a group of biochemical reactions, that results from interaction of the CD40 receptor with a CD40 ligand, for example, CD40L, and which generates a signal that, when transmitted through the signal pathway, leads to activation of one or more downstream molecules in the signaling cascade. Signal transduction pathways involve a number of signal transduction molecules that lead to transmission of a signal from the cell-surface CD40 receptor across the plasma membrane of a cell, and through one or more in a series of signal transduction molecules, through the cytoplasm of the cell, and in some instances, into the cell's nucleus. Of particular interest to the present invention are CD40 signal transduction pathways, including the AKT signaling pathway, which leads to activation of AKT, and ultimately activation of NF-κB via the NF-κB signaling pathway; and mitogen-activated protein kinase (MAPK) signaling pathways, including the MEK/ERK signaling pathway and the MEK/p38 signaling pathway, which lead to activation of ERK and p38, respectively. The balance between activation and blocking of these signaling pathways favors either cell survival or apoptosis as noted herein below.

The methods of the present invention are directed to ex vivo prognostic assays, and prognostic assays that utilize antibodies, either in a detection step, or as candidate anti-CD40 therapeutic agents that are being tested in these ex vivo prognostic assays. The following terms and definitions apply to such antibodies.

"Antibodies" and "immunoglobulins" (Igs) are glycoproteins having the same structural characteristics. The terms are used synonymously. In some instances the antigen specificity of the immunoglobulin may be known.

The term "antibody" is used in the broadest sense and covers fully assembled antibodies, antibody fragments that can bind antigen (e.g., Fab, F(ab')$_2$, Fv, single chain antibodies, diabodies, antibody chimeras, hybrid antibodies, bispecific antibodies, humanized antibodies, and the like), and recombinant peptides comprising the forgoing.

The terms "monoclonal antibody" and "mAb" as used herein refer to an antibody obtained from a substantially homogeneous population of antibodies, i.e., the individual antibodies comprising the population are identical except for possible naturally occurring mutations that may be present in minor amounts.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy-chain variable domains.

The term "variable" refers to the fact that certain portions of the variable domains differ extensively in sequence among antibodies. Variable regions confer antigen-binding specificity. However, the variability is not evenly distributed throughout the variable domains of antibodies. It is concentrated in three segments called complementarity determining regions (CDRs) or hypervariable regions, both in the light chain and the heavy-chain variable domains. The more highly conserved portions of variable domains are celled in the framework (FR) regions. The variable domains of native heavy and light chains each comprise four FR regions, largely adopting a β-pleated-sheet configuration, connected by three CDRs, which form loops connecting, and in some cases forming part of, the β-pleated-sheet structure. The CDRs in each chain are held together in close proximity by the FR regions and, with the CDRs from the other chain, contribute to the formation of the antigen-binding site of antibodies (see, Kabat et al. (1991) *NIH PubL. No.* 91-3242, Vol. I, pages 647-669). The constant domains are not involved directly in binding an antibody to an antigen, but exhibit various effector functions, such as Fc receptor (FcR) binding, participation of the antibody in antibody-dependent cellular toxicity, initiation of complement dependent cytotoxicity, and mast cell degranulation.

The term "hypervariable region," when used herein, refers to the amino acid residues of an antibody that are responsible for antigen-binding. The hypervariable region comprises amino acid residues from a "complementarily determining region" or "CDR" (i.e., residues 24-34 (L1), 50-56 (L2), and 89-97 (L3) in the light-chain variable domain and 31-35 (H1), 50-65 (H2), and 95-102 (H3) in the heavy-chain variable domain; Kabat et al. (1991) *Sequences of Proteins of Immunological Interest*, 5th Ed. Public Health Service, National Institute of Health, Bethesda, Md.) and/or those residues from a "hypervariable loop" (i.e., residues 26-32 (L1), 50-52 (L2), and 91-96 (L3) in the light-chain variable domain and (H1), 53-55 (H2), and 96-101 (13) in the heavy chain variable domain; Clothia and Lesk, (1987) *J. Mol. Biol.,* 196:901-917). "Framework" or "FR" residues are those variable domain residues other than the hypervariable region residues, as herein deemed.

"Antibody fragments" comprise a portion of an intact antibody, preferably the antigen-binding or variable region of the intact antibody. Examples of antibody fragments include Fab, Fab, F(ab')2, and Fv fragments; diabodies; linear antibodies (Zapata et al. (1995) *Protein Eng.* 10:1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen recognition and binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain ($C_H1$) of the heavy chain. Fab fragments differ from Fab' fragments by the addition of a few residues at the carboxy terminus of the heavy chain $C_H1$ domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of human immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Different isotypes have different effector functions. For example, human IgG1 and IgG3 isotypes have ADCC (antibody dependent cell-mediated cytotoxicity) activity.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

"Human effector cells" are leukocytes that express one or more FcRs and perform effector functions. Preferably, the cells express at least FcγRIII and carry out antigen-dependent cell-mediated cyotoxicity (ADCC) effector function. Examples of human leukocytes that mediate ADCC include peripheral blood mononuclear cells (PBMC), natural killer (NK) cells, monocytes, macrophages, eosinophils, and neutrophils, with PBMCs and NK cells being preferred. Antibodies that have ADCC activity are typically of the IgG1 or IgG3 isotype. Note that in addition to isolating IgG1 and IgG3 antibodies, such ADCC-mediating antibodies can be made by engineering a variable region from a non-ADCC antibody or variable region fragment to an IgG1 or IgG3 isotype constant region.

The terms "Fc receptor" or "FcR" are used to describe a receptor that binds to the Fc region of an antibody. The preferred FcR is a native-sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see Daeron (1997) *Annu. Rev. Immunol.* 15:203-234). FcRs are reviewed in Ravetch and Kinet (1991) *Annu. Rev. Immunol.* 9:457-492; Capel et al. (1994) *Immunomethods* 4:25-34; and de Haas et al. (1995) *J. Lab. Clin. Med.* 126:330-341. Other FcRs, including those to be identified in the future, are encompassed by the term "FcR" herein. The term also includes the neonatal receptor, FcRn, which is responsible for the transfer of maternal IgGs to the fetus (Guyer et al. (1976) *J Immunol.* 117:587 and Kim et al. (1994) *J. Immunol.* 24:249).

There are a number of ways to make human antibodies. For example, secreting cells can be immortalized by infection with the Epstein-Barr virus (EBV). However, EBV-infected cells are difficult to clone and usually produce only relatively low yields of immunoglobulin (James and Bell (1987) *J. Immunol. Methods* 100:5-40). In the future, the immortalization of human B cells might possibly be achieved by introducing a defined combination of transforming genes. Such a possibility is highlighted by a recent demonstration that the expression of the telomerase catalytic subunit together with the SV40 large oncoprotein and an oncogenic allele of H-ras resulted in the tumorigenic conversion of normal human epithelial and fibroblast cells (Hahn et al. (1999) Nature 400: 464-468). It is now possible to produce transgenic animals (e.g., mice) that are capable, upon immunization, of producing a repertoire of human antibodies in the absence of endogenous immunoglobulin production (Jakobovits et al. (1993) Nature 362:255-258; Lonberg and Huszar (1995) Int. Rev. Immunol. 13:65-93; Fishwild et al. (1996) Nat. Biotechnol. 14:845-851; Mendez et al. (1997) Nat. Genet. 15:146-156; Green (1999) J. Immunol. Methods 231:11-23; Tomizuka et al. (2000) Proc. Natl. Acad. Sci. USA 97:722-727; reviewed in Little et al. (2000) Immunol. Today 21:364-370). For example, it has been described that the homozygous deletion of the antibody heavy-chain joining region ($J_H$) gene in chimeric and germ-line mutant mice results in complete inhibition of endogenous antibody production (Jakobovits et al. (1993) Proc. Natl. Acad. Sci. USA 90:2551-2555). Transfer of the human germ-line immunoglobulin gene array in such germ-line mutant mice results in the production of human antibodies upon antigen challenge (Jakobovits et al. (1993) Nature 362:255-258). Mendez et al. (1997) (Nature Genetics 15:146-156) have generated a line of transgenic mice that, when challenged with an antigen, generates high affinity fully human antibodies. This was achieved by germ-line integration of megabase human heavy-chain and light-chain loci into mice with deletion into endogenous $J_H$ segment as described above. These mice (XenoMouse® II technology (Abgenix; Fremont, Calif.)) harbor 1,020 kb of human heavy-chain locus containing approximately 66 $V_H$ genes, complete $D_H$ and $J_H$ regions, and three different constant regions, and also harbors 800 kb of human κ locus containing 32 Vκ genes, Jκ segments, and Cκ genes. The antibodies produced in these mice closely resemble that seen in humans in all respects, including gene rearrangement, assembly, and repertoire. The human antibodies are preferentially expressed over endogenous antibodies due to deletion in endogenous segment that prevents gene rearrangement in the murine locus. Such mice may be immunized with an antigen of particular interest.

Sera from such immunized animals may be screened for antibody reactivity against the initial antigen. Lymphocytes may be isolated from lymph nodes or spleen cells and may further be selected for B cells by selecting for CD138-negative and CD19-positive cells. In one aspect, such B cell cultures (BCCs) may be fused to myeloma cells to generate hybridomas as detailed above.

In another aspect, such B cell cultures may be screened further for reactivity against the initial antigen, preferably. Such screening includes enzyme-linked immunosorbent assay (ELISA) with the target/antigen protein, a competition assay with known antibodies that bind the antigen of interest, and in vitro binding to transiently transfected CHO or other cells that express the target antigen.

Biomarkers, Cytokine Markers, CD40-Related Factors, and Clinically Useful Prognostic Markers for Use in the Prognostic Assays of the Invention In some embodiments, the methods of the present invention comprise the use of ex vivo prognostic assays to monitor changes in the expression level of one or more biomarkers of cell survival, proliferation, apoptosis, and CD40 signaling pathways. The ex vivo prognostic assays can be used alone, or in combination with other prognostic assays, for example, prognostic assays that identify candidate subjects having a cancer or pre-malignant condition that would be responsive to treatment with anti-CD40 therapeutic agents based on expression of other CD40-related factors and/or based on the presence or absence of, or elevated or diminished expression of, other clinically useful prognostic markers that are indicative of poor prognosis with treatment intervention with standard therapeutic agents having a different mode of action from that exerted by anti-CD40 therapeutic agents. By "responsive to treatment with an anti-CD40 therapeutic agent" is intended the candidate subject (i.e., an individual with a cancer or pre-malignant condition as noted herein below), when treated with the anti-CD40 therapeutic agent, would have a positive therapeutic response with respect to the cancer or pre-malignant condition for which treatment is sought.

Biomarkers for Use in Ex Vivo Prognostic Assays.

Signaling pathways are characterized by protein families that facilitate signal transduction. The term "family" when referring to protein and nucleic acid molecules is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

The AKT (sometimes referred to as PKB, for protein kinase B) family of serine/threonine kinases, is integrally involved in cell growth, survival, and metabolism. PKB was originally identified as a retroviral oncogene. Currently, three variants of the AKT family, the 480-residue AKT-1, the 481-residue AKT-2, and the 479-residue AKT-3, have been characterized. The role of the Akt genes in malignancy is exemplified by their amplification and/or the overexpression of the AKT proteins in a number of cancers. See, for example, Nicholson and Anderson (2002) Cell Signal 14:381-398; Sun et al. (2001) Cancer Res. 61:5985-5991; Cheng et al. (1997) Oncogene 14:2793-2801; Ruggeri et al. (1998) Mol. Carcinog. 21:81-86; Liu et al. (1998) Cancer Res. 58:2973-2977; Lin et al. (2001) Langenbecks Arch. Surg. 386:293-301). For purposes of the present invention, members of the AKT family of proteins will be referred to generally as AKT proteins, though it is recognized that the methods of the present invention apply to all three forms of AKT, i.e., AKT-1, AKT-2, and AKT-3, and variants thereof.

AKT is a growth factor-regulated serine/threonine kinase that contains a PH (pleckstrin homology) domain. This PH domain interacts with lipid products of phosphatidylinositol 3-kinase (PI3K), phosphatidylinositol-3,4-biphosphate, and phosphatidylinositol-3,4,5-triphosphate, which results in translocation of AKT from a cell's cytosol to its plasma membrane. This translocation is required in order to present AKT to an upstream activation kinase, PDK1 (phosphoinositide-dependent kinase 1). A variety of survival and growth factors such as PDGF, EGF, insulin, thrombin, and NGF are known to activate the translocation of AKT. The activated (i.e., phosphorylated) form of AKT/PKB protein phosphorylates numerous substrates, including GSK-3 (glycogen synthase kinase 3), eNOS (endothelial nitric oxide synthase), FKHR 1 (forkhead transcription factor family member 1), Bad (Bcl-2 pro-apoptotic family member), and p21 CIP (inhibitor of cell cycle progression). These actions can result in diverse biological effects such as suppression of apoptosis, control of glucose metabolism, cell proliferation, transcription, translation, cell migration, and angiogenesis.

The AKT proteins have anti-apoptotic activity that correlates with their activation when cells become cancerous. It is believed that the phosphorylation of AKT triggers nucleo-cytoplasmic localization of substrates involved in cell cycle and apoptosis. This leads to a host of events culminating in malignancy, including acquired growth signal autonomy, insensitivity to apoptotic signals, unlimited replication, sustained angiogenesis, tissue invasion, and metastasis.

Activated AKT (i.e., p-AKT) promotes cell survival through several distinct pathways that involve phosphorylation of downstream effector molecules. First, p-AKT inhibits apoptosis by phosphorylating the Bad component of the Bad/Bcl-xl complex. Phosphorylated Bad binds to 14-3-3 causing dissociation of the Bad/Bcl-xl complex and thereby freeing Bcl-xl to allow for cell survival. Second, NF-κB, which is kept inactive in the cytoplasm through association with inhibitory proteins of the I kappa-B (Iκ-B) family, can be activated by interaction with NF-κB inducing kinase (NIK) or it can be activated by the AKT signaling pathway. In this manner, activated AKT (i.e., p-AKT) activates an NF-κB inhibitory molecule of the Iκ-B family (for example, Iκ-Bα), via intermediate phosphorylation of the Iκ-B kinase multi-protein complex (IKK-α/β); activation of an Iκ-B leads to its degradation and release of previously bound NF-κB, which leads to activation of this transcription factor. The active form of NF-κB can then translocate into the nucleus and regulate the expression of hundreds of genes to oppose apoptosis. Another means by which AKT promotes cell survival and opposes apoptosis is by phosphorylation of the protease Caspase 9 or forkhead transcription factors such as FKHRL1.

In some embodiments, the methods of the present invention to identify subjects having a cancer or pre-malignant condition that would benefit from treatment with an anti-CD40 therapeutic agent that blocks or interferes with CD40L-mediated CD40 signaling comprise the use of an ex vivo prognostic assay to monitor the effects of anti-CD40 therapeutic agents on CD40 signaling through the AKT and NF-κB signaling pathways. In this manner, a test biological sample collected from a candidate subject is contacted with the anti-CD40 therapeutic agent of interest for sufficient time to allow for modulation of CD40L-mediated CD40 signaling as noted herein below, and that sample is then assayed for changes in the expression level of at least one CD40 signaling biomarker selected from the group consisting of phosphorylated AKT (p-AKT), phosphorylated PI3K (p-PI3K), phosphorylated PDK1 (p-PDK1), phosphorylated IKK-α/β (p-IKK-α/β), phosphorylated Iκ-B (p-Iκ-B; for example, p-Iυ-Bα), and activated NF-κB. Detection of decreased expression levels of these phosphorylated biomarkers in a test biological sample comprising CD40L-stimulated CD40-expressing neoplastic cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given biomarker of CD40 signaling through the AKT and NF-κB signaling pathways is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

CD40/CD40L interaction also leads to activation of the MAPK signaling cascades including the MEK/ERK signaling pathway, the MEK/p38 signaling pathway, and the MEKK/JNKK/JNK signaling pathway. All MAPK pathways operate through sequential phosphorylation events to phosphorylate transcription factors and regulate gene expression. They can also phosphorylate cytosolic targets to regulate intracellular events. These cascades are implicated in the regulation of cellular proliferation, differentiation, development, cell cycle, and transmission of oncogenic signals. Of particular interest to the methods of the present invention are activation of the MEK/ERK and MEK/p38 signaling pathways.

The MAP kinases (also referred to as extracellular signal-regulated protein kinases, or ERKs) are the terminal enzymes in a three-kinase cascade, where each enzyme phosphorylates and thereby activates the next member in the sequence. Each MAPK module consists of three protein kinases: a MAPK kinase kinase (or MEKK) that activates a MAPK kinase (or MEK), which in turn activates a MAPK/ERK enzyme. The MEKKs are serine/threonine-specific protein kinases that dually phosphorylate, and thereby activate, one or more of the MEK enzymes on Ser or Thr residues (Ser-X-X-X-Ser/Thr) within the catalytic core. The MEKs are Serine/Threonine/Tyrosine-specific protein kinases that activate MAPKs by phosphorylating both Thr and Tyr within the TXY consensus sequence of the MAPKs. This dual phosphorylation is required for activation. ERK1 (p44), ERK2 (p42), p38/HOG, and JNK/SAPK represent related yet distinct terminal MAPKs in parallel pathways.

In some embodiments, the methods of the invention to identify subjects having a cancer or pre-malignant condition that would benefit from treatment with an anti-CD40 therapeutic agent comprise the use of an ex vivo prognostic assay to monitor the effects of anti-CD40 therapeutic agents on CD40 signaling through the MEK/ERK and MEK/p38 pathways. In this manner, a test biological sample collected from a candidate subject is contacted with the therapeutic agent of interest for sufficient time to allow for modulation of CD40L-mediated CD40 signaling as noted herein below, and that sample is then assayed for changes in the expression level of at least one CD40 signaling biomarker selected from the group consisting of phosphorylated MEK (p-MEK), for example, p-MEK1, p-MEK2, p-MEK3, and p-MEK6, phosphorylated ERK (p-ERK), for example, p-ERK1 or p-ERK2, and phosphorylated p38 (p-p38). Detection of decreased expression levels of these phosphorylated biomarkers in a biological sample comprising CD40L-stimulated CD40-expressing neoplastic cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given biomarker of CD40 signaling through the MEK/ERK and MEK/p38 pathways is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

Responsiveness of a candidate subject to therapy with an anti-CD40 therapeutic agent that blocks or interferes with CD40L-mediated CD40 signaling can also be assessed by monitoring ex vivo effects of the therapeutic agent on expression level of any of the cytokine markers of CD40L-mediated CD40 signaling. Engagement of CD40 by its natural ligand in vivo results in upregulation of a number of proinflammatory cytokines depending upon the type of CD40-expressing cell. Ex vivo CD40L stimulation of normal B cells results in upregulation of production of several cytokines, including, but not limited to, vascular endothelial growth factor (VEGF), interleukin (IL)-6, IL-8, IL-10, tumor necrosis factor-α (TNF-α), monocyte chemoattractant protein-1 (MCP-1), and macrophage inflammatory protein-1β (MIP-1β), while ex vivo CD40L stimulation of neoplastic B-cells, for example chronic lymphocytic leukemia cells, results in upregulation of production of VEGF, IL-8, IL-10, granulocyte monocyte colony-stimulating factor (GM-CSF), TNF-α, and MCP-1, as noted herein below.

In accordance with the screening methods of the present invention, a test biological sample collected from a candidate subject is contacted with the anti-CD40 therapeutic agent of interest for sufficient time to allow for modulation of CD40L-mediated CD40 signaling as noted herein below, and that sample is then assayed for changes in the expression level of at least one cytokine marker selected from the group consisting of VEGF, IL-6, IL-8, IL-10, GM-CSF, TNF-α, MCP-1, and MIP-1β. Level of expression of cytokines can be accomplished using any detection method known in the art as noted herein below. Detection of decreased expression levels of these cytokine markers in a test biological sample comprising CD40L-stimulated CD40-expressing neoplastic cells in response to incubation with an anti-CD40 therapeutic agent relative to that observed for a control biological sample is indicative of downregulation of CD40L-mediated CD40 signaling, and therefore indicative of a positive treatment outcome with that anti-CD40 therapeutic agent. In some embodiments, the level of expression of any given cytokine is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

The AKT, NF-κB, and MAPK signaling pathways are all involved in cell proliferation and survival. In the immune system, apoptosis plays an important role in selection of T cell repertoire, deletion of self-reactive T and B lymphocytes, removal of peripheral effector T cells following termination of an immune response, regulation of immunological memory, and in the cytotoxicity of target cells by CTL and NK cells. For malignancies of B-cell lineage, aberrant regulation of the balance between B cell proliferation and apoptosis results in uncontrolled proliferation of neoplastic B cells. Therapeutic agents that can block CD40 survival signaling on neoplastic B cells and promote cellular apoptotic processes would be beneficial in treating pre-malignant conditions and malignancies of B-cell lineage.

Thus, in addition to monitoring CD40 signaling on neoplastic cells, the methods of the present invention to identify subjects having a cancer or pre-malignant condition that would benefit from treatment with an anti-CD40 therapeutic agent comprise the use of ex vivo prognostic assays that monitor the effects of anti-CD40 therapeutic agents on expression of one or more biomarkers of apoptosis, particularly cellular pro-apoptotic proteins, including, but not limited to, cleaved caspase proteins and cleaved poly ADP-ribose polymerase (PARP). Additional biomarkers of apoptosis that can be assayed include, but are not limited to, alterations in the plasma membrane at the cell surface, for example, presence of cell surface phosphotidylserine (PS), and cleavage or fragmentation of genomic DNA. PS normally is located exclusively at the inner side of the plasma membrane, but is translocated to the external surface of the cell during the early phases of apoptotic cell death during which the cell membrane remains intact. Presence of cell surface PS and genomic DNA fragmentation can be detected, for example, by annexin V staining and TUNEL staining, respectively, as noted herein below. Detection of increased expression levels of one or more of these biomarkers of apoptosis in a test biological sample comprising CD40L-stimulated CD40-expressing neoplastic cells in response to incubation with an anti-CD40 therapeutic agent relative to that observed in a control biological sample is indicative of a positive treatment outcome with that anti-CD40 therapeutic agent. In some embodiments, the level of expression of any given biomarker of apoptosis is increased by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or higher relative to that detected in the control biological sample.

Alternatively, or in combination with the ex vivo assays described above, the methods of the present invention comprise the use of ex vivo prognostic assays that monitor the effects of anti-CD40 therapeutic agents on expression of one or more proteins that are biomarkers of cell proliferation and/or cell survival, including, but not limited to, an anti-apoptotic protein that is a member of the Bcl-2 family, an IAP apoptosis inhibitor protein, and TNF receptor-associated factor-1 (TRAF-1). Detection of decreased expression levels of these biomarkers of cell proliferation and/or cell survival in a test biological sample comprising CD40-expressing neoplastic cells in response to incubation with an anti-CD40 therapeutic agent relative to that observed in a control biological sample is indicative of a positive treatment outcome with that anti-CD40 therapeutic agent. In some embodiments, the level of expression of any given biomarker of cell proliferation and/or cell survival is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the control biological sample.

Members of the caspase family of proteins are major effectors of cellular apoptosis. The caspases are cysteine proteases that exist within the cell as inactive pro-forms or so-called "zymogens." The zymogens are cleaved to form active enzymes following the induction of apoptosis either via the death receptor-mediated pathway or the mitochondrial pathway of apoptosis. See, for example, Gupta et al. (2003) *Intl. J. Oncol.* 22:15-20; herein incorporated by reference in its entirety. Depending upon the apoptotic pathway, different caspases initiate the apoptotic process, with Caspase-8 and -10 initiating the death receptor pathway, and Caspase-9 initiating the mitochondrial pathway. Active initiator caspases then activate (i.e., cleave) effector caspases, for example, Caspase-3, -6, and -7, to induce apoptosis. These effector caspases cleave key cellular proteins that lead to the typical morphological changes observed in cells undergoing apoptosis.

Thus, in some embodiments, the methods of the present invention to identify subjects having a cancer or pre-malignant condition that would benefit from treatment with an anti-CD40 therapeutic agent comprise the use of ex vivo prognostic assays to monitor the proteolysis of specific cellular proteins associated with apoptosis. For example, poly (ADP-ribose) polymerase (PARP-1) is specifically cleaved during apoptosis. PARP-1 is a DNA-binding protein that catalyzes the addition of poly(ADP-ribose) chains to some nuclear proteins and is thought to play a critical role in DNA damage repair. PARP-1 is rapidly activated during cellular stresses, such as heat shock, ionizing radiation, exposure to carcinogens, and treatment with chemotherapy agents (Scovassi and Poirier (1999) *Mol. Cell. Biochem.* 199:125-137; Wyllie (1997) *Eur. J. Cell Biol.* 73:189-197). During apoptosis, activated (i.e., cleaved) caspase-3 in turn cleaves PARP-1; in fact, the resolution of the 89 kDa and 24 kDa proteolytic fragments is accepted as a hallmarks of apoptosis (Scovassi and Poirier (1999) supra; Wyllie et al. (1997) supra. The ex vivo prognostic assays described herein monitor changes in the level of one or more cleaved Caspase proteins, for example, cleaved Caspase-3, cleaved Caspase-7, and cleaved Caspase-9, and optionally, the level of cleaved PARP-1, cell surface PS, and/or genomic DNA fragmentation, in a test biological sample obtained from a candidate subject in response to anti-CD40 therapeutic agents that modulate CD40L-mediated CD40 signaling and/or modulate ADCC. Elevated levels of apoptotic biomarkers within a biological sample can be detected using any method known to those of skill in the art, including those described herein below.

Biomarkers of cell survival and proliferation include, but are not limited to, anti-apoptotic proteins that are members of the Bcl-2 family of proteins. The Bcl-2 family of proteins, which comprises at least 16 members, participates in the regulation of cellular apoptosis. Some of the family members are anti-apoptotic, for example, Bcl-2, Bcl-xl, Mcl-1, Bcl-w, and A1, and thus biomarkers of cell survival, and others are pro-apoptotic (for example, Bid, Bim, Bik, Bmf, Bad, Hrk, BNIP3, Bax, Bak, and Bok), and thus biomarkers of apoptotic activity. Bcl-2 family members have been suggested to act through many different mechanisms, including pore formation in the outer mitochondrial membrane, through which cytochrome c (Cyt c) and other intermembrane proteins can escape; and heterodimerization between pro- and anti-apoptotic family members.

Effects of anti-CD40 therapeutic agents on CD40 signaling and modulation of apoptosis can be assessed with the ex vivo prognostic assays described herein to monitor one or more of these biomarkers of cell survival/apoptosis. Biomarkers of cell survival that are of particular interest include, but are not limited to, the anti-apoptotic proteins Bcl-xl and Mcl-1.

The bcl-2 gene, which encodes the mitochondrial membrane protein Bcl-2, was first identified in B-cell lymphomas (Tsujimoto et al. (1984) *Science* 226:1097) where the causal genetic lesion has been characterised as a chromosomal translocation (t(14:18)) that places the bcl-2 gene under the control of the immunoglobulin promoter. The resulting overexpression of Bcl-2 retards the normal course of apoptotic cell death that otherwise maintains B-cell homeostasis, resulting in B-cell accumulation and follicular lymphoma (Adams and Cory, 1998; Cory (1994) *Philos. Trans. R. Soc. Lond. B. Biol. Sci.* 345:289). This observation showed that cancers do not strictly arise from unrestrained cell proliferation, but could also be due to insufficient apoptotic turnover. In addition to follicular lymphomas, Bcl-2 levels are elevated in a broad range of other human cancers, indicating that this molecule may have a role in raising the apoptotic threshold in a broad spectrum of cancerous disorders. Bcl-2 can exist as a homodimer or can form a heterodimer with bax. As a homodimer, bax functions to induce apoptosis. However, the formation of a bax-Bcl-2 complex blocks apoptosis. Bcl-2 expression may also play a role in the development of drug resistance. The expression of Bcl-2 is negatively regulated by p53. Overexpression of Bcl-2 is not present in preneoplastic lesions suggesting that changes in Bcl-2 occur relatively late in tumor progression.

Several genes with homology to the bcl-2 gene have subsequently been characterized, including the following: al, which encodes the 80-amino acid A1 protein that is rapidly induced in macrophages in response to GM-CSF or LPS (Lin et al. (1993) *J. Immunol.* 151: 1979-1988); mcl-1, an early response gene in myeloid cell lines that undergo macrophage differentiation (Kozopas et al. (1993) *Proc. Natl. Acad. Sci. USA* 90:3516-3520); and bak, a bcl-2 homologue that may enhance apoptosis (Chittenden et al. (1995) *Nature* 374:733; Kiefer et al. (1995) *Nature* 374:736). Other proteins which interact with and/or are structurally related to the bcl-2 gene product have also been identified, such as for example, Bcl-xl, and Bcl-xs (Boise et al. (1993) *Cell* 74:597); Ced-9 (Vaux et al. (1992) *Science* 258:1955).

The bcl-x gene product, Bcl-x, which is closely related to the Bcl-2 protein, also protects cells from apoptosis. Alternative splicing of human Bcl-x may result in at least two distinct Bcl-x mRNA species, Bcl-xl and Bcl-xs. The predominant protein product (233 amino acids) of the larger bcl-x mRNA, Bcl-xl, inhibits cell death upon growth factor withdrawal (Boise et al. (1993) *Cell* 74:597-608) and its transgenic expression alters thymocyte maturation leading to increased numbers of mature thymocytes (Chao et al. (1995) *J. Exp. Med.* 182:821-828; Grillot et al. (1995) *J. Exp. Med.* 182: 1973-1983).

The myeloid cell leukemia associated gene mcl-1 encodes a protein, Mcl-1, that is expressed early during the programming of differentiation in myeloid cell leukemia (see, for example, U.S. Patent Application Publication No. 20020086321). The carboxyl portion of Mcl-1 shares homology to Bcl-2. Like other members of the Bcl-2 family, Mcl-1 is characterized by an association with the programming of transitions in cell fate, such as from viability to death or from proliferation to differentiation. High expression of the mcl-1 gene reportedly is associated with poor outcome in non-Hodgkin's lymphoma (Kuramoto et al. (2002) *Br. J. Haematol.* 116:158-161). Further, a relatively high level of mcl-1 gene expression reportedly correlates with high-grade morphology, a high proliferative state, and p53 overexpression in mantle cell lymphoma (MCL) (Khoury et al. (2003) *J. Pathol.* 199:90-97).

In addition to members of the Bcl-2 family, cell survival biomarkers for use in the methods of the present invention include members of the gene family of inhibitors of apoptosis related to the baculovirus IAP gene (Bimbaum et al. (1994) *J. Virol.* 68:2521-2528; Clem et al. (1994) *Mol. Cell. Biol.* 14:5212-5222; Duckett et al. (1996) *EMBO J.* (1996) 15:2685-2694; Hay et al. (1995) *Cell* 83:1253-1262; Liston et al. (1996) *Nature* 379:349-353; Rothe et al. (1995) *Cell* 83:1243-1252; Roy et al. (1995) *Cell* 80:167-178). At least eight human IAPs have been identified (Salvesen and Duckett (2002) *Nat. Rev. Mol. Cell. Biol.* 3:401-410).

The IAPs are highly conserved evolutionarily; they share a similar architecture organized in one to three approximately 70 amino acid amino terminus Cys/His baculovirus IAP repeats (BIR) and by a carboxy terminus zinc-binding domain, designated RING finger. The IAP family proteins are recognized as having potentially important roles in the regulation of apoptosis and tumorigenesis (Deveraux and Reed (1999) *Genes Dev.* 13:239-252; Tamm et al. (2000) *Clin. Cancer Res.* 6:1796-1803). The expression of survivin, one of the LAP family proteins, is significantly increased in several human cancers (Hoffman et al. (2002) *J. Biol. Chem.* 277: 3247-3257). Also, c-IAP2 has been suggested as a causative gene of mucosa-associated lymphoid tissue lymphoma and to have a role in carcinogenesis and tumor progression (Dierlamrn et al. (1999) *Blood* 93:3601-3609).

The IAPs suppress cell death by inhibiting upstream and terminal caspases (see, for example, Thompson (1995) *Science* 267:1456). The active (i.e., cleaved) forms of Caspase-3 and -7 are directly inhibited by XIAP, c-IAP1, and c-IAP2 (see, for example, Roy et al. (1997), supra), which can also prevent the proteolytic processing of pro-Caspase-3, -6, and -7 by blocking the cytochrome c-induced activation of pro-Caspase-9 (Deveraux et al. (1998) *EMBO J.* 17:2215-2223). Therapeutic and diagnostic uses of nucleic acids that encode various inhibitors of apoptosis relating to a member of the IAP family have been described in the patent literature. See, for example, International Patent Applications No. WO 97/06255, WO 97/26331, and WO 97/32601. Examples of IAP proteins that can be used as biomarkers of cell survival include, but are not limited to, XIAP, cIAP1, cIAP2, and survivin.

XIAP is the most widely expressed and most potent inhibitor of caspases (see, for example, Takahasi et al. (1998) *J. Biol. Chem.* 273:7787; Reed (1994) *J. Cell Biol.* 124:1). Expression of this IAP is reportedly elevated in certain cancers and cancer cell lines (Kornblau et al. (1999) *Clin Cancer Res.* 5:1758; Kitada et al. (1998) *Blood* 91:3379; Tamm et al. (2000) *Clin. Cancer Res.* 6:1796-1803). Downregulation of XIAP has been shown to induce apoptosis in chemoresistant human ovarian cancer cells (Altman et al. (1994) *J. Natl. Cancer Inst.* 86:829).

Survivin is an approximately 16.5 kDa cytoplasmic protein (see, for example, U.S. Patent Application Publication No. 20030100525) containing a single BIR, and a highly charged carboxyl-terminus coiled-coil region instead of a RING finger, which inhibits apoptosis induced by growth factor (IL-3) withdrawal when transferred in B cell precursors (Ambrosini et al. (1997) *Nature Med.* 3:917-921). At variance with Bcl-2 or other LAP proteins, survivin is undetectable in adult tissues, but becomes prominently expressed in all the most common human cancers of lung, colon, breast, pancreas, and prostate, and in about 50% of high-grade non-Hodgkin's lymphomas, in vivo. Survivin reportedly is negatively regulated by wild-type p53. Overexpression of exogenous survivin protein rescues cells from p53-induced apoptosis in a dose-dependent manner, suggesting that loss of survivin mediates, at least, in part the p53-dependent apoptotic pathway (Mirza et al. (2002) *Oncogene* 21:2613-2622).

Another representative biomarker of cell survival for use in the methods of the invention is TRAF-1. The TRAF family members bind to the cytoplasmic domain of CD40 and mediate activation of multiple signaling pathways that regulate B-cell survival, proliferation, differentiation, isotype switching, development of the germinal center, and the humoral memory response (see, for example, Pullen et al. (1999) *J. Biol. Chem.* 274:14246-14254). It has been reported that activation of the CD40 receptor can result in transcription of the TRAF-1 gene (Schwenzer et al. (1999) *J. Biol. Chem.* 274(27):19368-19374). The increase in TRAF-1 gene expression as a consequence of CD40 receptor activation may be differentially regulated in normal B cells and chronic lymphocytic leukemia (CLL) cells (Gricks et al. (2004) *Blood* 104(13):4002-4009). Thus while effects on TRAF-1 gene expression may or may not be indicative of CD40 activity in normal B cells, changes in TRAF-1 gene expression in response to CD40 receptor activation in neoplastic hematological cells may be predictive of drug efficacy, thereby providing a suitable biomarker for assessing and/or monitoring the effects of anti-CD40 therapeutics on CD40L-mediated CD40 signaling and modulation of cell survival/apoptosis. Changes in TRAF-1 expression can be easily detected at either the mRNA level by techniques such as Northern blot or quantitative RT-PCR or the protein level, for example, by Western blot, as noted herein below.

The foregoing biomarkers of cell survival can be monitored in the ex vivo prognostic assays described herein in any combination, including one or all of these biomarkers, as well as in combination with other biomarkers of cellular proliferation. Thus in one embodiment, the ex vivo prognostic assays described herein are also used to monitor in a test biological sample from a candidate subject the expression of the cell proliferation biomarker Ki67.

Ki67 is a cell cycle related nuclear protein that is present in the nuclei of cells in the G1, S, M and G2 phases of dividing cells, but not in the G0 phase of quiescent cells (Gerdes et al. (1984) *J. Immunol.* 133, 1710-1715). For these reason, it is used as a cell proliferation marker. It has also been used to stratify good and poor prognostic categories in invasive breast cancer (Tan et al. (2005) *Mod. Pathol.* 18:374-81) and pulmonary adenocarcinoma (Haga et al. (2003) *Ann. Thorac. Surg.* 75:1727-32). High expression of Ki67 is also associated with poor prognosis in ovarian cancer (Henriksen et al. (1994) *Gynecol. Oncol.* 53:301-6; Henzen-Logmans et al. (1994) *Int. J. Cancer* 57:468-72; Wong and Tattersall (1989) *Br. J. Obstet. Gynaecol.* 96:720-4). Additionally, antisense suppression of Ki67 protein expression has been shown to prevent cell proliferation (Schluter et al. (1993) *J. Cell Biol.* 123:513-522).

Thus the biomarkers that are to be monitored in the ex vivo prognostic assays of the present invention include the cell survival and apoptotic proteins described above, and proteins involved in the CD40 signaling pathways as noted herein above. Monitoring can be at the protein or nucleic acid level. Thus, the biomarkers include these proteins and the genes encoding these proteins. Where detection is at the protein level, the biomarker protein comprises the full-length polypeptide or any detectable fragment thereof, and can include variants of these protein sequences. Similarly, where detection is at the nucleotide level, the biomarker nucleic acid includes DNA comprising the full-length coding sequence, a fragment of the full-length coding sequence, variants of these sequences, for example naturally occurring variants or splice-variants, or the complement of such a sequence. Biomarker nucleic acids also include RNA, for example, mRNA, comprising the full-length sequence encoding the biomarker protein of interest, a fragment of the full-length RNA sequence of interest, or variants of these sequences. Biomarker proteins and biomarker nucleic acids also include variants of these sequences. By "fragment" is intended a portion of the polynucleotide or a portion of the amino acid sequence and hence protein encoded thereby. Polynucleotides that are fragments of a biomarker nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention. "Variant" is intended to mean substantially similar sequences. Generally, variants of a particular biomarker of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that biomarker as determined by sequence alignment programs known in the art. The protein and corresponding coding sequence for each of these markers is known in the art. See Table 6 in Example 5 herein below.

CD40-Related Factors and Clinically Useful Prognostic Markers for Use in Other Prognostic Assays.

In accordance with the methods of the present invention, individuals or subpopulations of patients having a cancer or pre-malignant condition that would benefit from treatment with anti-CD40 therapeutic agents can also be identified using prognostic assays that look for the presence or absence of, or elevated or diminished levels of, one or more CD40-related factors. Subjects identified as being responsive to treatment with an anti-CD40 therapeutic agent on the basis of these CD40-related factors can be treated with the anti-CD40 therapeutic agent. Alternatively, they can be further screened for potential benefit from treatment with anti-CD40 therapeutic agents using the ex vivo prognostic assays described herein, for example, to identify whether the cancer or pre-malignant condition would be more responsive to treatment with an anti-CD40 therapeutic agent that blocks CD40L-mediated CD40 signaling or which modulates ADCC activity, or which has both of these modes of action.

CD40-related factors of interest include, but are not limited to, expression level of cell surface CD40 antigen, expression level of cell surface CD40L, circulating levels of soluble CD40 (sCD40), and circulating levels of soluble CD40L (sCD40L). In this manner, a biological sample collected from a candidate subject is analyzed for expression level of at least one of these CD40-related factors. The expression level of these CD40-related factors may be used as prognostic markers for CLL and other cancers of B-cell lineage. They may be useful as diagnostics of subjects who would or would not respond to anti-CD40 therapeutic agents.

Any method known in the art can be used for analysis of these markers. Circulating levels of ssCD40 or sCD40L, for example, in a blood sample obtained from a candidate subject, can be measured, for example, by ELISA, radioimmunoassay (RIA), electrochemiluminescence (ECL), Western blot, multiplexing technologies, or other similar methods. Cell surface expression of CD40 or CD40L can be measured, for example, by flow cytometry, immunohistochemistry, Western Blot, immunoprecipitation, magnetic bead selection, and quantification of cells expressing either of these cell surface markers. CD40 and CD40L RNA expression levels could be measured by RT-PCR, Qt-PCR, microarray, Northern blot, or other similar technologies. The sequences for the CD40 antigen, CD40L, and soluble CD40L are known in the art. See, for example, Table 7 in Example 5 herein below. In some embodiments, the sCD40 is isolated and sequenced to ascertain a distinction between sCD40 that is secreted by the CD40-expressing neoplastic cells versus sCD40 that is proteolytically cleaved from the surface of these cells. Expression level of secreted sCD40 and/or proteolytically cleaved sCD40 can be correlated to disease state and/or to responsiveness of the disease to treatment with an anti-CD40 therapeutic agent of interest.

In other embodiments of the invention, subpopulations of patients having a cancer or pre-malignant condition that would benefit from treatment with an anti-CD40 therapeutic agent are identified by screening candidate subjects for one or more clinically useful prognostic markers known in the art. Any clinically useful prognostic marker known to those of skill in the art can be used. In some embodiments, the subpopulation includes patients having chronic lymphocytic leukemia (CLL), and the clinically useful prognostic markers of particular interest include, but are not limited to, ZAP-70, CD38, β2 microglobulin, and cytogenetic markers, for example, p53 mutational status, ATM mutational status, chromosome deletions, such as the chromosome 17p deletion and the chromosome 11q deletion, all of which are clinically useful prognostic markers for this disease. Thus, in one embodiment, the subpopulation of candidate subjects represents patients with CLL for whom current therapies of treatment are not curative, but for whom therapy with an anti-CD40 therapeutic agent would be beneficial.

ZAP-70 is a tyrosine kinase that associates with the zeta subunit of the T cell antigen receptor (TCR) and plays a pivotal role in T cell activation and development (Chan et al. (1992) Cell 71:649-662). ZAP-70 undergoes tyrosine phosphorylation and is essential in mediating signal transduction following TCR stimulation. Overexpression or constitutive activation of tyrosine kinases has been demonstrated to be involved in a number of malignancies including leukemias and several types of solid tumors. For example, increased ZAP-70 RNA expression levels are a prognostic marker of chronic lymphocytic leukemia (CLL) (Rosenwald et al. (2001) J. Exp. Med. 194:1639-1647). ZAP-70 is expressed in T-cells and natural killer cells, but is not known to be expressed in normal B-cells. However, ZAP-70 is expressed at high levels in the B-cells of chronic lymphocytic leukemia/small lymphocytic lymphoma (CLL/SLL) patients, and more particularly in the subset of CLL patients who tend to have the more aggressive clinical course that is found in CLL/SLL patients with unmutated Ig genes (Wiestner et al. (2003) Blood 101: 4944-4951; U.S. Patent Application Publication No. 20030203416). Because of the correlation between ZAP-70 expression levels and Ig gene mutation status, ZAP-70 can be used as a prognostic indicator to identify those patients likely to have severe disease (high ZAP-70, unmutated Ig genes), and who are therefore candidates for aggressive therapy.

CD38 is a signal transduction molecule as well as an ectoenzyme catalyzing the synthesis and degradation of cyclic ADP ribose (cADPR). CD38 expression is present at high levels in bone marrow precursor B cells, is down-regulated in resting normal B cells, and then is re-expressed in terminally differentiated plasma cells (Campana et al. (2000) Chem. Immunol. 75:169-188). CD38 is a reliable prognostic indicator in B-CLL, with the expression of CD38 generally indicating a less favorable outcome (D'Arena et al. (2001) Leuk. Lymphoma 42:109; Del Poeta et al. (2001) Blood 98:2633; Durig et al. (2002) Leukemia 16:30; Ibrahim et al. (2001) Blood 98:181; Deaglio et al. (2003) Blood 102:2146-2155). The unfavorable clinical indications that CD38 expression has been associated with include an advanced stage of disease, poor responsiveness to chemotherapy, a shorter time before initial treatment is required, and a shorter survival time (Deaglio et al. (2003) Blood 102:2146-2155). Initially, a strong correlation between CD38 expression and IgV gene mutation was observed, with patients having unmutated V genes displaying higher percentages of CD38$^+$ B-CLL cells than those with mutated V genes (Damle et al. (1999) Blood 94:1840-1847). However, subsequent studies have indicated that CD38 expression does not always correlate with the rearrangement of the IgV genes (Hamblin et al. (2002) Blood 99:1023; Thunberg et al. (2001) Blood 97:1892).

p53 is a nuclear phosphoprotein that acts as a tumor suppressor. Wild-type p53 is involved in regulating cell growth and division. p53 binds to DNA, stimulating the production of a protein (p21) that interacts with a cell division-stimulating protein (cdk2). When p21 is bound to cdk2, the cell is blocked from entering the next stage of cell division. Mutant p53 is incapable of binding DNA effectively, thus preventing p21 from acting as the stop signal for cell division, resulting in uncontrolled cell division, and tumor formation. p53 also regulates the induction of programmed cell death (apoptosis) in response to DNA damage, cell stress or the aberrant expression of some oncogenes. Expression of wild type p53 in some cancer cell lines has been shown to restore growth suppression control (Casey et al. (1991) Oncogene 6:1791-1797; Takahashi et al. (1992) Cancer Res. 52:734-736). Mutations in p53 are found in most tumor types, including tumors of the colon, breast, lung, ovary, bladder, and many other organs. p53 mutations have been found to be associated with Burkitt's lymphoma, L3-type B-cell acute lymphoblastic leukemia, B-cell chronic lymphocytic leukemia (Gaidano et al.

(1991) *Proc. Natl. Acad. Sci. U.S.A.* 88:5413-5417). p53 abnormalities have also been found associated with B-cell prolymphocytic leukemia (Lens et al. (1997) *Blood* 89:2015-2023). The gene for p53 is located on the short arm of chromosome 17 at 17p13.105-p12.

β2-microglobulin is an extracellular protein that is noncovalently associated with the α chain of the class I major histocompatibility complex (MHC). It is detectable in the serum, and is an adverse prognostic indicator in CLL (Keating et al. (1998) *Blood* 86:606a) and Hodgkin's lymphoma (Chronowski et al. (2002) *Cancer* 95:2534-2538). It is clinically used for lymphoproliferative diseases including leukemia, lymphoma, and multiple myeloma, where serum β2-microglobulin levels are related to tumor cell load, prognosis, and disease activity (Bataille et al. (1983) *Br. J. Haematol.* 55:439-447; Aviles et al. (1992) *Rev. Invest. Clin.* 44:215-220). P2 microglobulin is also useful in staging myeloma patients (Pasqualetti et al. (1991) *Eur. J. Cancer* 27:1123-1126).

Cytogenetic aberrations may also be used as markers to predict poor response to current cancer therapies. Chromosome abnormalities are found in a large percentage of CLL patients and are helpful in predicting the course of CLL. For example, a 17p deletion is indicative of aggressive disease progression. In addition, CLL patients with a chromosome 17p deletion or mutation in p53, or both, are known to respond poorly to chemotherapeutics and rituximab. Allelic loss on chromosome 17p may be also be a useful prognostic marker in colorectal cancer, where patients with a 17p deletion are associated with an increased tendency of disease dissemination in colorectal cancer (Khine et al. (1994) *Cancer* 73:28-35).

Deletions of the long arm of chromosome 11 (11q) are one of the most frequent structural chromosome aberrations in various types of lymphoproliferative disorders. CLL patients with chromosome 11q deletion and possibly ATM mutations have a poor survival compared to patients without either this defect or the 17p deletion. Furthermore, an 11q deletion is often accompanied by extensive lymph node involvement (Dohner et al. (1997) *Blood* 89:2516-2522). This deletion also identifies patients who are at high risk for disease persistence after high-dose therapy and autologous transplantation.

The ataxia telangiectasia mutated (ATM) gene is a tumor suppressor gene that is involved in cell cycle arrest, apoptosis, and repair of DNA double-strand breaks. It is found on chromosome 11. ATM mutations are associated with increased risk for breast cancer among women with a family history of breast cancer (Chenevix-Trench et al. (2002) *J. Natl. Cancer Inst.* 94:205-215; Thorstenson et al. (2003) *Cancer Res.* 63:3325-3333) and/or early-onset breast cancers (Izatt et al. (1999) *Genes Chromosomes Cancer* 26:286-294; Teraoka et al. (2001) *Cancer* 92:479-487). There is also a high frequency of association of rhabdomyosarcoma with ATM gene mutation/deletion (Zhang et al. (2003) *Cancer Biol. Ther.* 1:87-91).

Methods for detecting chromosomal abnormalities in a patient are well know in the art (see, for example, Cuneo et al. (1999) *Blood* 93:1372-1380; Dohner et al. (1997) *Blood* 89:2516-2522). Methods to measure mutated proteins, such as ATM, are well known in the art (see, for example, Butch et al. (2004) *Clin. Chem.* 50: 2302-2308).

Thus, subpopulations of cancer patients that are less responsive to existing therapeutics can be readily identified by currently used assay methods, including prognostic assays disclosed herein that utilize one or more of these clinically useful prognostic markers. Having identified a subject that falls within one of these subpopulations based on these clinically useful prognostic markers, the subject can be further screened using one or more of the ex vivo prognostic assays identified herein above to assess the benefit of treating this subject with an anti-CD40 therapeutic that modulates CD40L-mediated CD40 signaling and/or ADCC activity.

Prognostic Assays

In some embodiments of the present invention, potential therapeutic benefit with an anti-CD40 therapeutic agent that modulates CD40L-mediated CD40 signaling, modulates ADCC, or both is assessed using ex vivo prognostic assays that monitor changes in the expression level of one or more of the aforementioned biomarkers of cell proliferation and survival, cellular apoptosis, and CD40 signaling pathways in a biological sample that is collected from a candidate subject that is in need of therapeutic intervention for a cancer or pre-malignant condition that is mediated by stimulation of CD40 signaling on CD40-expressing cells. By "CD40-expressing cell" is intended normal, pre-malignant, and malignant cells expressing CD40 antigen. In some embodiments, the CD40-expressing cell is a malignant B cell. By "malignant" B cell is intended any neoplastic B cell, including but not limited to B cells derived from lymphomas including low-, intermediate-, and high-grade B cell lymphomas, immunoblastic lymphomas, non-Hodgkin's lymphomas, Hodgkin's disease, Epstein-Barr Virus (EBV) induced lymphomas, and AIDS-related lymphomas, as well as B cell acute lymphoblastic leukemias, myelomas, chronic lymphocytic leukemias, and the like. In other embodiments, the CD40-expressing cell is a carcinoma or sarcoma cell. By "CD40-expressing carcinoma cell" or CD40-expressing sarcoma cell" is intended any malignant (i.e., neoplastic) or pre-malignant carcinoma or sarcoma cell of a solid tumor that expresses the CD40 cell-surface antigen. For purposes of the present invention, cancerous and pre-cancerous or pre-malignant cells that express the CD40 antigen are referred to as "CD40-expressing neoplastic cells." Methods for detecting CD40 expression in cells are well known in the art and include, but are not limited to, PCR techniques, immunohistochemistry, flow cytometry, Western blot, ELISA, and the like. Where the ex vivo assays generate a favorable change in the expression level of one or more biomarkers of interest within the biological sample, treatment intervention with the anti-CD40 therapeutic agent is warranted. Furthermore, biomarkers, cytokine markers, and CD40-related factors discussed herein can be used to monitor treatment efficacy of an anti-CD40 therapeutic agent in a subject, who may or may not have been screened using the ex vivo prognostic assays disclosed herein, and thus determine whether further treatment with the same anti-CD40 therapeutic agent is warranted, or whether alternative treatment protocols are necessary or desirable. Where treatment with an anti-CD40 therapeutic agent is warranted as determined by the methods of the present invention, the therapeutic agent can be administered by any suitable route of administration.

The candidate subject who is being considered for treatment intervention with an anti-CD40 therapeutic agent that modulates CD40L-mediated CD40 signaling, modulates ADCC, or both can be afflicted with, or at risk of developing or relapsing with, any cancer or pre-malignant condition that is mediated by CD40 signaling on CD40-expressing neoplastic cells. Examples of such cancers and pre-malignant conditions include, but are not limited to, any of the cancers of B-cell lineage, non-B cell hematological malignancies, and solid tumors that are known to be mediated via CD40 signaling on CD40-expressing neoplastic cells.

Examples of cancers of B-cell lineage that comprise CD40-expressing neoplastic cells are acute lymphoblastic leukemia (ALL), chronic lymphocytic leukemia (CLL), pro-lymphocytic leukemia (PLL), hairy cell leukemia, Hodgkin's disease, multiple myeloma, Waldenstrom's macroglobulinemia, heavy chain disease, and the lymphomas, including, but not limited to, diffuse small lymphocytic lymphoma, follicular, DLBCL, mucosal associated lymphoid tissue lymphoma, monocytoid B cell lymphoma, splenic lymphoma, lymphomatoid granulomatosis, intravascular lymphomatosis, immunoblastic lymphoma, AIDS-related lymphoma, and the like.

Thus, the methods of the invention find use in the identification and treatment of subjects having non-Hodgkin's lymphomas related to abnormal, uncontrollable B cell proliferation or accumulation. For purposes of the present invention, such lymphomas will be referred to according to the *Working Formulation* classification scheme, that is those B cell lymphomas categorized as low grade, intermediate grade, and high grade (see "The Non-Hodgkin's Lymphoma Pathologic Classification Project," *Cancer* 49 (1982):2112-2135). Thus, low-grade B cell lymphomas include small lymphocytic, follicular small-cleaved cell, and follicular mixed small-cleaved and large cell lymphomas; intermediate-grade lymphomas include follicular large cell, diffuse small cleaved cell, diffuse mixed small and large cell, and diffuse large cell lymphomas; and high-grade lymphomas include large cell immunoblastic, lymphoblastic, and small non-cleaved cell lymphomas of the Burkitt's and non-Burkitt's type.

It is recognized that the methods of the invention are useful in identification and the therapeutic treatment of B cell lymphomas that are classified according to the Revised European and American Lymphoma Classification (REAL) system. Such B cell lymphomas include, but are not limited to, lymphomas classified as precursor B cell neoplasms, such as B lymphoblastic leukemia/lymphoma; peripheral B cell neoplasms, including B cell chronic lymphocytic leukemia/small lymphocytic lymphoma, lymphoplasmacytoid lymphoma/immunocytoma, mantle cell lymphoma (MCL), follicle center lymphoma (follicular) (including diffuse small cell, diffuse mixed small and large cell, and diffuse large cell lymphomas), marginal zone B cell lymphoma (including extranodal, nodal, and splenic types), plasmacytoma/myeloma, diffuse large cell B cell lymphoma of the subtype primary mediastinal (thymic), Burkitt's lymphoma, and Burkitt's like high-grade B cell lymphoma; and unclassifiable low-grade or high-grade B cell lymphomas.

These assays can also be used to identify subjects having the pre-malignant condition known as MGUS (monoclonal gammopathy of undetermined significance) who would benefit from treatment with a modulator of CD40L-mediated CD40 signaling. Approximately 25% of patients with MGUS eventually develop multiple myeloma (MM) or a related plasma cell disorder (Kyle (1993) *Mayo Clinic. Proc.* 68:26-36). Proliferation of malignant plasma cells in the bone marrow, detection of a serum or urine monoclonal protein (M protein), anemia, hypercalcemia, renal insufficiency, and lytic bone lesions are clinical manifestations of MM, while MGUS is clinically recognized as the presence of M protein in the serum or urine without other clinical features of MM (see, for example, Kyle and Lust (1989) *Semin. Hematol.* 26:176-200; Greipp and Lust Stem Cells (1995) 13:10-21). MGUS patients are asymptomatic and have stable measurements of M protein (Kyle (1993) *Mayo Clinic. Proc.* 68:26-36). Once MGUS is identified in a subject, maintenance therapy with an appropriate anti-CD40 therapeutic agent, for example, an antagonist anti-CD40 antibody disclosed herein, may block the development of multiple myeloma in these subjects. Thus, the ex vivo prognostic assays disclosed herein can be used to identify subjects with MGUS who would benefit from treatment with an anti-CD40 therapeutic agent. Alternatively, or in addition, the biomarkers, cytokine markers, and CD40-related factors described herein can be used to monitor efficacy of treatment with an anti-CD40 therapeutic agent as noted elsewhere herein.

In particular, the methods of the invention are useful for identifying and treating B cell lymphomas, including those listed above, that are refractory to (i.e., resistant to, or have become resistant to) first-line oncotherapeutic treatments. The term "oncotherapeutic" is intended to mean a treatment for cancer such as chemotherapy, surgery, radiation therapy, single anti-cancer antibody therapy, and combinations thereof. The ex vivo prognostic assays can be used to identify subpopulations of patients for whom treatment intervention with one or more anti-CD40 therapeutic agents that modulates CD40L-mediated CD40 signaling, modulates ADCC, or both is desirable.

The methods of the present invention are also useful for identifying and treating non-B cell related hematological malignancies. Such malignancies include, but are not limited to, acute leukemias; myeloblastic leukemias; acute myelocytic leukemias; promyelocytic leukemia; myelomonocytic leukemia; monocytic leukemia; erythroleukemia; granulocytic leukemia (chronic myelocytic leukemia); polycythemia vera; and the like.

Solid tumors that comprise CD40-expressing neoplastic cells include, but are not limited to, ovarian, lung (for example, non-small cell lung cancer of the squamous cell carcinoma, adenocarcinoma, and large cell carcinoma types, and small cell lung cancer), breast, colon, kidney (including, for example, renal cell carcinomas), bladder, liver (including, for example, hepatocellular carcinomas), gastric, cervical, prostate, nasopharyngeal, thyroid (for example, thyroid papillary carcinoma), skin cancers such as melanoma, and sarcomas, including, for example, osteosarcomas and Ewing's sarcomas.

The term "prognosis" is recognized in the art and encompasses predictions about the likely course of response to therapeutic intervention, and the likely course of disease or disease progression, particularly with respect to likelihood of disease remission, disease relapse, tumor recurrence, metastasis, and death. The ex vivo prognostic assays of the present invention can be used to predict the response of a candidate subject to a particular anti-CD40 therapeutic agent, or class of anti-CD40 therapeutic agents, that modulates CD40L-mediated CD40 signaling, modulates ADCC, or both. By "predicting the response of a candidate subject" is intended assessing the likelihood that a subject in question will experience a positive or negative outcome with a particular anti-CD40 therapeutic agent. For purposes of the present invention, "indicative of a positive treatment outcome" in the context of the ex vivo prognostic assays of the present invention is intended to mean an increased likelihood that the candidate subject will experience beneficial results in response to treatment with the anti-CD40 therapeutic agent under consideration, and thus treatment intervention with that anti-CD40 therapeutic agent would be warranted. In contrast, "indicative of a negative treatment outcome" is intended to mean an increased likelihood that the patient will not benefit from treatment intervention with the anti-CD40 therapeutic agent under consideration, and thus treatment intervention with that anti-CD400 therapeutic agent would not be warranted.

Beneficial results that can be achieved with treatment intervention with anti-CD40 therapeutic agents that modulate CD40L-mediated CD40 signaling include any positive therapeutic response. By "positive therapeutic response" with respect to cancer treatment is intended an improvement in the disease in association with the anti-tumor activity of the anti-CD40 therapeutic agent and/or an improvement in the symptoms associated with the disease of interest. That is, an anti-proliferative effect, the prevention of further tumor outgrowths, a reduction in tumor size, a reduction in the number of cancer cells, and/or a decrease in one or more symptoms mediated by stimulation of CD40-expressing cells can be observed. Thus, for example, a positive therapeutic response would refer to one or more of the following improvements in the disease: (1) a reduction in tumor size; (2) a reduction in the number of cancer (i.e., neoplastic) cells; (3) an increase in neoplastic cell death; (4) inhibition of neoplastic cell survival; (4) inhibition (i.e., slowing to some extent, preferably halting) of tumor growth; (5) inhibition (i.e., slowing to some extent, preferably halting) of cancer cell infiltration into peripheral organs; (6) inhibition (i.e., slowing to some extent, preferably halting) of tumor metastasis; (7) the prevention of further tumor outgrowths; (8) an increased patient survival rate; and (9) some extent of relief from one or more symptoms associated with the cancer. Positive therapeutic responses in any given malignancy can be determined by standardized response criteria specific to that malignancy.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bone scan imaging, endoscopy, and tumor biopsy sampling including bone marrow aspiration (BMA) and counting of tumor cells in the circulation. In addition to these positive therapeutic responses, the subject undergoing therapy with the anti-CD40 therapeutic agent may experience the beneficial effect of an improvement in the symptoms associated with the disease. Thus for B cell tumors, the subject may experience a decrease in the so-called B symptoms, i.e., night sweats, fever, weight loss, and/or urticaria. For pre-malignant conditions, therapy with an anti-CD40 therapeutic agent may block and/or prolong the time before development of a related malignant condition, for example, development of multiple myeloma in subjects suffering from monoclonal gammopathy of undertermined significance (MGUS).

In some embodiments, the ex vivo prognostic assays for use in the methods of the present invention comprise providing a test biological sample and a control biological sample from a candidate subject in need of prognosis for treatment intervention with an anti-CD40 therapeutic agent as noted herein, where the test and control biological samples comprise CD40-expressing neoplastic cells that have been stimulated with a CD40 ligand, either in vivo or ex vivo; contacting the test biological sample with an effective amount of the anti-CD40 therapeutic agent of interest; detecting the level of at least one biomarker in this test biological sample, where the biomarker is selected from the group consisting of a biomarker of cellular apoptosis, a biomarker of a CD40L-mediated CD40 signaling pathway, and a biomarker of cell survival, depending upon the mode of action of the anti-CD40 therapeutic agent of interest; and comparing the level of the biomarker(s) in the test biological sample to the level of the biomarker(s) in the control biological sample, which has not been contacted with the anti-CD40 therapeutic agent. Where the anti-CD40 therapeutic agent is an antagonist that blocks or interferes with CD40L-mediated CD40 signaling, or blocks or interferes with this signaling and also modulates ADCC, the ex vivo prognostic assays disclosed herein for any or all of these biomarkers of cell proliferation and survival, apoptosis, and CD40L-mediated CD40 signaling, can be used to assess the potential beneficial effect of the therapeutic agent, alone or in combination with assays for cytokine markers that are upregulated by CD40L-mediated CD40 signaling, and/or assays for one or more of the CD 40-related factors described herein, in order to identify a subject having a cancer or pre-malignant condition that would be responsive to treatment with that anti-CD40 therapeutic agent. Where the anti-CD40 therapeutic agent has its mode of action via modulating ADCC activity, for example, an anti-CD40 antibody, the ex vivo prognostic assay for one or more markers of apoptosis can be used to assess the potential beneficial effect of the therapeutic agent, alone or in combination with assays for one or more of the CD40-related factors described herein, in order to identify a subject having a cancer or pre-malignant condition that would be responsive to treatment with that anti-CD40 therapeutic agent.

In accordance with the ex vivo prognostic assays of the invention, expression level of one or more biomarkers, and optionally one or more cytokine markers, in a test biological sample that is contacted with the anti-CD40 therapeutic agent of interest is compared to expression level for the biomarker(s), and optionally cytokine marker(s) in a control biological sample. By "test biological sample" is intended a biological sample comprising CD40-expressing neoplastic cells obtained from the candidate subject, and which will be contacted with the anti-CD40 therapeutic agent under consideration for treatment of the candidate subject. By "control biological sample" is intended a biological sample that is comparable to the test biological sample in that it also comprises approximately the same number and kind of CD40-expressing neoplastic cells and has been obtained from the candidate subject in the same timeframe and in a manner equivalent to that used to obtain the test biological sample, and which will be subjected to the same experimental conditions as the test sample, but which will not be contacted with the anti-CD40 therapeutic agent of interest. The test biological sample and control biological sample can be provided from a single biological sample that has been obtained from the subject and divided into subsamples, one of which is designated the test biological sample and another of which is designated the control biological sample. Alternatively, the test biological sample and control biological sample can be provided from two or more biological samples, which can be pooled and then subdivided into subsamples as above, or which can individually represent the test and control biological samples.

While it is recognized that the CD40-expressing neoplastic cells obtained from the candidate subject may have been constitutively stimulated by CD40L in vivo prior to the collection of a biological sample, it is preferable to stimulate the CD40-expressing neoplastic cells of the test and control biological samples ex vivo so that antagonistic effects of an anti-CD40 therapeutic agent on CD40-related activities, for example, stimulation of cell proliferation and CD40 signaling, can effectively be assessed.

In this manner, prior to contacting the test biological sample of CD40-expressing neoplastic cells with the anti-CD40 therapeutic agent of interest, the CD40-expressing neoplastic cells within any given biological sample collected from the candidate subject can be stimulated, for example, with CD40L, to ensure upregulation of CD40 signaling on the CD40-expressing neoplastic cells of the test and control biological samples to be used in the ex vivo prognostic assay.

Any source of CD40L can be used, including, but not limited to, soluble CD40L. Other suitable CD40-stimulatory molecules can include, for example, agonist antibodies that bind specifically to the extracellular domain of CD40. Thus, in some embodiments, suitable CD40-stimulatory molecules include, but are not limited to, membrane-bound CD40L (for example, CD40L bound to the plasma membrane of a cell, for example, formaldehyde-fixed CHO cells transfectant-expressing CD40L; or CD40L incorporated into a synthetic lipid-based substrate such as a liposome or micelle), soluble CD40L, an agonist anti-CD40 antibody, for example, the anti-human CD40 antibody G28-5 (Bristol-Myers Squibb, Seattle, Wash.), and mixtures thereof. An effective amount of a stimulatory molecule to be contacted with cells of a collected biological sample or subsample thereof in order to stimulate one or more CD40 signaling pathways will depend upon factors such as the type of ligand used (e.g., monomeric or multimeric; solubility and permeability, and the like) and the abundance of the CD40 receptor on the CD40-expressing neoplastic cells. Preferably, between about 1.0 mM and about 1 mM of CD40L or soluble CD40L is used to stimulate CD40 signaling.

In some embodiments, CD40-expressing neoplastic cells within the biological sample or subsample thereof are stimulated with soluble recombinant human CD40L (Alexis Corporation, Bingham, Nottinghamshire, UK) prior to the contacting step by incubating the biological sample or subsample thereof with soluble CD40L for a time sufficient to stimulate CD40 signaling. In some embodiments, the incubation time is about 10 minutes to about 4 hours. The amount of soluble CD40L present during the incubation period is readily determined by titration. In one such embodiment, the amount of soluble CD40L is about 1 µg/ml. Any acceptable protocol to contact the test biological sample with an anti-CD40 therapeutic agent of interest can be used in the ex vivo prognostic assays of the invention. Factors to be considered include, but are not limited to, the number of cells to be contacted within a container comprising the test biological sample; the concentration of the anti-CD40 therapeutic agent to be contacted with the test biological sample; the incubation time of the anti-CD40 therapeutic agent with the cells in the test biological sample; where applicable, the concentration of a stimulatory molecule, for example, CD40L, soluble CD40L, or stimulatory fragment or variant thereof, to be contacted with the test biological sample; and, where applicable, the incubation time of the stimulatory molecule with the cells in the test biological sample. Determination of such factors can be accomplished by those skilled in the art based on variables such as the type of biological sample being tested, size of the holding container, the volume of liquid in the container, and the chemical composition of the anti-CD40 therapeutic agent (i.e., size, charge, and the like) being tested.

In one embodiment, a test biological sample or subsample thereof comprising a suitable number of CD40-expressing neoplastic cells is added to a 96-well tissue culture dish. The suitable number of cells is a number of cells that enables one to detect a change in one or more of the CD40-mediated activities (i.e., cell proliferation and cell survival, level of apoptosis, CD40 signaling pathways) using one or more of the detection methods described elsewhere herein. In some embodiments, the suitable number of cells is between about 1 and about $1 \times 10^6$ cells per well of a 96-well tissue culture dish. Following addition of the cells to the tissue culture dish, the cells can be preincubated between about 0 to about 96 hours before contacting the cells with the anti-CD40 therapeutic agent. In some embodiments, the cells are preincubated with a CD40-stimulatory molecule as noted herein above.

An effective amount of an anti-CD40 therapeutic agent is added to the cells of the test biological sample to provide for regulation of a CD40-mediated activity of interest (i.e., CD40L-mediated CD40 signaling, ADCC activity of an agent that binds to CD40, or both) such that the regulation is detectable using one or more detection methods disclosed elsewhere herein. The effective amount will of course be dependent upon the anti-CD40 therapeutic agent being tested. Generally, an effective amount of an anti-CD40 therapeutic agent is between about 1 nM to about 10 mM of the agent per well of a 96-well plate. In one embodiment, the anti-CD40 therapeutic agent is an antagonist anti-CD40 antibody, for example, the CHIR-12.12 or CHIR-5.9 fully human monoclonal antibody, or antigen-binding fragment thereof, and the effective amount is about 0.01 µg/ml to about 30 µg/ml, including about 0.01 µg/ml, 0.1 µg/ml, 0.5 µg/ml, 1 µg/ml, 5 µg/ml, 10 µ/ml, 20 µg/ml, and 30 µg/ml, and other such values between about 0.01 µg/ml and about 30 µg/ml. The cells within the test biological sample or subsample thereof are allowed to incubate for a suitable length of time to allow the anti-CD40 therapeutic agent to interact with the cells and generate one or more biological responses. In some embodiments, the preferred incubation time between the anti-CD40 therapeutic agent and the cells of the test biological sample or subsample thereof is between about 1 minute to about 48 hours. In other embodiments, the incubation time is about 20 minutes, about 30 minutes, about 1 hour, about 4 hours, about 12 hours, about 22 hours, or about 24 hours.

The biological sample(s) that serve(s) as the test and control biological samples can be provided from any collection of cells, tissue, or bodily fluid that comprises neoplastic cells expressing the CD40 antigen. Examples of such biological samples include, but are not limited to, blood, lymph, biopsies, smears, and the like. Biological samples can be collected from a candidate subject using any acceptable procedure in the art, for example, by needle aspiration of bodily fluids, removal of a tissue sample (i.e., biopsy, for example, fine needle aspiration biopsy, core needle biopsy, or excisional biopsy), and the like. Where a biological sample must be stored prior to assay, the biological sample can be transferred to a glass slide prior to assay or may be frozen for later preparation or immediately placed in a fixative solution.

As previously noted, detection of the biomarker of interest at the protein or nucleotide level can be accomplished using any detection method known to those of skill in the art. By "detecting expression" or "detecting the level of" is intended determining the quantity or presence of a biomarker protein or gene in the biological sample. Thus, "detecting expression" encompasses instances where a biomarker is determined not to be expressed, not to be detectably expressed, expressed at a low level, expressed at a normal level, or overexpressed. In order to determine the effect of an anti-CD40 therapeutic agent on CD40L-mediated CD40 signaling, a test biological sample comprising CD40-expressing neoplastic cells that have been stimulated with a CD40 ligand (either in vivo or ex vivo) is contacted with the anti-CD40 therapeutic agent for a sufficient time to allow the therapeutic agent to exert a cellular response, and then expression level of one or more biomarkers of interest in that test biological sample is compared to the expression level in the control biological sample that has not been contacted with the anti-CD40 therapeutic agent. In some embodiments, the control biological sample of neoplastic cells is contacted with a neutral substance or negative control that does not interfere with CD40L-mediated CD40 signaling. For example, in one embodiment, a non-specific immunoglobulin, for example IgG1, that does not bind to CD40 serves as the negative control. Detection can occur over a time course to allow for monitoring of changes in biomarkers over time. Detection can also occur with exposure to different concentrations of the anti-CD40 therapeutic agent to generate a "dose-response" curve for any given biomarker of interest.

Methods for detecting expression of the biomarkers of the invention, and optionally cytokine markers, within the test and control biological samples comprise any methods that determine the quantity or the presence of these markers either at the nucleic acid or protein level. Such methods are well known in the art and include but are not limited to western blots, northern blots, ELISA, immunoprecipitation, immunofluorescence, flow cytometry, immunohistochemistry, nucleic acid hybridization techniques, nucleic acid reverse transcription methods, and nucleic acid amplification methods. In particular embodiments, expression of a biomarker is detected on a protein level using, for example, antibodies that are directed against specific biomarker proteins. These antibodies can be used in various methods such as Western blot, ELISA, multiplexing technologies, immunoprecipitation, or immunohistochemistry techniques. In some embodiments, detection of cytokine markers is accomplished by electrochemiluminescence (ECL). Any of these detection methods for biomarkers and optionally cytokine markers can be combined with assessment of clinical information, conventional prognostic methods, expression of other CD40-related factors, particularly expression of cell-surface CD40 and/or CD40L and circulating levels of soluble CD40 and/or CD40L, and expression of, or presence of, clinically useful prognostic markers known in the art, including, but not limited to, those noted herein above for CLL patients (e.g., ZAP-70, CD38, β2 microglobulin, soluble CD52, and cytogenetic markers, for example, p53 mutational status, ATM mutational status, and chromosome deletions, such as the chromosome 17p deletion and the chromosome 11q deletion. In this manner, the disclosed methods may permit the more accurate determination of candidate subjects whose cancer or pre-malignant condition would benefit from therapeutic intervention with an anti-CD40 therapeutic agent described herein.

Thus, in some embodiments, a candidate subject having a cancer or pre-malignant condition that is associated with CD40-expressing neoplastic cells is tested for responsiveness to an anti-CD40 therapeutic agent of interest using the ex vivo prognostic assays described herein, wherein effects of the therapeutic agent on one or more CD40-mediated activities is assessed. Where further refinement of the ex vivo prognostic assay is desirable, the candidate subject can be examined for the level of expression of, or absence of expression of, one or more CD40-related factors identified herein above, one or more clinically useful prognostic markers, including those identified herein above for CLL patients, or both. In this manner, a biological sample comprising CD40-expressing neoplastic cells can be collected from a candidate subject and assessed for the level of expression of, or absence of expression of, the CD40-related factor(s) and/or clinically useful prognostic marker(s) of interest. Any biological sample comprising CD40-expressing neoplastic cells as noted herein above can be collected for these prognostic assays. Further, any detection method known to those of skill in the art can be used to detect the level of expression, or absence of expression, of the CD40-related factor(s) and/or clinically useful prognostic marker(s) of interest, as noted elsewhere herein.

Where the expression level of one or more CD40-related factors is to be assessed in order to identify a subject having a cancer or pre-malignant condition that will be responsive to treatment with an anti-CD40 therapeutic agent, a biological sample is collected from the subject, and the level of expression in that sample is compared to the level of expression of that factor (or factors) in a control or reference standard. For expression level of cell-surface CD40 and/or cell-surface CD40L, any biological sample comprising CD40-expressing and/or CD40L-expressing neoplastic cells can be used as noted herein above. For circulating levels of sCD40 and/or sCD40L, a blood sample or sample comprising a blood component such as plasma or serum can be obtained from the candidate subject. By "control" or "reference standard" is intended a standard that is of the same biological source (i.e., tissue or bodily fluid) and which distinguishes subjects having the cancer or pre-malignant condition from healthy subjects that are not afflicted with the disease. A skilled artisan can provide a reference standard by taking a measurement of expression levels of these CD40-related factors (i.e., cell-surface CD40, cell-surface CD40L, sCD40, sCD40L) in healthy subjects that do not have the disease and subjects that do have the disease, controlling for age, sex, race, and the like, and comparing the expression levels to determine the standard level of expression to be expected in a healthy subject. In some embodiments, the expression level in the candidate subject having the cancer or pre-malignant condition is at least 20%, 30%, 40%, 50%, 60%, 70%, 80%, 100%, 150%, 200%, 250%, 300% greater than the expression level in the reference standard. It is recognized that the applicability of treatment with an anti-CD40 therapeutic agent can be assessed by detecting the level of expression of one or more of these CD40-related factors, wherein an increased level of expression in a biological sample relative to the reference standard is sufficient to establish that the subject has a cancer or pre-malignant condition that will be responsive to treatment with the anti-CD40 therapeutic agent of interest without having to do additional screening for ex vivo effects of the anti-CD40 therapeutic agent on CD40-mediated activities such as cell survival and proliferation, and/or ADCC activity.

The present invention also encompasses kits for carrying out the ex vivo prognostic assays of the present invention. For example, the kit can comprise a labeled compound or agent capable of detecting a biomarker described herein, e.g., a biomarker of apoptosis, cellular proliferation or survival, or a CD40L-mediated CD40 signaling pathway, either at the protein or nucleic acid level, in a biological sample and means for determining the amount of the biomarker in the sample (for example, an antibody or an oligonucleotide probe that binds to RNA encoding a biomarker of interest) following incubation of the sample with an anti-CD40 therapeutic agent of interest. Kits can be packaged to allow for detection of multiple biomarkers of interest by including individual labeled compounds or agents capable of detecting each individual biomarker of interest and means for determining the amount of each biomarker in the sample.

Kits can also include instructions for treating a subject when the ex vivo prognostic assay generates a result that is indicative of a positive treatment outcome with the anti-CD40 therapeutic agent.

For antibody-based kits, the kit can comprise, for example: (1) a first antibody (e.g., attached to a solid support) that binds to a biomarker of interest; and, optionally, (2) a second, different antibody that binds to the biomarker or the first antibody and is conjugated to a detectable agent. For oligonucleotide-based kits, the kit can comprise, for example: (1) an oligonucleotide, e.g., a detectably labeled oligonucleotide, that hybridizes to a nucleic acid sequence encoding the biomarker or (2) a pair of primers useful for amplifying a nucleic acid molecule encoding the biomarker of interest. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is a candidate for treatment with the anti-CD40 therapeutic agent.

Detection Methods

Any means for specifically identifying and quantifying a biomarker, cytokine marker, or CD40-related factor protein of interest (for example, a biomarker of cell survival or proliferation, a biomarker of apoptosis, a biomarker of a CD40L-mediated CD40 signaling pathway, circulating soluble CD40 or CD40L, cell-surface CD40 or CD40L, or a clinically useful prognostic marker, for example, ZAP-70, CD38, and β2 microglobulin for a CLL patient) in the biological sample of a candidate subject is contemplated. Thus, in some embodiments, expression level of a biomarker protein of interest in a biological sample is detected by means of a binding protein capable of interacting specifically with that biomarker protein or a biologically active variant thereof. Preferably, labeled antibodies, binding portions thereof, or other binding partners may be used. The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable.

The antibodies for detection of a biomarker protein may be monoclonal or polyclonal in origin, or may be synthetically or recombinantly produced. The amount of complexed protein, for example, the amount of biomarker protein associated with the binding protein, for example, an antibody that specifically binds to the biomarker protein, is determined using standard protein detection methodologies known to those of skill in the art. A detailed review of immunological assay design, theory and protocols can be found in numerous texts in the art (see, for example, Ausubel et al., eds. (1995) *Current Protocols in Molecular Biology*) (Greene Publishing and Wiley-Interscience, NY)); Coligan et al., eds. (1994) *Current Protocols in Immunology* (John Wiley & Sons, Inc., New York, N.Y.).

A variety of assays are available for detecting proteins with labeled antibodies. In a one-step assay, the target protein of interest to be detected, if it is present, is immobilized and incubated with a labeled antibody. The labeled antibody binds to the immobilized target protein molecule. After washing to remove unbound molecules, the sample is assayed for the presence of the label. In a standard format, a single protein is assayed per sample. Using newer multiplex technologies, multiple proteins can be assayed in a single sample by using different labels for each detecting antibody.

In a two-step assay, the immobilized target protein molecule of interest is incubated with an unlabeled antibody. The target protein-unlabeled antibody complex, if present, is then bound to a second, labeled antibody that is specific for the unlabeled antibody. The sample is washed and assayed for the presence of the label.

The choice of marker used to label the antibodies will vary depending upon the application. However, the choice of the marker is readily determinable to one skilled in the art. These labeled antibodies may be used in immunoassays as well as in histological applications to detect the presence of any biomarker or protein of interest. The labeled antibodies may be polyclonal or monoclonal. Further, the antibodies for use in detecting a protein of interest may be labeled with a radioactive atom, an enzyme, a chromophoric or fluorescent moiety, or a colorimetric tag as described elsewhere herein. The choice of tagging label also will depend on the detection limitations desired. Enzyme assays (ELISAs) typically allow detection of a colored product formed by interaction of the enzyme-tagged complex with an enzyme substrate. Radionuclides that can serve as detectable labels include, for example, I-131, I-123, I-125, Y-90, Re-188, Re-186, At-211, Cu-67, Bi-212, and Pd-109. Examples of enzymes that can serve as detectable labels include, but are not limited to, horseradish peroxidase, alkaline phosphatase, beta-galactosidase, and glucose-6-phosphate dehydrogenase. Chromophoric moieties include, but are not limited to, fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Examples of suitable ligand-receptor pairs are biotin-avidin or biotin-streptavidin, and antibody-antigen.

In some embodiments, the present invention contemplates the use of a sandwich technique for detecting one or more biomarkers, or other proteins of interest as noted herein above, in serum and other biological fluids. As described in International Publication No. WO 93/09437, such a technique uses two antibodies capable of binding the protein of interest: e.g., one of which is free in solution but labeled with a detectable chemical compound, the other of which is immobilized onto a solid support. Examples of chemical labels that may be used for the second antibody include but are not limited to radioisotopes, fluorescent compounds, and enzymes or other molecules that generate colored or electrochemically active products when exposed to a reactant or enzyme substrate. When samples containing the biomarker or other protein of interest are placed in this system, the biomarker or other protein of interest binds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Biological samples can be screened individually; alternatively, numerous samples of biological fluids can be screened at the same time, for example, using the conventional 96-well microtiter format, which is widely used and easily automatable. There are also several commercially available spectrometers ("plate readers") for calorimetrically analyzing 96-well plates. Further, biological samples can be screened for one biomarker, or multiple markers, for example, a panel of biomarkers, using methods well known in the art.

In preferred embodiments, expression of one or more biomarkers or other proteins of interest within a biological sample, for example, a sample of bodily fluid, is detected by radioimmunoassays or enzyme-linked immunoassays (ELISAs), competitive binding enzyme-linked immunoassays, dot blot (see, for example, *Promega Protocols and Applications Guide* ($2^{nd}$ ed.; Promega Corporation (1991), Western blot (see, for example, Sambrook et al. (1989) *Molecular Cloning, A Laboratory Manual*, Vol. 3, Chapter 18 (Cold Spring Harbor Laboratory Press, Plainview, N.Y.), chromatography, preferably high performance liquid chromatography (HPLC), or other assays known in the art. Thus, the detection assays can involve steps such as, but not limited to, immunoblotting, immunodiffusion, immunoelectrophoresis, or immunoprecipitation.

For any given protein detection assay, the biological sample, or a subsample thereof comprising CD40-expressing neoplastic cells, is contacted with the binding partner, for example, the antibody, or detectably labeled antibody, for the biomarker or other protein of interest, for a time sufficient to permit the formation of antibody-antigen complexes, and then antibody binding is detected, for example, by any means noted herein above. Antibodies and detectably labeled antibodies to the biomarkers, CD40-related factors, and clinically useful prognostic markers described herein are well known in the art and commercially available. See, for example, antibodies specific to biomarkers of apoptosis, cell survival, and CD40 signaling pathways, as well as clinically useful prognostic markers such as ZAP-70 and p53 available, for example, from Cell Signaling Technology, Beverly, Mass.; DAKO, Copenhagen, Denmark; and the like. Alternatively, antibodies, or detectably labeled forms of these antibodies, can be generated using antibody production methods well known in the art, and further described herein below.

A number of assay kits for biomarkers of caspases are commercially available. For example, the Homogeneous Caspases Assay (Roche Applied Sciences, Indianapolis, Ind.), is a fluorimetric assay for the quantitative in vitro determination of caspase activity in microplates. The assay is particularly useful for high-throughput screening, allowing, for example, for 100 tests on 96-well plates, and 400 tests on 384-well plates (Cat. No. 3 005 372). This assay allows for detection of several caspases, including Caspase-2, Caspase-3, Caspase-7, and to a lesser extent, Caspase-6, Caspase-8, Caspase-9, and Caspase-10, in biological samples, including, for example, serum or plasma. The Cell Death Detection ELISA$^{PLUS}$ assay (Cat. No. 1 774 425; Roche Applied Sciences, Indianapolis, Ind.) is based on a quantitative sandwich-enzyme-immunoassay principle, using mouse monoclonal antibodies directed against DNA and histones, respectively. This assay allows the specific detection and quantitation of mono- and oligonucleosomes that are released into the cytoplasm of cells that die from apoptosis. It can be used for a variety of samples, including cell lysates, serum, culture supernatant, and the like.

Cell surface PS can be detected using any of the commercially available Annexin V staining reagents, which are based on the high affinity of annexin V for PS. See, for example, the Annexin V staining reagents commercially available from Roche Applied Science. By conjugating FITC to Annexin V it is possible to identify and quantitate apoptotic cells on a single-cell basis by flow cytometry. Staining cells simultaneously with FITC-Annexin V (green fluorescence) and the non-vital dye propidium iodide (red fluorescence) can provide for the discrimination of intact cells (FITC–PI–), early apoptotic (FITC+PI–), and late apoptotic or necrotic cells (FITC+PI+).

Further, elevated apoptosis within a biological sample can be confirmed with nucleic acid-based methods that detect the DNA fragmentation that is characteristic of apoptosis. When resolved using electrophoresis on agarose gels, apoptotic DNA initially has a characteristic "ladder" pattern, as opposed to a smear of nucleic acids that is observed, for example, in necrosis or other non-specific DNA degradation. A common histochemical technique to detect DNA fragmentation uses end-labeled DNA. Kits for such are commercially available, such as the APOLERT™ DNA fragmentation kit (Clontech Laboratories, Inc., Palo Alto, Calif.). This assay is based on terminal deoxynucleotidyltransferase (Tdt)-mediated dUTP nick-end labeling (TUNEL), where Tdt catalyzes the incorporation of fluorescein-dUTP at the free 3'-hydroxyl ends of fragmented DNA in cells undergoing apoptosis.

Any method known in the art can be used to detect production of cytokine markers. Standard assays comprise an ELISA format, where one cytokine is measured per sample. Alternatively, a more sensitive technology is electrochemiluminescence (ECL). In one embodiment, cytokine production is assayed using ECL, for example, using a multi-array system such as the commercially available Meso Scale Discovery® system for high performance cytokine assays (Meso Scale Discovery, Gaithersburg, Md.). Other formats that allow for measuring multiple cytokines (or other analytes) at once within a sample include the multiplex technologies. One such product is the Luminex® bead technology (Luminex Corporation, Austin, Tex.), in which up to 100 color-coded microspheres coated with reagents specific to a particular bioassay (such as an antibody to a cytokine) can be mixed together and analyzed using lasar technology.

The presence of one or more of the biomarkers, cytokines, CD40-related factors, and clinically useful prognostic markers described herein within a biological sample obtained from a candidate subject may also be determined at the nucleic acid level. Nucleic acid-based techniques for assessing expression are well known in the art and include, for example, determining the level of biomarker mRNA in a biological sample. Many expression detection methods use isolated RNA. Any RNA isolation technique that does not select against the isolation of mRNA can be utilized for the purification of RNA (see, e.g., Ausubel et al., ed. (1987-1999) *Current Protocols in Molecular Biology* (John Wiley & Sons, New York). Additionally, large numbers of tissue samples can readily be processed using techniques well known to those of skill in the art, such as, for example, the single-step RNA isolation process disclosed in U.S. Pat. No. 4,843,155.

Thus, in some embodiments, the detection of a biomarker or other protein of interest is assayed at the nucleic acid level using nucleic acid probes. The term "nucleic acid probe" refers to any molecule that is capable of selectively binding to a specifically intended target nucleic acid molecule, for example, a nucleotide transcript. Probes can be synthesized by one of skill in the art, or derived from appropriate biological preparations. Probes may be specifically designed to be labeled, for example, with a radioactive label, a fluorescent label, an enzyme, a chemiluminescent tag, a colorimetric tag, or other labels or tags that are discussed above or that are known in the art. Examples of molecules that can be utilized as probes include, but are not limited to, RNA and DNA.

For example, isolated mRNA can be used in hybridization or amplification assays that include, but are not limited to, Southern or Northern analyses, polymerase chain reaction analyses and probe arrays. One method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a biomarker, CD40-related factor, or clinically useful prognostic marker described herein above. Hybridization of an mRNA with the probe indicates that the biomarker or other target protein of interest is being expressed.

In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in a gene chip array. A skilled artisan can readily adapt known mRNA detection methods for use in detecting the level of mRNA encoding the biomarkers or other proteins of interest.

An alternative method for determining the level of a mRNA of interest in a sample involves the process of nucleic acid amplification, e.g., by RT-PCR (see, for example, U.S. Pat. No. 4,683,202), ligase chain reaction (Barany (1991) *Proc. Natl. Acad. Sci. USA* 88:189-193), self-sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, biomarker expression, or expression of a CD40-related factor or other clinically useful prognostic marker, is assessed by quantitative fluorogenic RT-PCR (i.e., the TaqMan® System).

Expression levels of an RNA of interest may be monitored using a membrane blot (such as used in hybridization analysis such as Northern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The detection of expression may also comprise using nucleic acid probes in solution.

In one embodiment of the invention, microarrays are used to detect expression of one or more biomarkers, CD40-related factors, and/or clinically useful prognostic markers. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning. Hybridization intensities for each probe on the array are determined and converted to a quantitative value representing relative gene expression levels. See, U.S. Pat. Nos. 6,040,138, 5,800,992 and 6,020,135, 6,033,860, and 6,344,316, which are incorporated herein by reference. High-density oligonucleotide arrays are particularly useful for determining the gene expression profile for a large number of RNA's in a sample.

Techniques for the synthesis of these arrays using mechanical synthesis methods are described in, e.g., U.S. Pat. No. 5,384,261, incorporated herein by reference in its entirety. Although a planar array surface is preferred, the array may be fabricated on a surface of virtually any shape or even a multiplicity of surfaces. Arrays may be peptides or nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, each of which is hereby incorporated in its entirety for all purposes. Arrays may be packaged in such a manner as to allow for diagnostics or other manipulation of an all-inclusive device. See, for example, U.S. Pat. Nos. 5,856,174 and 5,922,591, herein incorporated by reference.

In one approach, total mRNA isolated from the sample is converted to labeled cRNA and then hybridized to an oligonucleotide array. Each sample is hybridized to a separate array. Relative transcript levels may be calculated by reference to appropriate controls present on the array and in the sample.

Anti-CD40 Therapeutic Agents

The ex vivo prognostic assays described herein can be used to identify subjects having a cancer or pre-malignant condition associated with CD40-expressing neoplastic cells who would benefit from treatment with any anti-CD40 therapeutic agent of interest. Of particular interest are anti-CD40 therapeutic agents that modulate CD40L-mediated CD40 signaling and/or modulate ADCC. Such anti-CD40 therapeutic agents include, but are not limited to, antagonist anti-CD40 antibodies that block or interfere with CD40L-mediated signaling and/or modulate ADCC activity when bound to CD40, CD40L antagonists, including anti-CD40L antibodies, mutated forms of CD40L that can bind to CD40 but which do not trigger CD40 signaling, soluble CD40, soluble forms of fusion proteins comprising CD40, and pharmacologic agents that disrupt or interfere with CD40L-CD40 interaction and/or interfere with CD40 signaling, for example, the CD40:CD40L binding interruptor compounds disclosed in U.S. Patent Application Publication No. 20040067982, herein incorporated by reference in its entirety. Of particular interest are antagonist anti-CD40 therapeutic agents, for example, antagonist anti-CD40 antibodies and antagonist anti-CD40L antibodies, or antigen-binding fragments thereof that serve to block CD40L-mediated CD40 signaling, and anti-CD40 therapeutic agents that modulate ADCC, for example, anti-CD40 antibodies and antigen-binding fragments thereof.

Anti-CD40 Antibodies.

Monoclonal antibodies to CD40 are known in the art. See, for example, the sections dedicated to B-cell antigen in McMichael, ed. (1987; 1989) *Leukocyte Typing III and IV* (Oxford University Press, New York); U.S. Pat. Nos. 5,674,492; 5,874,082; 5,677,165; 6,056,959; WO 00/63395; International Publication Nos. WO 02/28905 and WO 02/28904; Gordon et al. (1988) *J Immunol.* 140:1425; Valle et al. (1989) *Eur. J. Immunol.* 19:1463; Clark et al. (1986) *PNAS* 83:4494; Paulie et al. (1989) *J. Immunol.* 142:590; Gordon et al. (1987) *Eur. J. Immunol.* 17:1535; Jabara et al. (1990) *J. Exp. Med.* 172:1861; Zhang et al. (1991) *J Immunol.* 146:1836; Gascan et al. (1991) *J. Immunol.* 147:8; Banchereau et al. (1991) *Clin. Immunol. Spectrum* 3:8; and Banchereau et al. (1991) *Science* 251:70; all of which are herein incorporated by reference. Other anti-CD40 monoclonal antibodies include, but are not limited to, humanized anti-CD40 antibodies, such as SGN-40 (Tai et al. (2004) *Cancer Res.* 64:2846-52; U.S. Pat. No. 6,838,261), which is the humanized form of the murine anti-CD40 antibody SGN-14 (Francisco et al. (2000) *Cancer Res.* 60:3225-31), and the agonist and antagonist antibodies disclosed in U.S. Patent Application Publication No. 2004/0120948; herein incorporated by reference in their entirety.

In one embodiment, the ex vivo prognostic assays are used to examine suitability or efficacy of treatment with antagonist anti-CD40 antibodies. Antagonist anti-CD40 antibodies for use in the methods of the invention include monoclonal antibodies or antigen-binding fragments thereof that are capable of specifically binding to human CD40 antigen expressed on the surface of a human cell. In some embodiments, antagonist anti-CD40 antibodies for use in the methods of the present invention exhibit a strong single-site binding affinity for the CD40 cell-surface antigen. Such monoclonal antibodies exhibit a dissociation equilibrium constant ($K_D$) for CD40 of at least $10^{-5}$ M, at least $3 \times 10^{-5}$ M, preferably at least $10^{-6}$ M to $10^{-7}$ M, more preferably at least $10^{-8}$ M to about $10^{-12}$ M, measured using a standard assay such as Biacore™. Biacore analysis is known in the art and details are provided in the "BIAapplications handbook." Methods described in WO 01/27160 can be used to modulate the binding affinity.

Of particular interest are antagonist anti-CD40 antibodies that are free of significant agonist activity as defined herein above but exhibit antagonist activity when bound to CD40 antigen on human cells, particularly when bound to CD40 antigen on neoplastic human B cells. In one embodiment of the invention, the antagonist anti-CD40 antibody is free of significant agonist activity in one B cell response. In another embodiment of the invention, the antagonist anti-CD40 antibody is free of significant agonist activity in assays of more than one B cell response (e.g., proliferation and differentiation, or proliferation, differentiation, and antibody production). Suitable monoclonal anti-CD40 antibodies have human constant regions; preferably they also have wholly or partially humanized framework regions; and most preferably are fully human antibodies or antigen-binding fragments thereof. Examples of such monoclonal antibodies are the antibodies designated herein as CHIR-5.9 and CHIR-12.12.

The monoclonal antibodies CHIR-5.9 and CHIR-12.12 represent antagonist anti-CD40 antibodies for use in the methods of the present invention. The CHIR-5.9 and CHIR-12.12 antibodies are fully human anti-CD40 monoclonal antibodies of the $IgG_1$ isotype produced from the hybridoma cell lines 131.2F8.5.9 (referred to herein as the cell line 5.9) and 153.8E2.D10.D6.12.12 (referred to herein as the cell line 12.12). These cell lines were created using splenocytes from immunized xenotypic mice containing the human $IgG_1$ heavy chain locus and the human κ chain locus (XenoMouse® technology; Abgenix; Fremont, Calif.). The spleen cells were fused with the mouse myeloma SP2/0 cells (Sierra Bio-Source). The resulting hybridomas were sub-cloned several times to create the stable monoclonal cell lines 5.9 and 12.12. Other antibodies of the invention may be prepared similarly using mice transgenic for human immunoglobulin loci or by other methods known in the art and/or described herein.

The nucleotide and amino acid sequences of the variable regions of the CHIR-12.12 antibody, and the amino acid sequences of the variable regions of the CHIR-5.9 antibody, are disclosed. More particularly, the amino acid sequences for the leader, variable, and constant regions for the light chain and heavy chain for mAb CHIR-12.12 are set forth in SEQ ID NO:2 (complete sequence for the light chain of mAb CHIR-12.12), SEQ ID NO:4 (complete sequence for the heavy chain for mAb CHIR-12.12), and SEQ ID NO:5 (complete sequence for a variant of the heavy chain for mAb CHIR-12.12 set forth in SEQ ID NO:4, where the variant comprises a serine substitution for the alanine residue at position 153 of SEQ ID NO:4). The nucleotide sequences encoding the light chain and heavy chain for mAb CHIR-12.12 are set forth in SEQ ID NO:1 (coding sequence for the light chain for mAb CHIR-12.12) and SEQ ID NO:3 (coding sequence for the heavy chain for mAb CHIR-12.12). The amino acid sequences for the leader, variable, and constant regions for the light chain and heavy chain of the CHIR-5.9 mAb are set forth in SEQ ID NO:6 (complete sequence for the light chain of mAb CHIR-5.9), SEQ ID NO:7 (complete sequence for the heavy chain of mAb CHIR-5.9), and SEQ ID NO:8 (complete sequence for a variant of the heavy chain of mAb CHIR-5.9 set forth in SEQ ID NO:7, where the variant comprises a serine substitution for the alanine residue at position 158 of SEQ ID NO:7). Further, hybridomas expressing CHIR-5.9 and CHIR-12.12 antibodies have been deposited with the ATCC with a patent deposit designation of PTA-5542 and PTA-5543, respectively.

In addition to antagonist activity, anti-CD40 antibodies for use in the methods of the present invention can have another mechanism of action against a tumor cell. For example, native CHIR-5.9 and CHIR-12.12 antibodies have ADCC activity. Alternatively, the variable regions of the CHIR-5.9 and CHIR-12.12 antibodies can be expressed on another antibody isotype that has ADCC activity. It is also possible to conjugate native forms, recombinant forms, or antigen-binding fragments of CHIR-5.9 or CHIR-12.12 to a cytotoxin, a therapeutic agent, or a radioactive metal ion or radioisotope, as noted herein below.

The CHIR-5.9 and CHIR-12.12 monoclonal antibodies bind soluble CD40 in ELISA-type assays, prevent the binding of CD40-ligand to cell-surface CD40, and displace the pre-bound CD40-ligand, as determined by flow cytometric assays. Antibodies CHIR-5.9 and CHIR-12.12 compete with each other for binding to CD40 but not with 15B8, the anti-CD40 monoclonal antibody described in U.S. Provisional Application Ser. No. 60/237,556, titled "Hunan Anti-CD40 Antibodies," filed Oct. 2, 2000, and PCT International Application No. PCT/US01/30857, also titled "Human Anti-CD40 Antibodies," filed Oct. 2, 2001, both of which are herein incorporated by reference in their entirety. When tested in vitro for effects on proliferation of B cells from normal human subjects, CHIR-5.9 and CHIR-12.12 act as antagonist anti-CD40 antibodies. Furthermore, CHIR-5.9 and CHIR-12.12 do not induce strong proliferation of human lymphocytes from normal subjects. These antibodies are able to kill CD40-expressing target cells by antibody dependent cellular cytotoxicity (ADCC). The binding affinity of CHIR-5.9 for human CD40 is $1.2 \times 10^{-8}$ M and the binding affinity of CHIR-12.12 is $5 \times 10^{-10}$ M, as determined by the Biacore™ assay.

Other antagonist anti-CD40 antibodies that share the binding characteristics of the monoclonal antibodies CHIR-5.9 and CHIR-12.12 described above include, but are not limited to the following: (1) the monoclonal antibodies produced by the hybridoma cell lines designated 131.2F8.5.9 (referred to herein as the cell line 5.9) and 153.8E2.D10.D6.12.12 (referred to herein as the cell line 12.12), deposited with the ATCC as Patent Deposit No. PTA-5542 and Patent Deposit No. PTA-5543, respectively; (2) a monoclonal antibody comprising an amino acid sequence selected from the group consisting of the sequence shown in SEQ ID NO:2, the sequence shown in SEQ ID NO:4, the sequence shown in SEQ ID NO:5, both the sequences shown in SEQ ID NO:2 and SEQ ID NO:4, and both the sequences shown in SEQ ID NO:2 and SEQ ID NO:5; (3) a monoclonal antibody comprising an amino acid sequence selected from the group consisting of the sequence shown in SEQ ID NO:6, the sequence shown in SEQ ID NO:7, the sequence shown in SEQ ID NO:8, both the sequences shown in SEQ ID NO:6 and SEQ ID NO:7, and both the sequences shown in SEQ ID NO:6 and SEQ ID NO:8; (4) a monoclonal antibody having an amino acid sequence encoded by a nucleic acid molecule comprising a nucleotide sequence selected from the group consisting of the nucleotide sequence shown in SEQ ID NO: 1, the nucleotide sequence shown in SEQ ID NO:3, and both the sequences shown in SEQ ID NO:1 and SEQ ID NO:3; (5) a monoclonal antibody that binds to an epitope capable of binding the monoclonal antibody produced by the hybridoma cell line 5.9 or the hybridoma cell line 12.12; (6) a monoclonal antibody that binds to an epitope comprising residues 82-87 of the amino acid sequence shown in SEQ ID NO: 10 or SEQ ID NO:12; (7) a monoclonal antibody that competes with the monoclonal antibody CHIR-5.9 or CHIR-12.12 in a competitive binding assay; and (8) a monoclonal antibody that is an antigen-binding fragment of the CHIR-12.12 or CHIR-5.9 monoclonal antibody or the foregoing monoclonal antibodies in preceding items (1)-(7), where the fragment retains the capability of specifically binding to the human CD40 antigen.

Those skilled in the art recognize that the antibodies and antigen-binding fragments of these antibodies described herein include antibodies and antigen-binding fragments thereof that are produced recombinantly using methods well known in the art and described herein below, and include, for example, monoclonal antibodies CHIR-5.9 and CHIR-12.12 that have been recombinantly produced.

Additional antagonist anti-CD40 antibodies include the monoclonal antibodies referred to as 5D12, 3A8 and 3C6, which are secreted by a hybridoma having ATCC accession numbers HB 11339, HB 12024 and HB 11340, respectively. See, for example, U.S. Pat. No. 6,315,998, herein incorporated by reference in its entirety.

Other antagonist anti-CD40 antibodies are known in the art. See, for example, the human anti-CD40 antibody produced by the hybridoma designated F4-465 disclosed in U.S. Patent Application Publication Nos. 20020142358 and 20030059427; herein incorporated by reference in their entirety. F4-465 was obtained from the HAC mouse (Kuroiwa et al. (2000) *Nature Biotech.* 10:1086 (2000)) and therefore expresses the human lambda light chain.

Antagonist Anti-CD40L Antibodies.

Antibodies that bind to CD40L and thereby interfere with CD40/CD40L interaction or CD40L-mediated CD40 signaling are known in the art. Examples include, but are not limited to, those disclosed in International Patent Publication WO 95/06666, the content of which is herein by reference in its entirety. Specific examples include, but are not limited to antagonist anti-CD40L antibodies designated 89-76 and 24-31, which are produced by the 89-76 and 24-31 hybridomas, respectively, deposited with the American Type Culture Collection (ATCC), 10801 University Blvd., Manassas, Va. 20110-2209, and assigned ATCC Accession Number HB11713 and HB11712, respectively.

Production of Antibodies

The antibodies for use in the methods of the present invention, for example, the antagonist anti-CD40 antibodies disclosed herein and any antibody that specifically binds to a biomarker or other clinically useful prognostic marker of interest, can be produced using any antibody production method known to those of skill in the art. Thus, polyclonal sera may be prepared by conventional methods. In general, a solution containing the antigen of interest, for example, the CD40 antigen or CD40L antigen, is first used to immunize a suitable animal, preferably a mouse, rat, rabbit, or goat. Rabbits or goats are preferred for the preparation of polyclonal sera due to the volume of serum obtainable, and the availability of labeled anti-rabbit and anti-goat antibodies.

Polyclonal sera can be prepared in a transgenic animal, preferably a mouse bearing human immunoglobulin loci. In a preferred embodiment, Sf9 cells expressing the protein of interest, for example, CD40 or CD40L, are used as the immunogen. Immunization can also be performed by mixing or emulsifying the antigen-containing solution in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera are obtained by bleeding the immunized animal into a glass or plastic container, incubating the blood at 25° C. for one hour, followed by incubating at 4° C. for 2-18 hours. The serum is recovered by centrifugation (e.g., 1,000×g for 10 minutes). About 20-50 ml per bleed may be obtained from rabbits.

Production of the Sf 9 (*Spodoptera frugiperda*) cells is disclosed in U.S. Pat. No. 6,004,552, incorporated herein by reference. In the case of CD40, briefly, sequences encoding human CD40 were recombined into a baculovirus using transfer vectors. The plasmids were co-transfected with wild-type baculovirus DNA into Sf9 cells. Recombinant baculovirus-infected Sf9 cells were identified and clonally purified.

Preferably the antibody is monoclonal in nature. By "monoclonal antibody" is intended an antibody obtained from a population of substantially homogeneous antibodies, i.e., the individual antibodies comprising the population are identical except for possible naturally occurring mutations that may be present in minor amounts. The term is not limited regarding the species or source of the antibody. The term encompasses whole immunoglobulins as well as fragments such as Fab, F(ab')2, Fv, and others which retain the antigen binding function of the antibody. Monoclonal antibodies are highly specific, being directed against a single antigenic site; for example, in the case of anti-CD40 antibodies or anti-CD40L antibodies, the CD40 cell surface antigen or CD40L cell surface antigen, respectively. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in, for example, Clackson et al. (1991) *Nature* 352:624-628; Marks et al. (1991) *J. Mol. Biol.* 222: 581-597; and U.S. Pat. No. 5,514,548.

By "epitope" is intended the part of an antigenic molecule to which an antibody is produced and to which the antibody will bind. Epitopes can comprise linear amino acid residues (i.e., residues within the epitope are arranged sequentially one after another in a linear fashion), nonlinear amino acid residues (referred to herein as "nonlinear epitopes"; these epitopes are not arranged sequentially), or both linear and nonlinear amino acid residues.

Monoclonal antibodies can be prepared using the method of Kohler et al. (1975) *Nature* 256:495-496, or a modification thereof. Typically, a mouse is immunized with a solution containing an antigen. Immunization can be performed by mixing or emulsifying the antigen-containing solution in saline, preferably in an adjuvant such as Freund's complete adjuvant, and injecting the mixture or emulsion parenterally. Any method of immunization known in the art may be used to obtain the monoclonal antibodies of the invention. After immunization of the animal, the spleen (and optionally, several large lymph nodes) are removed and dissociated into single cells. The spleen cells may be screened by applying a cell suspension to a plate or well coated with the antigen of interest. The B cells expressing membrane bound immunoglobulin specific for the antigen bind to the plate and are not rinsed away. Resulting B cells, or all dissociated spleen cells, are then induced to fuse with myeloma cells to form hybridomas, and are cultured in a selective medium. The resulting cells are plated by serial dilution and are assayed for the production of antibodies that specifically bind the antigen of interest (and that do not bind to unrelated antigens). The selected monoclonal antibody (mAb)-secreting hybridomas are then cultured either in vitro (e.g., in tissue culture bottles or hollow fiber reactors), or in vivo (as ascites in mice).

Where antibodies for use in the methods of the invention, for example, antagonist anti-CD40 antibodies or antagonist anti-CD40L antibodies, are to be prepared using recombinant DNA methods, the DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al. (1993) *Curr. Opinion in Immunol.* 5:256 and Phickthun (1992) *Immunol. Revs.* 130:151. Alternatively, antibody can be produced in a cell line such as a CHO cell line, as disclosed in U.S. Pat. Nos. 5,545,403; 5,545,405; and 5,998,144; incorporated herein by reference. Briefly the cell line is transfected with vectors capable of expressing a light chain and a heavy chain, respectively. By transfecting the two proteins on separate vectors, chimeric antibodies can be produced. Another advantage is the correct glycosylation of the antibody.

In some embodiments, the antagonist anti-CD40 antibody, for example, the CHIR-12.12 or CHIR-5.9 antibody, or antigen-binding fragment thereof is produced in CHO cells using the GS gene expression system (Lonza Biologics, Portsmouth, N.H.), which uses glutamine synthetase as a marker. See, also U.S. Pat. Nos. 5,122,464; 5,591,639; 5,658,759; 5,770,359; 5,827,739; 5,879,936; 5,891,693; and 5,981,216; the contents of which are herein incorporated by reference in their entirety.

Additionally, antibodies for use in the methods of the invention can be chimeric antibodies that have the desired binding characteristics. Thus, for example, chimeric anti-CD40 antibodies for use in the methods of the invention could have the binding characteristics of the CHIR-5.9 and CHIR-12.12 monoclonal antibodies described herein. By "chimeric" antibodies is intended antibodies that are most preferably derived using recombinant deoxyribonucleic acid techniques and which comprise both human (including immunologically "related" species, e.g., chimpanzee) and non-human components. Thus, the constant region of the chimeric antibody is most preferably substantially identical to the constant region of a natural human antibody; the variable region of the chimeric antibody is most preferably derived from a non-human source and has the desired antigenic specificity to the antigen of interest, for example, CD40 or CD40L antigen. The non-human source can be any vertebrate source that can be used to generate antibodies to a human antigen or material comprising a human CD40 antigen. Such non-human sources include, but are not limited to, rodents (e.g., rabbit, rat, mouse, etc.; see, for example, U.S. Pat. No. 4,816,567, herein incorporated by reference) and non-human primates (e.g., Old World Monkey, Ape, etc.; see, for example, U.S. Pat. Nos. 5,750,105 and 5,756,096; herein incorporated by reference). As used herein, the phrase "immunologically active" when used in reference, for example, to chimeric anti-CD40 antibodies or chimeric anti-CD40L antibodies, means a chimeric antibody that binds human CD40 or human CD40L, respectively.

By "humanized" is intended forms of antibodies that contain minimal sequence derived from non-human immunoglobulin sequences. For the most part, humanized antibodies are human immunoglobulins (recipient antibody) in which residues from a hypervariable region (also known as complementarity determining region or CDR) of the recipient are replaced by residues from a hypervariable region of a non-human species (donor antibody) such as mouse, rat, rabbit, or nonhuman primate having the desired specificity, affinity, and capacity. The phrase "complementarity determining region" refers to amino acid sequences which together define the binding affinity and specificity of the natural Fv region of a native immunoglobulin binding site. See, e.g., Chothia et al (1987) *J. Mol. Biol.* 196:901-917; Kabat et al (1991) U.S. Dept. of Health and Human Services, NIH Publication No. 91-3242). The phrase "constant region" refers to the portion of the antibody molecule that confers effector functions. In previous work directed towards producing non-immunogenic antibodies for use in therapy of human disease, mouse constant regions were substituted by human constant regions. The constant regions of the subject humanized antibodies were derived from human immunoglobulins. However, these humanized antibodies still elicited an unwanted and potentially dangerous immune response in humans and there was a loss of affinity. Humanized antibodies, for example, humanized anti-CD40 antibodies, for use in the methods of the present invention have binding characteristics similar to those exhibited by the parent antibody of interest, for example, the CHIR-5.9 and CHIR-12.12 monoclonal antibodies described herein.

Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting rodent or mutant rodent CDRs or CDR sequences for the corresponding sequences of a human antibody. See also U.S. Pat. Nos. 5,225,539; 5,585,089; 5,693,761; 5,693,762; 5,859,205; herein incorporated by reference. In some instances, residues within the framework regions of one or more variable regions of the human immunoglobulin are replaced by corresponding non-human residues (see, for example, U.S. Pat. Nos. 5,585,089; 5,693,761; 5,693,762; and 6,180,370). Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the hypervariable regions correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al. (1986) *Nature* 331:522-525; Riechmann et al. (1988) *Nature* 332:323-329; and Presta (1992) *Curr. Op. Struct. Biol.* 2:593-596; herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

The present invention can also be practiced using xenogeneic or modified antibodies produced in a non-human mammalian host, more particularly a transgenic mouse, characterized by inactivated endogenous immunoglobulin (Ig) loci. In such transgenic animals, competent endogenous genes for the expression of light and heavy subunits of host immunoglobulins are rendered non-functional and substituted with the analogous human immunoglobulin loci. These transgenic animals produce human antibodies in the substantial absence of light or heavy host immunoglobulin subunits. See, for example, U.S. Pat. Nos. 5,877,397 and 5,939,598, herein incorporated by reference.

In some embodiments, fully human antibodies to CD40, for example, are obtained by immunizing transgenic mice. One such mouse is obtained using XenoMouse® technology (Abgenix; Fremont, Calif.), and is disclosed in U.S. Pat. Nos. 6,075,181, 6,091,001, and 6,114,598, all of which are incorporated herein by reference. To produce the antibodies disclosed herein, mice transgenic for the human Ig $G_1$ heavy chain locus and the human K light chain locus were immunized with Sf9 cells expressing human CD40. Mice can also be transgenic for other isotypes. Fully human anti-CD40 antibodies useful in the methods of the present invention are characterized by binding properties similar to those exhibited by the CHIR-5.9 and CHIR-12.12 monoclonal antibodies disclosed herein.

Fragments of a particular antibody of interest, for example, an anti-CD40 antibody or anti-CD40L antibody, are suitable for use in the methods of the invention so long as they retain the desired affinity of the full-length antibody. Thus, for example, a fragment of an anti-CD40 antibody will retain the ability to bind to the CD40 B cell surface antigen. Such fragments are characterized by properties similar to the corresponding full-length antibody. Thus, for example, a fragment of a full-length antagonist anti-CD40 antibody will specifically bind a human CD40 antigen expressed on the surface of a human cell, and is free of significant agonist activity but exhibits antagonist activity when bound to a CD40 antigen on a human CD40-expressing cell. Such fragments are referred to herein as "antigen-binding" fragments.

Suitable antigen-binding fragments of an antibody comprise a portion of a full-length antibody, generally the antigen-binding or variable region thereof. Examples of antibody fragments include, but are not limited to, Fab, F(ab')$_2$, and Fv fragments and single-chain antibody molecules. By "Fab" is intended a monovalent antigen-binding fragment of an immunoglobulin that is composed of the light chain and part of the heavy chain. By F(ab')$_2$ is intended a bivalent antigen-binding fragment of an immunoglobulin that contains both light chains and part of both heavy chains. By "single-chain Fv" or "sFv" antibody fragments is intended fragments comprising the $V_H$ and $V_L$ domains of an antibody, wherein these domains are present in a single polypeptide chain. See, for example, U.S. Pat. Nos. 4,946,778, 5,260,203, 5,455,030, and 5,856,456, herein incorporated by reference. Generally, the Fv polypeptide further comprises a polypeptide linker between the $V_H$ and $V_L$ domains that enables the sFv to form the desired structure for antigen binding. For a review of sFv see Pluckthun (1994) in *The Pharmacology of Monoclonal Antibodies*, Vol. 113, ed. Rosenburg and Moore (Springer-Verlag, New York), pp. 269-315. Antigen-binding fragments of the antagonist anti-CD40 antibodies disclosed herein can also be conjugated to a cytotoxin to effect killing of the target cancer cells, as described herein below.

Antibodies or antibody fragments can be isolated from antibody phage libraries generated using the techniques described in, for example, McCafferty et al. (1990) *Nature* 348:552-554 (1990) and U.S. Pat. No. 5,514,548. Clackson et al. (1991) *Nature* 352:624-628 and Marks et al. (1991) *J. Mol. Biol.* 222:581-597 describe the isolation of murine and human antibodies, respectively, using phage libraries. Subsequent publications describe the production of high affinity (nM range) human antibodies by chain shuffling (Marks et al. (1992) *Bio/Technology* 10:779-783), as well as combinatorial infection and in vivo recombination as a strategy for constructing very large phage libraries (Waterhouse et al. (1993) *Nucleic. Acids Res.* 21:2265-2266). Thus, these techniques are viable alternatives to traditional monoclonal antibody hybridoma techniques for isolation of monoclonal antibodies.

Various techniques have been developed for the production of antibody fragments. Traditionally, these fragments were derived via proteolytic digestion of intact antibodies (see, e.g., Morimoto et al. (1992) *Journal of Biochemical and Biophysical Methods* 24:107-117 (1992) and Brennan et al. (1985) *Science* 229:81). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al. (1992) *Bio/Technology* 10:163-167). According to another approach, F(ab')$_2$ fragments can be isolated directly from recombinant host cell culture. Other techniques for the production of antibody fragments will be apparent to the skilled practitioner.

Antagonist anti-CD40 antibodies for use in the methods of the present invention include the CHIR-5.9 and CHIR-12.12 monoclonal antibodies disclosed herein as well as antibodies differing from this antibody but retaining the CDRs; and antibodies with one or more amino acid addition(s), deletion(s), or substitution(s), wherein the antagonist activity is measured by inhibition of B-cell proliferation and/or differentiation. The invention also encompasses de-immunized antibodies, particularly de-immunized antagonist anti-CD40 antibodies, which can be produced as described in, for example, International Publication Nos. WO 98/52976 and WO 0034317; herein incorporated by reference. In this manner, residues within the antagonist anti-CD40 antibodies of the invention are modified so as to render the antibodies non- or less immunogenic to humans while retaining their antagonist activity toward human CD40-expressing cells, wherein such activity is measured by assays noted elsewhere herein. Also included within the scope of the present invention are fusion proteins comprising an antibody of interest, for example, an antagonist anti-CD40 antibody or an antagonist anti-CD40L antibody, or a fragment thereof, which fusion proteins can be synthesized or expressed from corresponding polynucleotide vectors, as is known in the art. Such fusion proteins are described with reference to conjugation of antibodies as noted elsewhere herein.

Any known antibody having the binding specificity of interest can have sequence variations produced using methods described in, for example, Patent Publication Nos. EP 0 983 303 A1, WO 00/34317, and WO 98/52976, incorporated herein by reference. For example, it has been shown that sequences within the CDR can cause an antibody to bind to MHC Class II and trigger an unwanted helper T-cell response. A conservative substitution can allow the antibody to retain binding activity yet lose its ability to trigger an unwanted T-cell response. Any such conservative or non-conservative substitutions can be made using art-recognized methods, such as those noted elsewhere herein, and the resulting antibodies can also be used in the methods of the present invention. The variant antibodies can be routinely tested for the particular activity, for example, antagonist activity, affinity, and specificity using methods described herein.

Where the anti-CD40 therapeutic agent is an antagonist anti-CD40 antibody, the antagonist anti-CD40 antibody produced by any of the methods described above, or any other method not disclosed herein, can be used in a manner similar to the CHIR-12.12 or CHIR-5.9 antibody where it possesses at least one of the following biological activities: inhibition of immunoglobulin secretion by normal human peripheral B cells stimulated by T cells; inhibition of survival and/or proliferation of normal human peripheral B cells stimulated by Jurkat T cells; inhibition of survival and/or proliferation of normal human peripheral B cells stimulated by CD40L-expressing cells or soluble CD40 ligand (sCD40L); inhibition of "survival" anti-apoptotic intracellular signals in any cell stimulated by sCD40L or solid-phase CD40L; inhibition of CD40 signal transduction in any cell upon ligation with sCD40L or solid-phase CD40L; and inhibition of proliferation of human malignant B cells as noted below. Assays for such biological activities can be performed as described herein and in provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively; and International Patent Application No. PCT/US2004/037152, also entitled "Antagonist Anti-CD40 Monoclonal Antibodies and Methods for Their Use," filed Nov. 4, 2004; the contents of each of which are herein incorporated by reference in their entirety. See also the assays described in Schultze et al. (1998) *Proc. Natl. Acad. Sci. USA* 92:8200-8204; Denton et al. (1998) *Pediatr. Transplant.* 2:6-15; Evans et al. (2000) *J. Immunol.* 164:688-697; Noelle (1998) *Agents Actions Suppl.* 49:17-22; Lederman et al. (1996) *Curr Opin. Hematol.* 3:77-86; Coligan et al. (1991) *Current Protocols in Immunology* 13:12; Kwekkeboom et al. (1993) *Immunology* 79:439-444; and U.S. Pat. Nos. 5,674,492 and 5,847,082; herein incorporated by reference.

A representative assay to detect antagonist anti-CD40 antibodies specific to the CD40-antigen epitopes identified herein is a "competitive binding assay." Competitive binding assays are serological assays in which unknowns are detected and quantitated by their ability to inhibit the binding of a labeled known ligand to its specific antibody. This is also referred to as a competitive inhibition assay. In a representative competitive binding assay, labeled CD40 polypeptide is precipitated by candidate antibodies in a sample, for example, in combination with monoclonal antibodies raised against one or more epitopes of the monoclonal antibodies of the invention. Anti-CD40 antibodies that specifically react with an epitope of interest can be identified by screening a series of antibodies prepared against a CD40 protein or fragment of the protein comprising the particular epitope of the CD40 protein of interest. For example, for human CD40, epitopes of interest include epitopes comprising linear and/or nonlinear amino acid residues of the short isoform of human CD40 (see GenBank Accession No. NP_690593) set forth in SEQ ID NO:10, encoded by the sequence set forth SEQ ID NO:9; see also GenBank Accession No. NM_152854), or of the long isoform of human CD40 (see GenBank Accession Nos. CAA43045 and NP_001241, set forth in SEQ ID NO:12, encoded by the sequence set forth in SEQ ID NO:11; see GenBank Accession Nos. X60592 and NM_001250). Alternatively, competitive binding assays with previously identified suitable antagonist anti-CD40 antibodies could be used to select monoclonal antibodies comparable to the previously identified antibodies.

Antibodies employed in such immunoassays may be labeled or unlabeled. Unlabeled antibodies may be employed in agglutination; labeled antibodies may be employed in a wide variety of assays, employing a wide variety of labels. Detection of the formation of an antibody-antigen complex between an anti-CD40 antibody and an epitope of interest can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include $^{125}$I, $^{131}$I, $^{35}$S, or $^{3}$H. Such labeled reagents may be used in a variety of well-known assays, such as radioimmunoassays, enzyme immunoassays, e.g., ELISA, fluorescent immunoassays, and the like. See for example, U.S. Pat. Nos. 3,766,162; 3,791,932; 3,817,837; and 4,233,402.

Any of the previously described antibodies, for example, antagonist anti-CD40 antibodies or antibody fragments thereof, may be conjugated prior to use in the methods of the present invention. Methods for producing conjugated antibodies are known in the art. Thus, the antibody may be labeled using an indirect labeling or indirect labeling approach. By "indirect labeling" or "indirect labeling approach" is intended that a chelating agent is covalently attached to an antibody and at least one radionuclide is inserted into the chelating agent. See, for example, the chelating agents and radionuclides described in Srivagtava and Mease (1991) *Nucl. Med. Bio.* 18:589-603, herein incorporated by reference. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefore. Other specific binding partners include biotin and avidin or streptavidin, Ig G and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a mAb. Further, one may combine various labels for desired effect. For example, mAbs and avidin also require labels in the practice of this invention: thus, one might label a mAb with biotin, and detect its presence with avidin labeled with $^{125}$I, or with an anti-biotin mAb labeled with HRP. Other permutations and possibilities will be readily apparent to those of ordinary skill in the art, and are considered as equivalents within the scope of the instant invention.

Alternatively, an antibody of interest, for example, an anti-CD40 antibody, may be labeled using "direct labeling" or a "direct labeling approach," where a radionuclide is covalently attached directly to an antibody (typically via an amino acid residue). Preferred radionuclides are provided in Srivagtava and Mease (1991) supra. The indirect labeling approach is particularly preferred. See also, for example, International Publication Nos. WO 00/52031 and WO 00/52473, where a linker is used to attach a radioactive label to antibodies; and the labeled forms of anti-CD40 antibodies described in U.S. Pat. No. 6,015,542; herein incorporated by reference.

Variants of Antibodies

The methods of the present invention can be carried out using variants of an antibody known in the art. Such variants will retain the desired binding properties of the parent antibody. Thus, for example, where the anti-CD40 therapeutic agent to be tested is an antagonist anti-CD40 antibody, the variant antibody will retain the binding properties of the parent antagonist anti-CD40 antibody, for example, the CHIR-12.12 or CHIR-5.9 antibody. Methods for making antibody variants are generally available in the art. Though the following discussion refers to variants of an antagonist anti-CD40 antibody, the methods are generally applicable to any antibody of interest, for example, an antibody that specifically binds to a biomarker or clinically useful prognostic marker disclosed herein.

For example, amino acid sequence variants of an antagonist anti-CD40 antibody, for example, the CHIR-5.9 or CHIR-12.12 monoclonal antibody described herein, can be prepared by mutations in the cloned DNA sequence encoding the antibody of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488-492; Kunkel et al. (1987) *Methods Enzymol.* 154:367-382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇔Ala, Val⇔Ile⇔Leu, Asp⇔Glu, Lys⇔Arg, Asn⇔Gln, and Phe⇔Trp⇔Tyr.

In constructing variants of an antibody of interest, for example, an antagonist anti-CD40 antibody polypeptide of interest, modifications are made such that variants continue to possess the desired activity, i.e., similar binding affinity and, in the case of antagonist anti-CD40 antibodies, are capable of specifically binding to a human CD40 antigen expressed on the surface of a human cell, and being free of significant agonist activity but exhibiting antagonist activity when bound to a CD40 antigen on a human CD40-expressing cell. Obviously, any mutations made in the DNA encoding the variant polypeptide must not place the sequence out of reading frame and preferably will not create complementary regions that could produce secondary mRNA structure. See EP Patent Application Publication No. 75,444.

In addition, the constant region of an antibody, for example, an antagonist anti-CD40 antibody, can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

Preferably, variants of a reference antibody, for example, an antagonist anti-CD40 antibody, have amino acid sequences that have at least 70% or 75% sequence identity, preferably at least 80% or 85% sequence identity, more preferably at least 90%, 91%, 92%, 93%, 94% or 95% sequence identity to the amino acid sequence for the reference antibody, for example, an antagonist anti-CD40 antibody molecule, for example, the CHIR-5.9 or CHIR-12.12 monoclonal antibody described herein, or to a shorter portion of the reference antibody molecule. More preferably, the molecules share at least 96%, 97%, 98% or 99% sequence identity. For purposes of the present invention, percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482-489. A variant may, for example, differ from the reference antibody, for example, an antagonist anti-CD40 antibody, by as few as 1 to 15 amino acid residues, as few as 1 to 10 amino acid residues, such as 6-10, as few as 5, as few as 4, 3, 2, or even 1 amino acid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

Methods of Therapy

The ex vivo prognostic assays described herein can also be used in methods of therapy for a subject in need of treatment for a cancer or pre-malignant condition associated with CD40-expressing neoplastic cells. Thus, in some embodiments, the ex vivo prognostic assay is carried out on a candidate subject, and, where results of the assay predict a favorable response with treatment with the anti-CD40 therapeutic agent, the subject is then treated with that anti-CD40 therapeutic agent. As noted herein above, the information obtained from the ex vivo prognostic assay can be used alone to render a decision with regard to benefit of treatment with the anti-CD40 therapeutic agent. Alternatively, the ex vivo prognostic assay can be used in combination with prognostic assays that screen for level of expression, or presence or absence of expression, of one or more of the CD40-related factors identified herein; prognostic assays that screen for level of expression, or presence or absence of expression, of one or more clinically useful prognostic markers for the particular cancer or pre-malignant condition, for example, for a subject with CLL, a clinically useful prognostic marker such as ZAP-70 expression level, CD38 expression level, β2 microglobulin expression level, p53 mutational status, ATM mutational status, chromosome 17p deletion, and chromosome 11q deletion identified herein above; or both.

In this manner, a subject identified using the ex vivo prognostic assays of the present invention, alone or in combination with other prognostic assays described herein, can be further treated with one or more therapeutically effective doses of the anti-CD40 therapeutic agent that has been identified in the screening process as being beneficial for treatment of the disease in the candidate subject. "Treatment" is herein defined as the application or administration of an anti-CD40 therapeutic agent to a patient, or application or administration of an anti-CD40 therapeutic agent to an isolated tissue or cell line from a patient, where the patient has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease. By "treatment" is also intended the application or administration of a pharmaceutical composition comprising the anti-CD40 therpaeutic agent to a patient, or application or administration of a pharmaceutical composition comprising the anti-CD40 therapeutic agent, to an isolated tissue or cell line from a patient, who has a disease, a symptom of a disease, or a predisposition toward a disease, where the purpose is to cure, heal, alleviate, relieve, alter, remedy, ameliorate, improve, or affect the disease, the symptoms of the disease, or the predisposition toward the disease.

By "anti-tumor activity" is intended a reduction in the rate of malignant CD40-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one anti-CD40 therapeutic agent identified using the ex vivo prognostic assays described herein causes a physiological response that is beneficial with respect to treatment of cancers and pre-malignant conditions associated with stimulation of CD40 signaling on CD40-expressing cells in a human.

By "therapeutically effective dose or amount" or "effective amount" is intended an amount of the anti-CD40 therapeutic agent that, when administered brings about a positive therapeutic response with respect to treatment of a patient with a disease comprising CD40-expressing neoplastic cells. In some embodiments of the invention, the anti-CD40 therapeutic agent is an antagonist anti-CD40 antibody, an antagonist anti-CD40L antibody, or antigen-binding fragment thereof, and the therapeutically effective dose of the anti-CD40 antibody, anti-CD40L antibody, or fragment thereof, is in the range from about 0.01 mg/kg to about 40 mg/kg, from about 0.01 mg/kg to about 30 mg/kg, from about 0.1 mg/kg to about 30 mg/kg, from about 1 mg/kg to about 30 mg/kg, from about 3 mg/kg to about 30 mg/kg, from about 3 mg/kg to about 25 mg/kg, from about 3 mg/kg to about 20 mg/kg, from about 5 mg/kg to about 15 mg/kg, or from about 7 mg/kg to about 12 mg/kg. It is recognized that the method of treatment may comprise a single administration of a therapeutically effective dose or multiple administrations of a therapeutically effective dose of the anti-CD40 therapeutic agent, for example, an antagonist anti-CD40 antibody, antagonist anti-CD40L antibody, or antigen-binding fragment thereof.

In some embodiments, the ex vivo prognostic assays of the invention can be used to ascertain the physiological basis for responsiveness, or lack of responsiveness, to treatment with a particular anti-CD40 therapeutic agent. Thus, where a cancer or pre-malignant condition in a subject is initially responsive to therapy with an anti-CD40 therapeutic agent, and CD40-expressing neoplastic cells of the cancer or pre-malignant condition develop resistance to this line of therapy, the ex vivo prognostic assays can be used to define which CD40L-CD40 interaction(s) contribute to the refractory nature of these CD40-expressing neoplastic cells.

The biomarkers of CD40L-mediated CD40 signaling, i.e., biomarkers of apoptosis, cell proliferation and survival, cytokine markers of CD40L-mediated CD40 signaling, and CD40-related factors described herein can also be used, alone or in any combination thereof, to monitor efficacy of treatment with an anti-CD40 therapeutic agent. In this manner, a subject who is undergoing treatment with an anti-CD40 therapeutic agent, who may or may not have been previously screened for suitability of treatment with the anti-CD40 therapeutic agent using a prognostic assay described above, is monitored for in vivo changes in the expression of at least one biomarker of cellular apoptosis, cell proliferation and survival, and/or one or more CD40 signaling pathways, wherein cytokine production is optionally monitored (depending upon the mode of action of the anti-CD40 therapeutic agent) following treatment with the anti-CD40 therapeutic agent. Alternatively, or additionally, the subject can be monitored for in vivo changes in the expression level of one or more CD40-related factors selected from the group consisting of cell-surface CD40 antigen on neoplastic cells, cell-surface CD40L on neoplastic cells, circulating level of sCD40, and circulating level of sCD40L following treatment with the anti-CD40 therapeutic agent.

In this manner, a first biological sample is obtained from the subject prior to treatment with the anti-CD40 therapeutic agent of interest and assayed for the expression level of one or more of these biomarkers and/or CD40-related factors to obtain a baseline level of expression for each factor assayed. This first biological sample is referred to as the "baseline biological sample." One or more subsequent biological samples, of the same tissue type or bodily fluid, is obtained from the subject and assayed for the same biomarker(s) and/or CD40-related factor(s), where the subsequent biological sample is obtained following the administration of at least one dose of the anti-CD40 therapeutic agent of interest. Monitoring can occur at a single point in time, or at multiple points in time to ascertain efficacy of any given treatment protocol wherein the anti-CD40 therapeutic agent is administered to the subject. Depending upon the biomarker being assayed, a decrease or increase in the level of the biomarker between any two time points is indicative of efficacy of the anti-CD40 therapeutic agent in treatment of the cancer or pre-malignant condition. Where monitoring reveals a decrease in the expression level of one or more of the CD40-related factors, such a result is indicative of efficacy of the anti-CD40 therapeutic agent in treatment of the cancer or pre-malignant condition.

Thus, in some embodiments, efficacy of treatment of a subject with an anti-CD40 therapeutic agent that blocks or interferes with CD40L-mediated CD40 signaling is monitored by obtaining a baseline biological sample from the subject and detecting the level of expression of one or more biomarkers of cell survival and/or a CD40L-mediated CD40 signaling pathway described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 30 minutes to about 24 hours, including about 30 minutes to about 12 hours, about 30 minutes to about 6 hours, about 30 minutes to about 4 hours, and about 1 hour to about 4 hours; and detecting the level of expression of the biomarker(s) of cell survival and/or CD40L-mediated CD40 signaling pathway in the subsequent biological sample; wherein a reduction in the level of expression in the subsequent biological sample compared to the level of expression in the baseline biological sample is indicative of efficacy of treatment with the anti-CD40 therapeutic agent. Detection can be accomplished using any method known in the art including those methods disclosed elsewhere herein. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample. A percent change from baseline of at least 25% (i.e., at least a 25% reduction relative to the baseline biological sample) is indicative of efficacy of the anti-CD40 therapeutic agent, with intermediate responsiveness indicated by a percent change of at least 30% or at least 40%. Preferably, the percent change from baseline is at least 50% (i.e., at least a 50% reduction relative to the baseline biological sample) or higher.

In some embodiments, efficacy of treatment of a subject with an anti-CD40 therapeutic agent that blocks or interferes with CD40L-mediated CD40 signaling is monitored by obtaining a baseline biological sample from the subject and detecting the level of expression of cytokine markers of CD40L-mediated CD40 signaling described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 24 hours to about 3 weeks, including about 48 hours, about 72 hours, about 1 week, or about 2 weeks, after dosing; and detecting the level of expression of the biomarker(s) of cell survival and/or CD40L-mediated CD40 signaling pathway in the subsequent biological sample; wherein a reduction in the level of expression in the subsequent biological sample compared to the level of expression in the baseline biological sample is indicative of efficacy of treatment with the anti-CD40 therapeutic agent. Detection can be accomplished using any method known in the art including those methods disclosed elsewhere herein. Further, cytokines that are not affected by CD40L-mediated CD40 signaling (for example, IL-1b and IL-12; see the Experimental section herein below) can be used as a control to normalize data. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample. A percent change from baseline of at least 20% (i.e., at least a 20% reduction relative to the baseline biological sample) or higher is indicative of efficacy of the anti-CD40 therapeutic agent. In some embodiments, baseline biological samples comprising serum or serum extract are frozen for subsequent analysis of cytokine markers.

In other embodiments, efficacy of treatment of a subject with an anti-CD40 therapeutic agent that blocks or interferes with CD40L-mediated CD40 signaling, or which has ADCC as its mode of action, is monitored by obtaining a baseline biological sample from the subject and detecting the level of expression of one or more biomarkers of apoptosis described herein above; administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 8 hours, 12 hours, 24 hours, 36 hours, 48 hours, or 72 hours after dosing, and optionally again about 1 week, about 2 weeks, or about 3 weeks after dosing; and detecting the level of expression of the biomarker(s) of apoptosis in the subsequent biological sample(s); wherein an increase in the level of expression in the subsequent biological sample(s) compared to the level of expression in the baseline biological sample is indicative of efficacy of treatment with the anti-CD40 therapeutic agent. Detection can be accomplished using any method known in the art including those methods disclosed elsewhere herein. In some embodiments, the level of expression is increased by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 200%, 250%, 300%, or higher relative to that detected in the baseline biological sample. A percent change from baseline of at least 20% (i.e., at least a 20% increase relative to the baseline biological sample) or higher is indicative of efficacy of the anti-therapeutic agent.

In yet other embodiments, efficacy of treatment of a subject with an anti-CD40 therapeutic agent that blocks or interferes with CD40L-mediated CD40 signaling, modulates ADCC, or both, is monitored by obtaining a baseline biological sample from the subject and detecting the level of expression of one or more CD40-related factors described herein above (i.e., cell-surface CD40 and/or CD40L on neoplastic cells, and/or circulating levels of sCD40 and/or sCD40L); administering at least one dose of the therapeutic agent, for example, an antagonist anti-CD40 antibody such as CHIR-12.12 or CHIR-5.9 or antigen-binding fragment thereof, to the subject; obtaining a subsequent biological sample from the subject, for example, within about 1 day (i.e., 24 hours), 2 days, 3 days, 4 days, or 1 week; and detecting the level of expression of the CD40-related factor; wherein a reduction in the level of expression in the subsequent biological sample compared to the level of expression in the baseline biological sample is indicative of efficacy of treatment with the anti-CD40 therapeutic agent. In some embodiments, the level of expression is reduced by at least about 5%, 10%, 15%, 20%, 25%, 30%, 35%, 40%, 45%, 50%, 55%, 60%, 65%, 70%, 75%, 80%, 85%, 90%, 95%, or 100% relative to that detected in the baseline biological sample.

It is recognized that any one or a combination of these assays can be carried out to monitor efficacy of treatment of a subject with a cancer or pre-malignant condition with an anti-CD40 therapeutic agent of interest, depending upon its mode of action. Where efficacy is demonstrated, subsequent doses of the anti-CD40 therapeutic agent can be administered according to the recommended dosing regimen, for example, daily, every other day, thrice weekly, twice weekly, once a week, bi-weekly, monthly, and the like. Alternatively, the in vivo level of expression of the marker(s) of interest (i.e., biomarker(s) of cell proliferation and survival, biomarker(s) of CD40L-mediated CD40 signaling pathways, cytokine marker(s), CD40-related factor(s), and any combination thereof can serve as a guide to dosing frequency, and can also serve as an indication as to therapeutically effective dose to be administered. In this manner, where subsequent biological samples continue to show an acceptable reduction or increase in the expression level of the respective marker(s) of interest, further dosing with the anti-CD40 therapeutic agent can be delayed until such time as the expression level of the respective marker(s) approaches that observed in the baseline biological sample. As some biomarkers may fluctuate independently of the effects of the therapeutic agent, which also will vary in half-life and residence times, preferably at least two consecutive measurements (for example, within a 24-48 hour period) are taken into consideration when using the expression level of the marker (i.e., biomarker of apoptosis, cell survival, CD40-signaling pathway, cytokine marker, and/or CD40-related factor) as a guide to dosing frequency.

Where results of these assays continue to show desired downregulation of CD40L-mediated CD40 signaling with respect to a decline in expression of one or more of the biomarkers of cell survival, one or more of the biomarkers of a CD40 signaling pathway, and/or one or more of the CD40-related factors, and an increase in expression of one or more of the markers of cell apoptosis, further treatment with the anti-CD40 therapeutic agent is warranted. Biological samples can be collected at various time intervals over the course of a treatment period as noted herein above to allow for monitoring of treatment efficacy over time, and to determine whether treatment should be continued or withdrawn.

The following examples are offered by way of illustration and not by way of limitation.

EXPERIMENTAL

Introduction

The antagonist anti-CD40 antibodies used in the examples below are CHIR-5.9 and CHIR-12.12. The CHIR-5.9 and CHIR-12.12 anti-CD40 antibodies are human IgG$_1$ subtype anti-human CD40 monoclonal antibodies (mAbs) generated by immunization of transgenic mice bearing the human IgG1 heavy chain locus and the human κ light chain locus (XenoMouse® technology (Abgenix; Fremont, Calif.)). SF9 insect cells expressing CD40 extracellular domain were used as immunogen.

Briefly, splenocytes from immunized mice were fused with SP 2/0 or P 3×63Ag8.653 murine myeloma cells at a ratio of 10:1 using 50% polyethylene glycol as previously described by de Boer et al. (1988) *J Immunol. Meth.* 113:143. The fused cells were resuspended in complete IMDM medium supplemented with hypoxanthine (0.1 mM), aminopterin (0.01 mM), thymidine (0.016 mM), and 0.5 ng/ml hIL-6 (Genzyme, Cambridge, Mass.). The fused cells were then distributed between the wells of 96-well tissue culture plates, so that each well contained 1 growing hybridoma on average.

After 10-14 days, the supernatants of the hybridoma populations were screened for specific antibody production. For the screening of specific antibody production by the hybridoma clones, the supernatants from each well were pooled and tested for anti-CD40 activity specificity by ELISA first. The positives were then used for fluorescent cell staining of EBV-transformed B cells using a standard FACS assay. Positive hybridoma cells were cloned twice by limiting dilution in IMDM/FBS containing 0.5 ng/ml hIL-6.

A total of 31 mice spleens were fused with the mouse myeloma SP2/0 cells to generate 895 antibodies that recognize recombinant CD40 in ELISA. On average approximately 10% of hybridomas produced using Abgenix XenoMouse® technology (Abgenix; Fremont, Calif.) may contain mouse lambda light chain instead of human kappa chain. The antibodies containing mouse light lambda chain were selected out. A subset of 260 antibodies that also showed binding to cell-surface CD40 were selected for further analysis. Stable hybridomas selected during a series of subcloning procedures were used for further characterization in binding and functional assays. For further details of the selection process, see copending provisional applications entitled "Antagonist Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/IUS2004/037152, also entitled "Antagonist Anti-CD40 Monoclonal Antibodies and Methods for Their Use," filed Nov. 4, 2004, and published as WO 2005/044854; the contents of each of which are herein incorporated by reference in their entirety.

Clones from 7 other hybridomas were identified as having antagonistic activity. Based on their relative antagonistic potency and ADCC activities, two hybridoma clones were selected for further evaluation (Table 1 below). They are named 131.2F8.5.9 (5.9) and 153.8E2.D10.D6.12.12 (12.12).

TABLE 1

Summary of initial set of data with anti-CD40 IgG1 antibodies CHIR-5.9 and CHIR-12.12.

| Mother Hybridoma | Hybridoma clones | Cell surface binding | Antagonist | ADCC | CDC | CMCC# | V-region DNA sequence |
|---|---|---|---|---|---|---|---|
| 131.2F5 | 131.2F5.8.5.9 | +++ | +++ | ++ | − | 12047 | Yes |
| 153.8E2 | 153.8E2D10D6.12.12 | +++ | +++ | ++++ | − | 12056 | Yes |

Mouse hybridoma line 131.2F8.5.9 (CMCC#12047) and hybridoma line 153.8E2.D10.D6.12.12 (CMCC#12056) have been deposited with the American Type Culture Collection (ATCC; 10801 University Blvd., Manassas, Va. 20110-2209 (USA)) on Sep. 17, 2003, under Patent Deposit Number PTA-5542 and PTA-5543, respectively.

The cDNAs encoding the variable regions of the candidate antibodies were amplified by PCR, cloned, and sequenced. The amino acid sequences for the light chain and heavy chain of the CHIR-12.12 antibody are set forth in SEQ ID NO:2 (light chain for mAb CHIR-12.12) and SEQ ID NO:4 (heavy chain for mAb CHIR-12.12). A variant of the heavy chain for mAb CHIR-12.12 is shown in SEQ ID NO:5, which differs from SEQ ID NO:4 in having a serine residue substituted for the alanine residue at position 153 of SEQ ID NO:4. The nucleotide sequences encoding the light chain and heavy chain of the CHIR-12.12 antibody are set forth in SEQ ID NO:1 (coding sequence for light chain for mAb CHIR-12.12) and SEQ ID NO:3 (coding sequence for heavy chain for mAb CHIR-12.12). The amino acid sequences for the light chain and heavy chain of the CHIR-5.9 antibody are set forth in SEQ ID NO:6 (light chain for mAb CHIR-5.9) and SEQ ID NO:7 (heavy chain for mAb CHIR-5.9). A variant of the heavy chain for mAb CHIR-5.9 is shown in SEQ ID NO:8, which differs from SEQ ID NO:7 in having a serine residue substituted for the alanine residue at position 158 of SEQ ID NO:7.

As expected for antibodies derived from independent hybridomas, there is substantial variation in the nucleotide sequences in the complementarity determining regions (CDRs). The diversity in the CDR3 region of $V_H$ is believed to most significantly determine antibody specificity.

As shown by FACS analysis, CHIR-5.9 and CHIR-12.12 bind specifically to human CD40 and can prevent CD40-ligand binding. Both mAbs can compete off CD40-ligand pre-bound to cell surface CD40. The binding affinity of CHIR-5.9 to human CD40 is $1.2 \times 10^{-8}$ M and the binding affinity of CHIR-12.12 to human CD40 is $5 \times 10^{-10}$ M. The CHIR-12.12 and CHIR-5.9 monoclonal antibodies are strong antagonists and inhibit in vitro CD40 ligand-mediated proliferation of normal B cells, as well as inhibiting in vitro CD40 ligand-mediated proliferation of cancer cells from NHL and CLL patients. The CHIR-12.12 monoclonal antibody directly inhibits survival and signaling pathways mediated by CD40 ligand (CD40L) in normal human B-lymphocytes. In vitro, both antibodies kill primary cancer cells from NHL patients by ADCC. Dose-dependent anti-tumor activity was seen in a xenograft human lymphoma model. For a more detailed description of these results, and the assays used to obtain them, see provisional applications entitled "Antagonist, Anti-CD40 Monoclonal Antibodies and Methods for Their Use," filed Nov. 4, 2003, Nov. 26, 2003, and Apr. 27, 2004, and assigned U.S. Patent Application Nos. 60/517,337, 60/525,579, and 60/565,710, respectively, and International Patent Application No. PCT/US2004/037152, also entitled "Antagonist, Anti-CD40 Monoclonal Antibodies and Methods for Their Use," filed Nov. 4, 2004; the contents of each of which are herein incorporated by reference in their entirety.

Example 1

CHIR-12.12 Blocks CD40L-Mediated CD40 Survival and Signaling Pathways in Human B-CLL Cells The studies described below demonstrate that CHIR-12.12 also directly inhibits survival and signaling pathways mediated by CD40 ligand (CD40L) in B-CLL. CD40L activates B-lymphocytes and induces various functional responses, including enhancement of survival, and activation of NFkB, ERK/MAPK, and PI3K/Akt signaling pathways. In addition, CD40L stimulation provides survival signals demonstrated by reduction of cleaved PARP and induction of the antiapoptotic proteins, Bcl-xl, XIAP, and cIAP. In contrast, treatment of CD40L stimulated B-CLL with CHIR-12.12 resulted in induction of cleaved caspase-3 and cleaved PARP as well as reduction of Bcl-xl, XIAP, and cIAP in a time- and dose-dependent manner. CHIR-12.12 alone did not trigger apoptosis without CD40L stimulation. We examined signal transduction events induced by CD40 activation with its ligand. The engagement of CD40 with CD40 ligand led to activation of multiple signaling pathways including NFkB, ERK/MAPK, p38, and PI3K/Akt signaling pathways. CHIR-12.12 treatment inhibited phosphorylation of IkB kinase (IKK) alpha and beta (NFκB pathway), ERK, and Akt mediated by CD40L. Using pharmacological inhibitors of PI3K (LY294002) and MEK (PD98595), we showed that CLL cell survival is at least in part dependent on the PI3K/Akt pathway. CHIR-12.12 treatment of CD40L stimulated CLL cells also inhibited cyclin D1. These results demonstrate that CHIR-12.12 blocked survival and multiple signaling pathways including NFkB, ERK, and PI3K/Akt that are mediated by CD40L in B-CLL.

The fully human antagonist anti-CD40 monoclonal antibody CHIR-12.12 was generated in XenoMouse™ mice (Abgenix, Inc.) as noted above. B-CLL cells were purchased (Cureline, Inc.; South San Francisco, Calif.), and in vitro experiments were carried out to evaluate the effect of the anti-CD40 antibody CHIR-12.12 on survival and signaling pathways mediated by CD40 ligand. NFκB, ERK, and Akt pathways were studied in these experiments.

CHIR-12.12 Treatment Inhibits Survival Mediated by CD40 Ligand in B-CLL Cells.

In these experiments, $1.0 \times 10^6$ B-CLL cells from patients were stimulated with 1 µg/ml sCD40L (Alexis Corporation, Bingham, Noffinghamshire, UK). CHIR-12.12 (10 µg/ml) and control IgG were then added. Cells were collected at 24 hours post CHIR-12.12 treatment. Cleaved PARP, which is a biomarker of apoptosis, and Bcl-xl, Bcl-2, and cIAP1, which are biomarkers of survival, were detected in cell lysates by Western blot analysis using commercially available antibodies specific for these biomarkers.

As shown in FIG. 1, treatment with CHIR-12.12 resulted in the induction of cleaved PARP and reduction of Bcl-xl, XIAP and cIAP1 in B-CLL cell samples from two patients (#4 and #21). There were no changes of Bcl-2 and TRAIL level between control and CHIR-12.12 treated cells.

Figure 2:
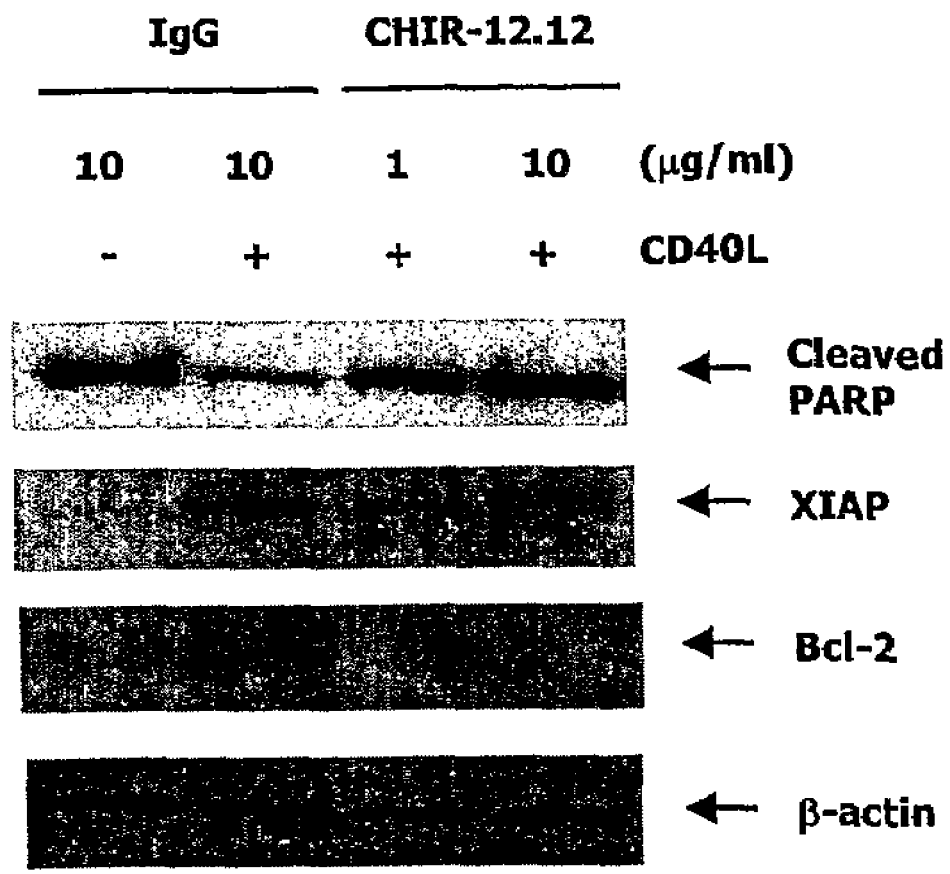
FIG. 2 shows inhibition of CD40L-mediated survival by CHIR-12.12 in B-CLL cells obtained from B-CLL patients.

Western blot analysis with B-CLL cells from patient #30 is shown in FIG. 2. CHIR-12.12 treatment induced the expression of cleaved PARP and reduced the expression of XIAP and Bcl-2 compared to the control IgG treated group.

Figure 3:
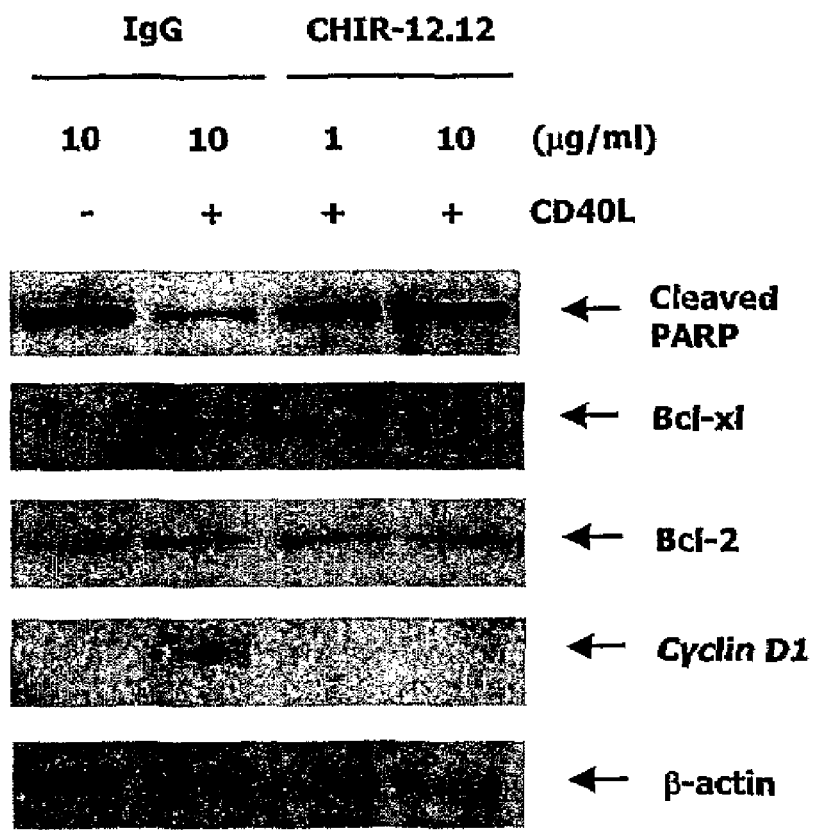
FIG. 3 shows inhibition of CD40L-mediated survival by CHIR-12.12 in B-CLL cells obtained from B-CLL patients.

Western blot analysis with B-CLL cells from patient #31 is shown in FIG. 3. CHIR-12.12 treatment induced the expression of cleaved PARP and reduced the expression of cyclin D1 and Bcl-xl compared to the control IgG treated group.

CHIR-12.12 Treatment Inhibits NFκB, ERK, PI3K/Akt, and p38 MAPK Signaling Pathways Mediated by CD40 Ligand in B-CLL.

In these experiments, $1.0 \times 10^6$ B-CLL cells from patients were stimulated with 1 µg/ml sCD40L (Alexis Corporation, Bingham, Nottinghamshire, UK). CHIR-12.12 (10 µg/ml) and control IgG were then added. Cells were collected at 0 and 20 minutes. Phosphorylated IKKα (Ser180) and IKK β (Ser 181) (p-IKK α/β; NFkB pathway), phosphorylated ERK (p-ERK), phosphorylated Akt (p-Akt), and phosphorylated p38 MAPK (p-p38) were detected in cell lysates by Western blot.

Figure 4:
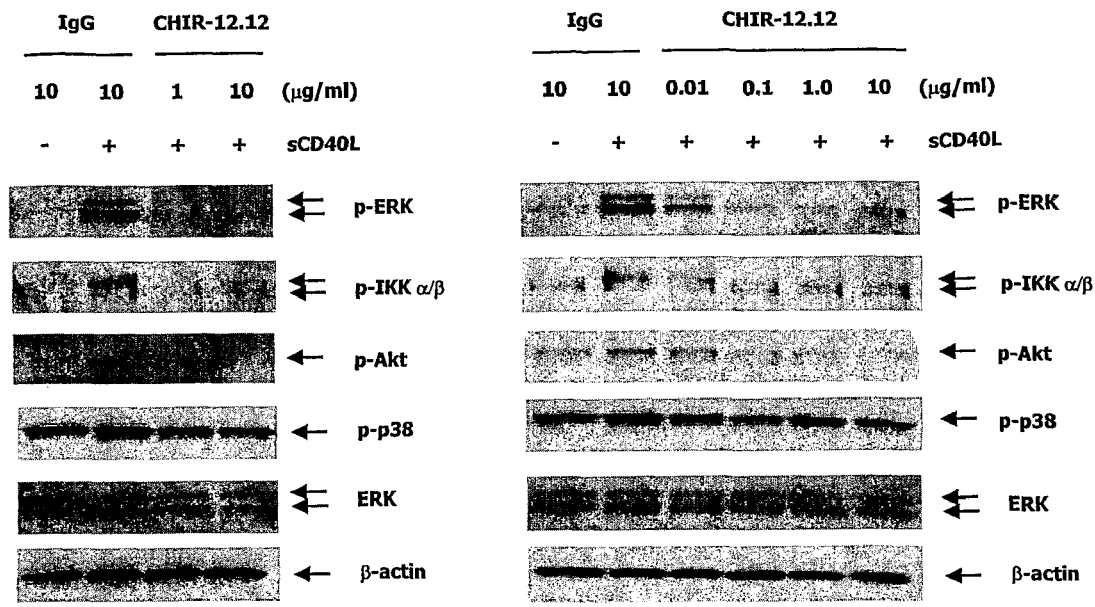
FIG. 4 shows inhibition of CD40L-mediated signaling pathways by CHIR-12.12 in B-CLL cells obtained from B-CLL patients.

As shown in FIG. 4, sCD40L stimulated phosphorylation of IKK α/β, ERK, and Akt in control IgG treated B-CLL cells within 20 minutes, and there was a significant inhibition of phosphorylation of IKK α/β, ERK, and Akt in CHIR-12.12 treated B-CLL cells. Interestingly, in these B-CLL patient samples, there was a constitutively activated p38 MAPK, and CHIR-12.12 did not significantly inhibit p38 MAPK activation.

Dose-Dependent Effect of CHIR 12.12 on Survival Mediated by CD40 Ligand in B-CLL Cells.

In these experiments, $1.0 \times 10^6$ B-CLL cells from patients were stimulated with 1 µg/ml sCD40L (Alexis Corp., Bingham, Nottinghamshire, UK). CHIR-12.12 (0, 0.010, 1, 1.0, 10, and 20 µg/ml) and control IgG were then added. Cells were collected at 22-24 hours. Western blot analysis with antibodies to cleaved PARP, caspase-3, and Bcl-xl were conducted on cell lysates. Antibody against β-actin was used for detecting equal loading and transfer efficiency.

Figure 5:
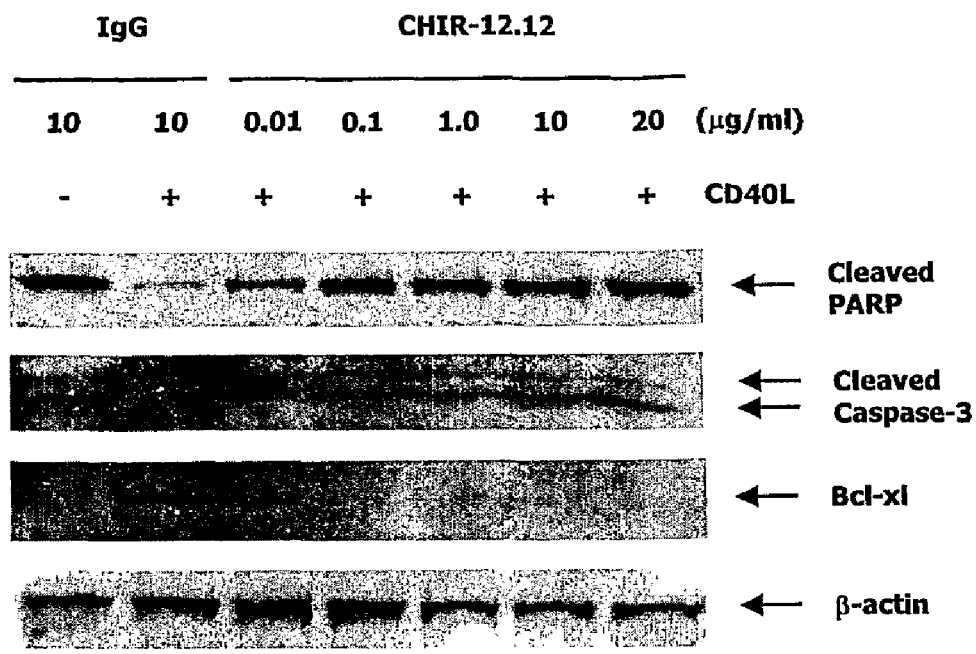
FIG. 5 shows inhibition of CD40L-mediated survival by CHIR-12.12 in B-CLL cells obtained from B-CLL patients.
Figure 6:
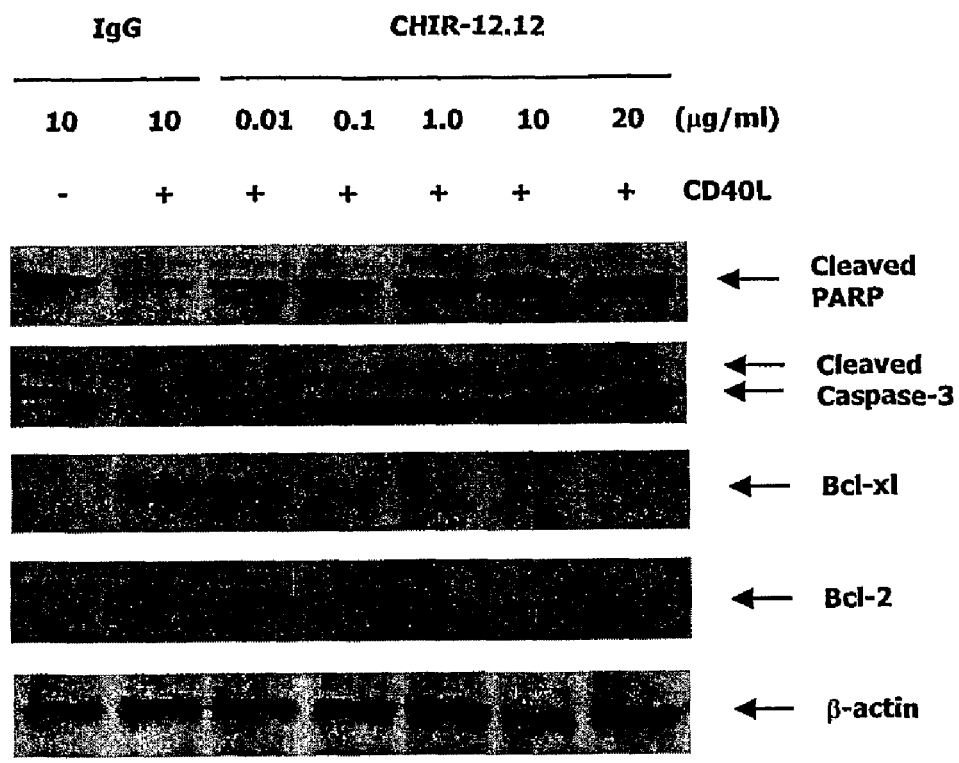
FIG. 6 shows inhibition of CD40L-mediated survival by CHIR-12.12 in B-CLL cells obtained from B-CLL patients.

As shown in FIGS. 5 and 6, treatment of sCD40L stimulated B-CLL cells with CHIR-12.12 resulted in induction of cleaved PARP and caspase-3 as well as reduction of Bcl-xl in a dose-dependent manner at doses as low as 0.01 µg/ml.

Effect of CHIR-12.12 on Apoptosis does not Occur without CD40L Stimulation in B-CLL Cells.

In this experiment, $1.0 \times 10^6$ B-CLL cells from patients, not stimulated with CD40L, were treated with CHIR-12.12 (10 µg/ml) or control IgG. Cells were collected at 1, 4, and 24 hours. Western blot analysis with antibodies to cleaved PARP (apoptotic protein) and XIAP (anti-apoptotic protein) was conducted on cell lysates.

Figure 7:
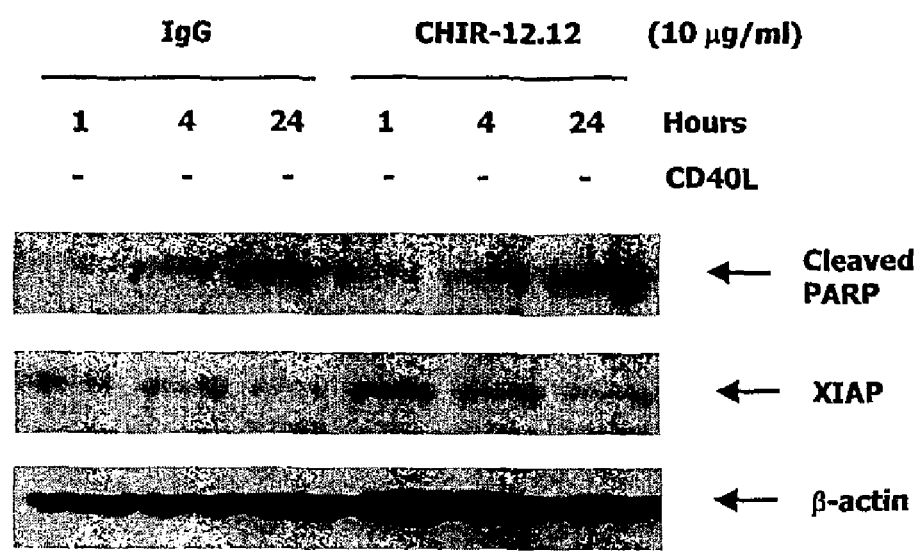
FIG. 7 demonstrates that CHIR-12.12 does not trigger apoptosis without CD40L stimulation.

The results shown in FIG. 7 indicate that CD40 ligand stimulation is necessary for survival of B-CLL cells, and CHIR-12.12 alone did not trigger additional apoptosis of B-CLL cells.

Signaling Pathways Required for CLL Cell Survival.

A PI3K inhibitor (LY294002; Sigma, St. Louis, Mo.) and MEK inhibitor (PD98595; Cell Signaling Technology, Beverly, Mass.) were used to dissect the pathways required for CLL cell survival. In these experiments, $1.0 \times 10^6$ B-CLL cells from patients were serum starved in 1% FBS containing media for 4 hours. Serum-starved cells were then pretreated with LY294002 (PI3K inhibitor, 30 µM) or PD98595 (MEK inhibitor, 10 µM). Cell lysates were then collected before and 20 minutes after CD40L stimulation. Western blot analysis with antibodies to p-IKK α/β, p-ERK, p-Akt was conducted, and equal loading was evaluated by probing antibodies to total ERK and β-actin.

Figure 8:
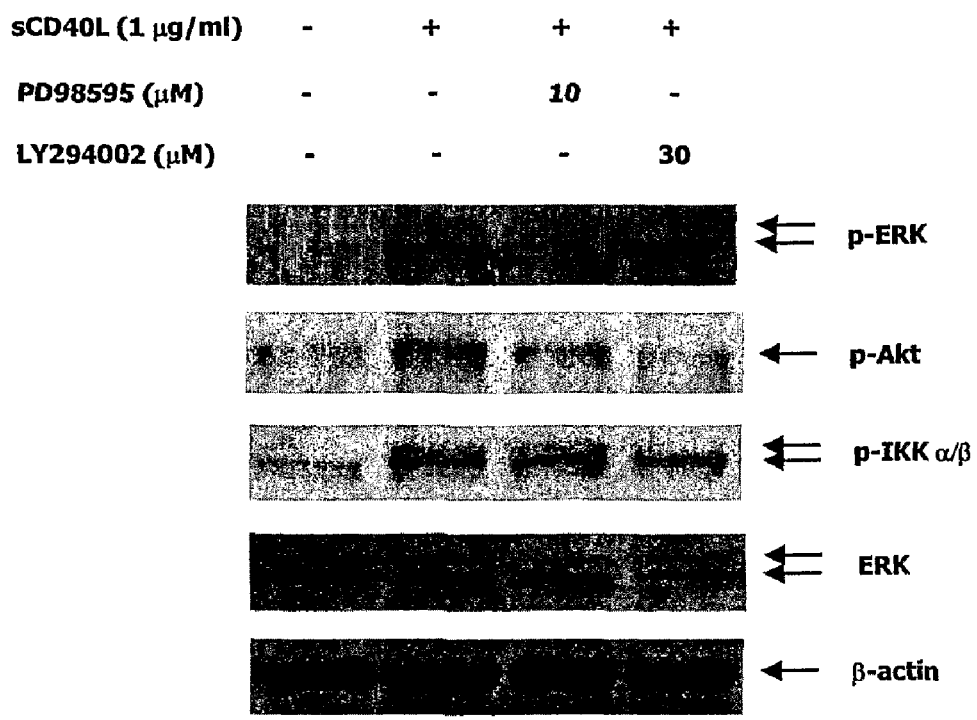
FIG. 8 shows the effect of inhibition of PI3K (LY294002) and MEK (PD98595) on CD40L-mediated CD40 signaling pathways leading to a reduction in p-ERK, p-Akt, and p-IKK α/β.

As shown in FIG. 8 and as expected, PD98595 inhibited activation of ERK and LY294002 inhibited activation of Akt that were induced by CD40L treatment. There was no change of IKK/NFkB activation by either inhibitor.

Figure 9:
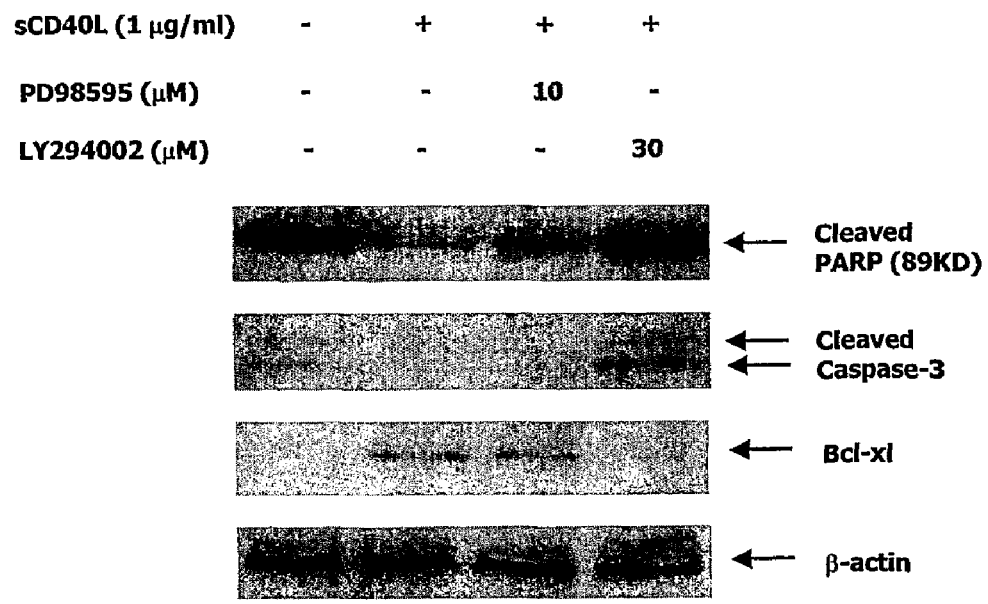
FIG. 9 shows the effect of inhibition of PI3K (LY294002) and MEK (PD98595) on survival mediated by CD40L interaction with CD40.

However, only B-CLL cells treated with PI3K inhibitor, LY294002, showed induction of cleaved PARP and caspase-3 as well as reduction of Bcl-xl, an anti-apoptotic protein (FIG. 9). There was no change of survival mediated by CD40L with MEK inhibitor, PD98595. This supports the finding that B-CLL cell survival is mediated through the PI3K/Akt signaling pathway.

CHIR-12.12 Treatment Inhibits Survival Mediated by CD40 Ligand in B-CLL Patient Cells Using Flow Cytometry Analysis.

In this experiment, $0.4 \times 10^6$ B-CLL cells from patients were stimulated with 1 µg/ml sCD40L (Alexis Corp., Bingham, Nottinghamshire, UK). CHIR12.12 (10 µg/ml) or control IgG was then added. Cells were collected at 24 hours post-treatment with CHIR-12.12. After fixation and permeabilization, the cells were stained for cleaved PARP and TUNEL methods.

Figure 10:
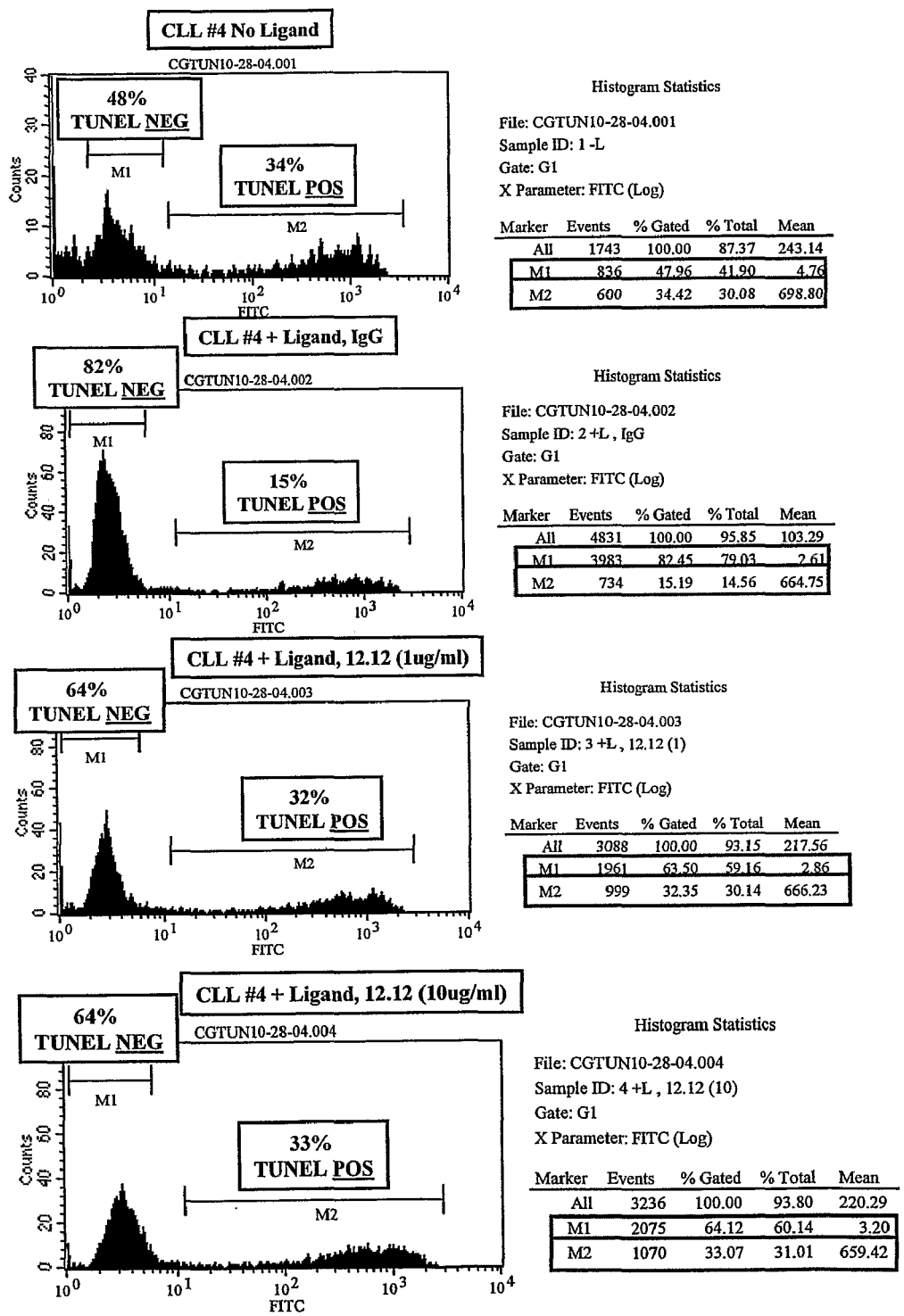
FIG. 10 shows inhibition of CD40L-mediated survival (TUNEL) by CHIR-12.12 in B-CLL cells obtained from B-CLL patients as measured by flow cytometry.
Figure 11:
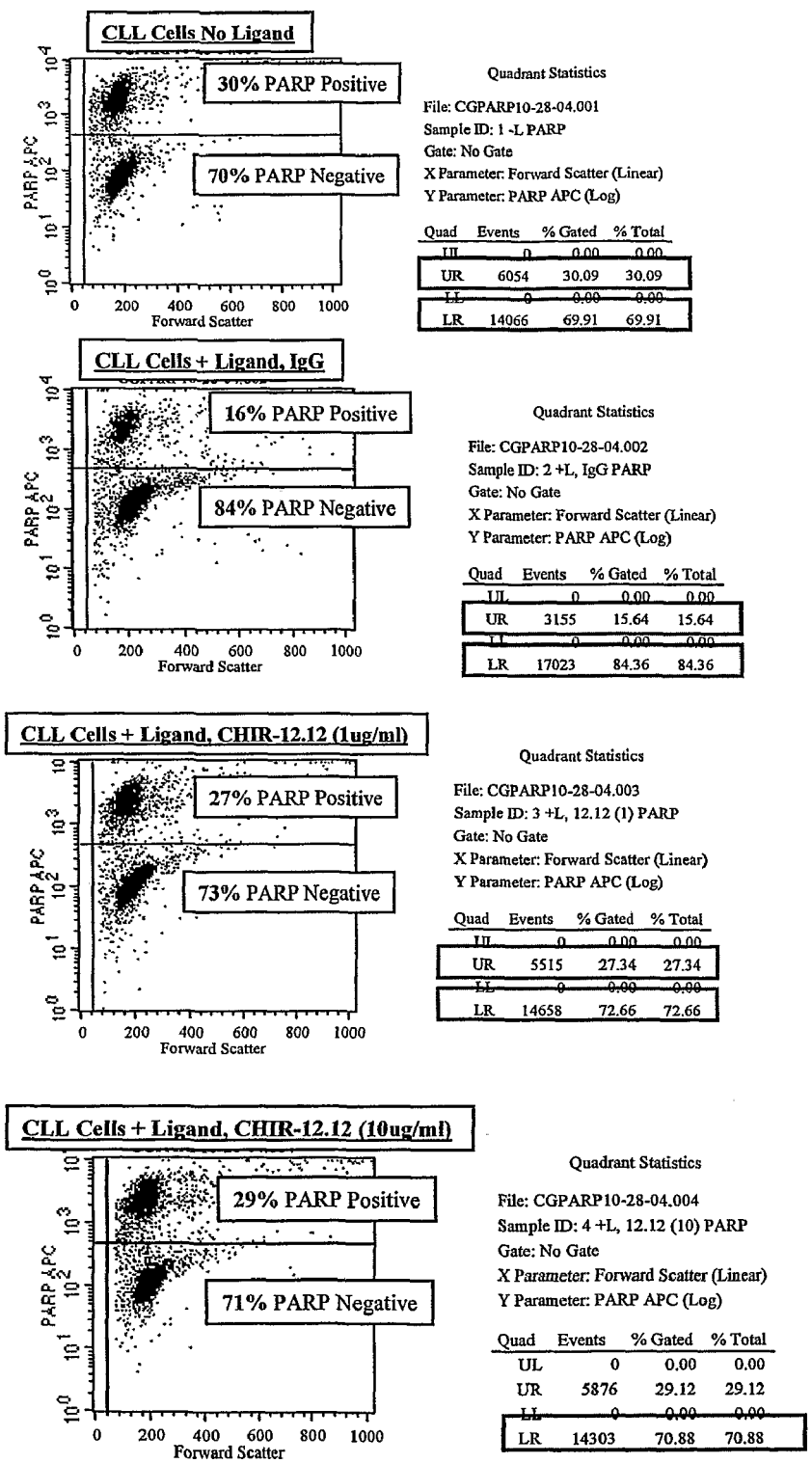
FIG. 11 shows inhibition of CD40L-mediated survival (cleaved PARP) by CHIR-12.12 in B-CLL cells obtained from B-CLL patients as measured by flow cytometry.

Flow cytometry analysis on cells treated with CHIR12.12 is shown in FIGS. 10 and 11. Cleaved PARP and TUNEL methods were used to assess apoptosis. After culturing cells for 24 hrs in the absence of sCD40L, the cells began to show signs of apoptosis, resulting in cells staining positive for cleaved PARP and TUNEL. The addition of sCD40L induced a decrease in the percentage of cells that stained positive for these two markers. When CHIR-12.12 was added in conjunction with sCD40L, the percentage of positive cells for cleaved PARP or TUNEL returned to the levels seen without sCD40L stimulation. This indicates that the survival induced by sCD40L is inhibited by the addition of CHIR-12.12.

Effect of CHIR 12.12 Treatment on CD40 Ligand-Mediated Signaling Events in B-CLL Cells at the Transcript Level.

CHIR-12.12 was used in a timecourse to determine how it mediates transcriptional regulation in B-CLL cells. In this experiment, $1.0 \times 10^6$ B-CLL cells from patients were simultaneously treated with IgG1 (10 µg/mL) or CHIR-12.12 (10 µg/mL) and sCD40L. Cell pellets were collected at 0 hr (no CD40L), 1, 4 and 24 hr and lysed simultaneously at the end. RNA was isolated using the RNeasy kit, and cDNA was prepared using the ABI RT kit. Two-step RT-PCR was done with the genes shown in two separate reactions, based on $T_M$ of each set of oligos.

Figure 12:
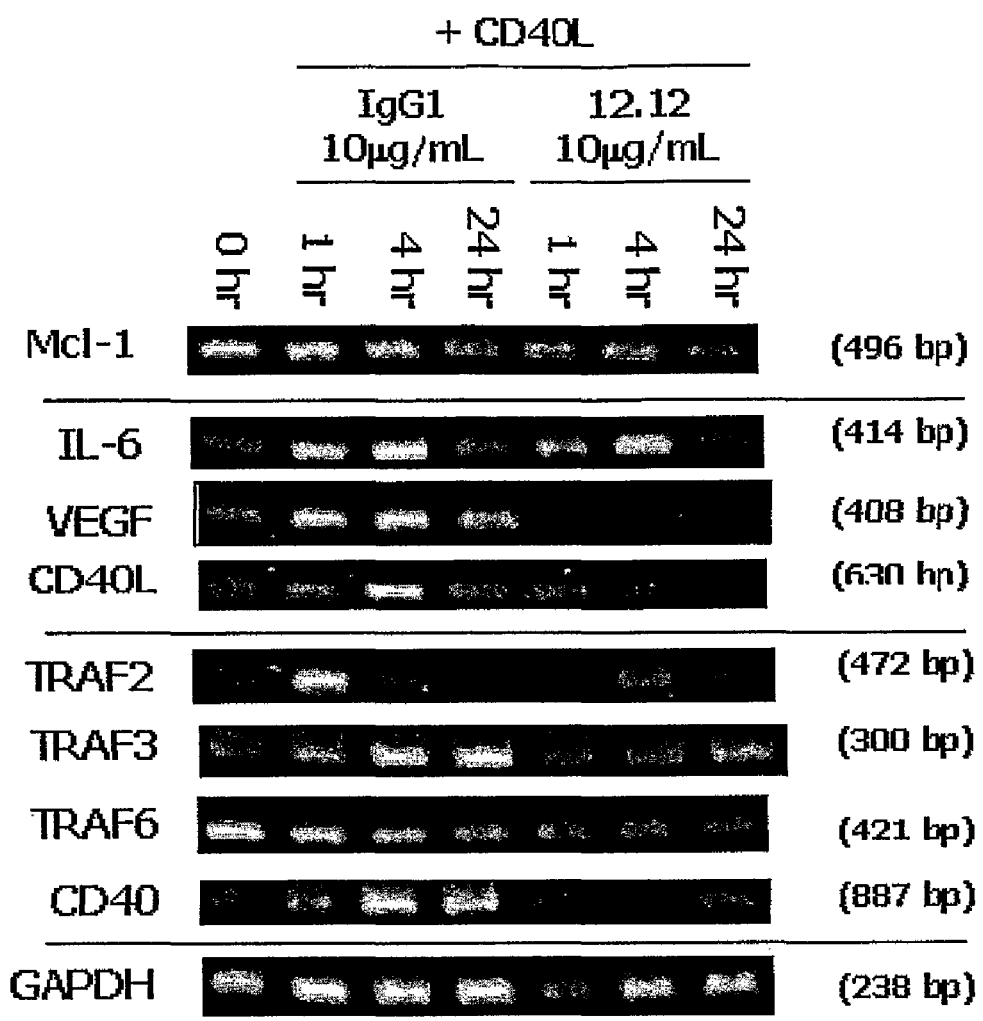
FIG. 12 shows the effect of CHIR-12.12 on B-CLL cell markers at the transcript level.

Various genes showed CHIR-12.12-mediated transcriptional changes at certain timepoints when compared to the IgGI control samples (FIG. 12). CD40, CD40L, VEGF, TRAF2, and TRAF3 all showed inhibition of RNA expression, with TRAF6 and Mcl-1 showing minor down-regulation. IL-6 showed no transcriptional changes.

CHIR-12.12 Treatment Inhibits CD40 Ligand-Mediated p38 MAPK Signaling in B-CLL Cells.

A p38 MAPK inhibitor (SB203580) and CHIR-12.12 were used at two different timepoints, 4 hours and 24 hours, to dissect the role of the p38 MAPK pathway in CD40 signaling. In the four-hour experiment, approximately $0.8 \times 10^6$ B-CLL cells per well were serum starved in 1% FBS-containing media for 4 hours. Cells were pretreated with SB203580 (30 and 60 µM) and CHIR-12.12 (10 µg/mL). Cell lysates were collected before and 20 minutes after CD40L stimulation. Western blot analysis with antibodies against specific proteins shown were conducted, and equal loading was evaluated by probing with antibodies to total p38 (t-p38) and β-actin.

In the 24-hour experiment, approximately $0.8 \times 10^6$ B-CLL cells per well were placed in full serum (10% FBS)-containing media for 24 hours. Cells were simultaneously pretreated with either SB203580 (30 and 60 µM) or CHIR-12.12 (10 µg/mL) for 24 hours and stimulated with CD40L. Western blot analysis with antibodies against specific proteins shown was conducted, and equal loading was evaluated by probing with antibodies against β-actin.

Figure 13:
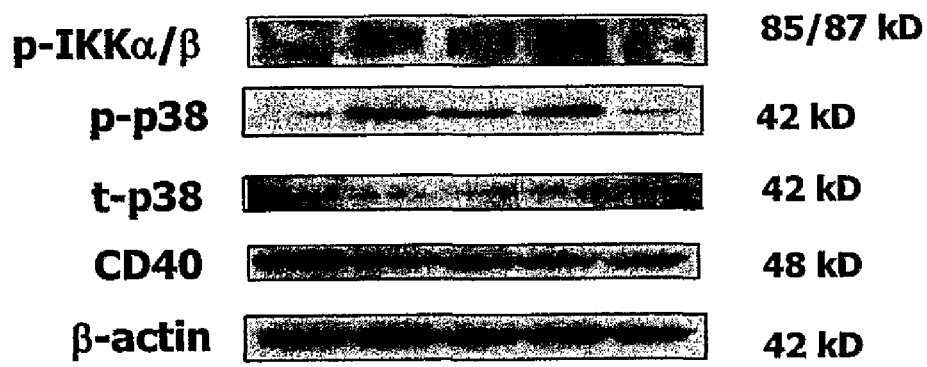
FIG. 13 shows the effect of CHIR-12.12 and the p38 MAPK inhibitor SB203580 on CD40L-mediated CD40 signaling via the p38 pathway at 4 hr.

FIG. 13 shows that p38 was not constitutively phosphorylated in this patient, however, the constitutive activity has been variable between patients. Its activation by CD40L was slightly inhibited by SB203580 inhibitor and fully inhibited by CHIR-12.12 at 4 hours. Phospho-IKKα/β activation by CD40L was also inhibited by CHIR12.12.

Figure 14:
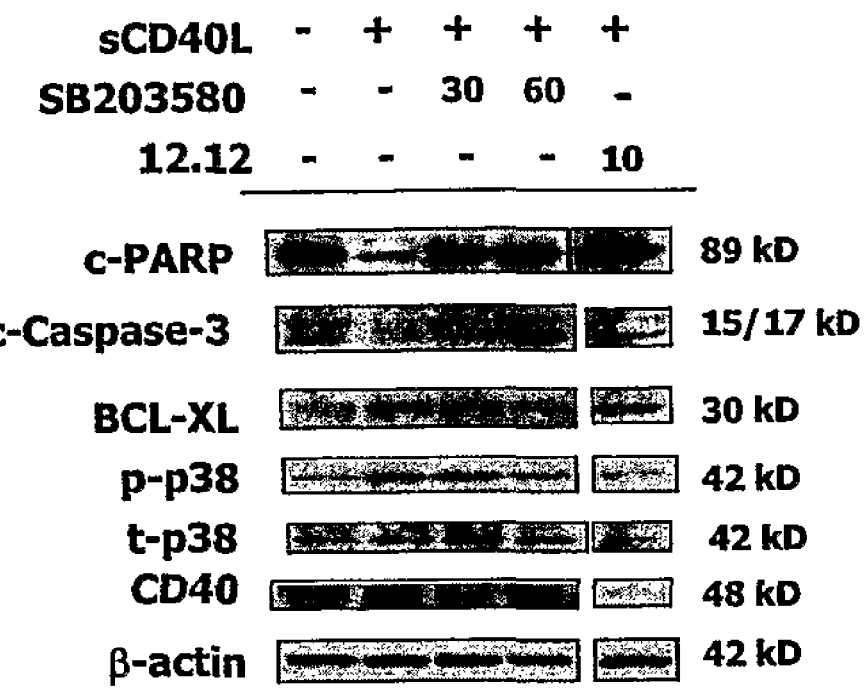
FIG. 14 shows the effect of CHIR-12.12 and the p38 MAPK inhibitor SB203580 on CD40L-mediated CD40 signaling via the MEK/p38 pathway at 24 hr.

As shown in FIG. 14, cleaved-PARP was significantly induced by both SB203580 and CHIR.12.12, thereby inhibiting CD40L-mediated stimulation, while cleaved Caspase-3 was induced to a lesser extent. Bcl-xl expression was also blocked, especially at the 60 µM concentration of SB203580 and 10 µg/ml of CHIR-12.12; p38 phosphorylation was similarly blocked as was seen in the 4 hour experiment. CD40 expression also was inhibited by CHIR-12.12.

Figure 15:
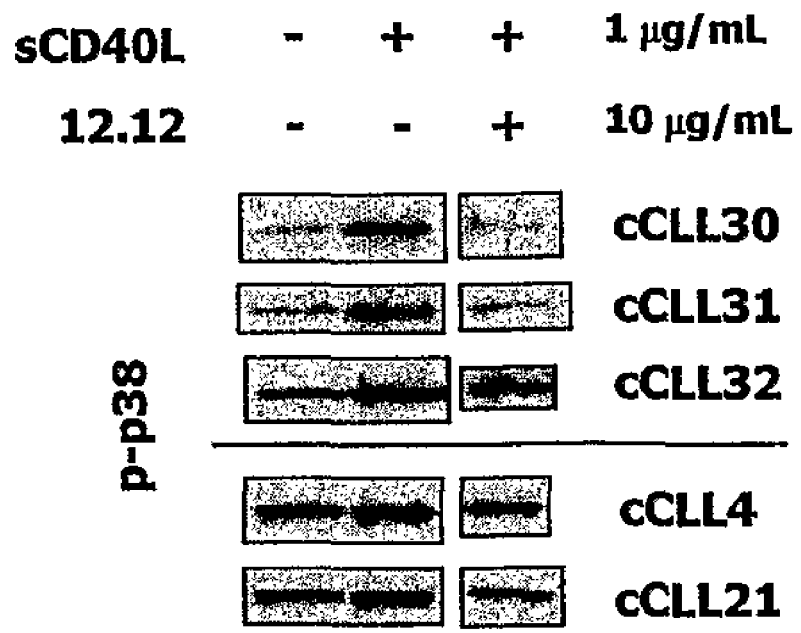
FIG. 15 shows p-p38 status in multiple B-CLL patients.

FIG. 15 shows that p38 basal phosphorylation status varies among the CLL patient samples that have been tested. Patients with low basal p-p38 activity have a higher induction of phosphorylation by CD40L stimulation than patients with a higher basal expression. CHIR-12.12 lowered p-p38 levels back to basal phosphorylation regardless of whether that basal level was high or low.

Example 2

Ability of Anti-CD40 mAb CHIR-12.12 to Lyse Multiple Myeloma (MM) Cell Lines by Antibody-Dependent Cellular Cytotoxicity (ADCC)

Human MM cell lines, KMS-12-BM, IM-9, and ARH-77, were washed 3 times using R2 medium (Pheno red-free RPMI with 2% FBS) and re-suspended in R10 medium (Pheno red-free RPMI with 10% FBS) at the density of $1 \times 10^6$/mL. Cells were labeled by adding Calcein AM (final concentration 5 mM) and incubating for 30 minutes at 37° C. in a humidified atmosphere with 5% $CO_2$. Purified human NK cells and Calcein-labeled target cells were mixed in R10 medium at the ratio of 10 to 1 ($5 \times 10^4$ NK cells and $5 \times 10^3$ target cells in 200 mL) and added in U-bottom 96 well plate (Packard's Instrument, Meriden, Conn.). CHIR-12.12 was serial diluted at desired concentration and added in triplicates into the wells containing NK/target cell mixture. 1% NP-40 was added in 3 wells for the maximum cell lysis. Cells were incubated for 4 hours without disturbance at 37° C. in a humidified atmosphere with 5% CO2. The plate was then centrifuged at 300 rpm without brake for 5 minutes. 100 mL supernatant was transferred into a new 96 well plate. The released Calcein in the supernatant was measured in arbitrary fluorescent unit (AFU) at 485 nm excitation and 535 nm emission using Tecan SpectraFluor Plus (Tecan U.S., Inc., Research Triangle, N.C.). The percent of specific lysis was calculated as: 100× (AFU test−AFU spontaneous release)/(AFU maximal release−AFU spontaneous release).

Figure 16:
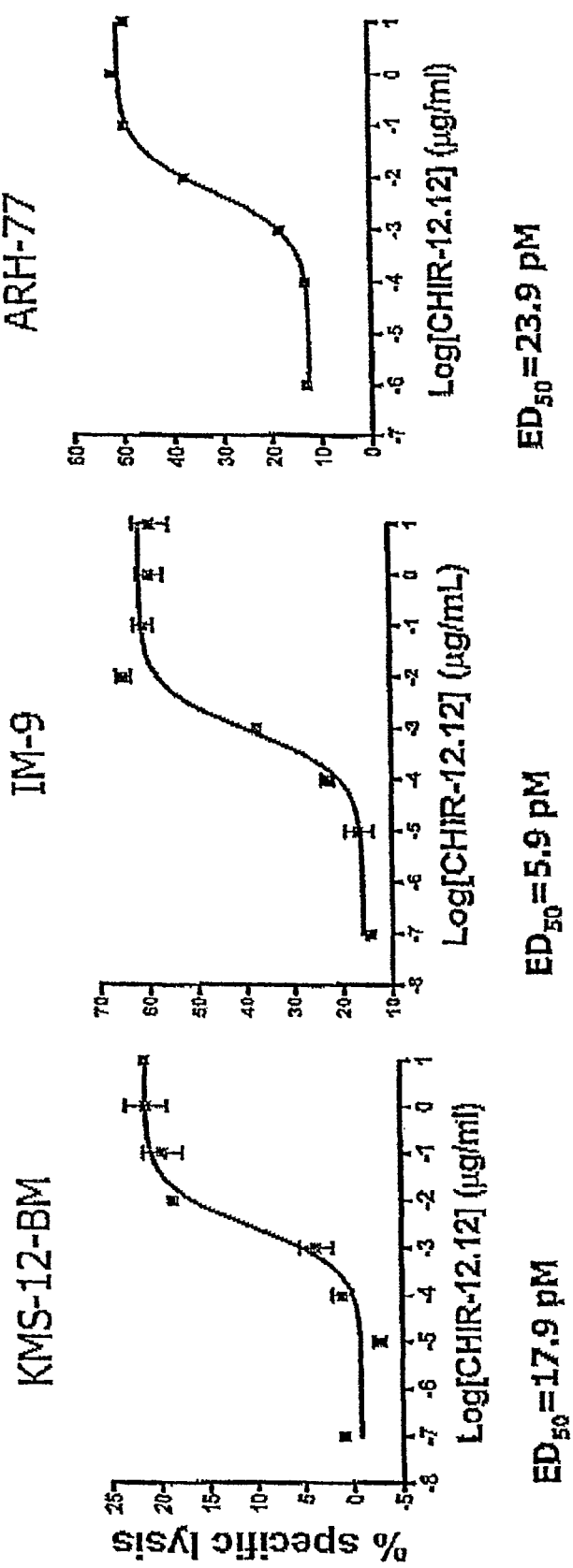
FIGS. 16A, B, and C show the CHIR-12.12-mediated antibody-dependent cellular cytotoxicity (ADCC) against human multiple myeloma cell lines KMS-12-BM (FIG. 16A), IM-9 (FIG. 16B), or ARH-77 (FIG. 16C).

The $ED_{50}$ was determined for each cell line by plotting the log of antibody concentration versus the percent specific lysis (see FIG. 16). The $ED_{50}$ of CHIR-12.12 for KMS-12-BM cells was 17.9 mM; the $ED_{50}$ of CHIR-12.12 for IM-9 cells was 5.9 pM, and the $ED_{50}$ of CHIR-12.12 for ARH-77 cells was 23.9 pM.

Example 3

CHIR-12.12 Anti-Tumor Activity in Multiple Myeloma Animal Models

When administered intraperitoneally (i.p.) once a week for a total of 3 doses, CHIR-12.12 significantly inhibited the growth of multiple myeloma tumors in several tumor models in a dose-dependent manner. When CHIR-12.12 was combined with bortezomib (VELCADE®) the efficacy observed was additive.

IM-9 Multiple Myeloma Xenograft Model

SCID mice were inoculated subcutaneously with IM-9 tumor cells (a human multiple myeloma cell line expressing both CD40 and CD20) in 50% MATRIGEL™ at $5 \times 10^6$ cells per mouse. In the first study, tumor-bearing mice were injected intraperitoneally with control $IgG_1$ at 10 mg/kg, CHIR-12.12 anti-CD40 mAb at 1 mg/kg, or CHIR-12.12 anti-CD40 mAb at 10 mg/kg on days 5, 12, and 18 after tumor implantation. Alternatively, bortezomib dosing at 1 mg/kg intravenously occurred on days 5, 8, 12, and 15 after tumor implantation. In the second study, tumor-bearing mice were injected with control $IgG_1$ at 1 mg/kg intraperitoneally, CHIR-12.12 anti-CD40 mAb at 1 mg/kg intraperitoneally, or bortezomib at 1 mg/kg intravenously. Antibody dosing occurred on days 8, 14, and 21 post tumor implantation, while bortezomib dosing occurred on days 8, 11, 14 and 18 post tumor implantation. Alternatively, tumor-bearing mice were injected with CHIR-12.12 anti-CD40 mAb at 1 mg/kg intraperitoneally on days 8, 14, and 21 post tumor implantation plus bortezomib at 1 mg/kg intravenously on days 8, 11, 14, and 18 post tumor implantation. Data were analyzed using the log-rank test.

Figure 17:
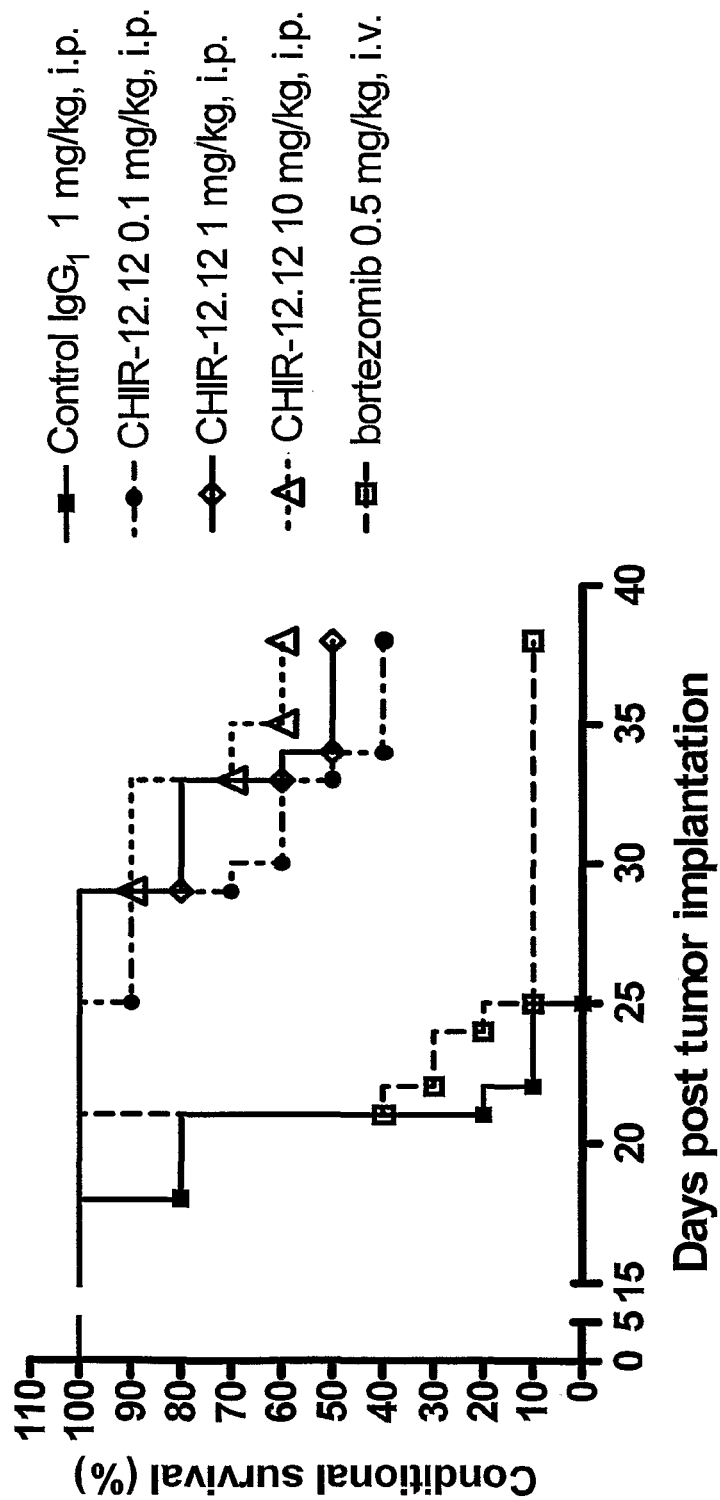
FIG. 17 shows the tumor volume in a multiple myeloma animal model over time in animals administered with control IgG$_1$ at 10 mg/kg, i.p. (●), CHIR-12.12 anti-CD40 mAb at 1 mg/kg, i.p. (○), CHIR-12.12 anti-CD40 mAb at 10 mg/kg, i.p. (*), or bortezomib at 1 mg/kg, i.v. (Δ). The upward arrows indicate bortezomib dosing, and the downward arrows indicate CHIR-12.12 dosing.

Administration of CHIR-12.12 at 1 and 10 mg/kg inhibited tumor growth at 15, 18, and 21 days post tumor implantation (see FIG. 17). Bortezomib, when administered at 1 mg/kg on days 5, 8, 12, and 15, after tumor implantation also inhibited tumor growth at 15, 18, and 21 days post tumor implantation (see FIG. 17). In the second study, 1 mg/kg bortezomib did not display statistically significant growth inhibition. When CHIR-12.12 was administered (1 mg/kg) in combination with the maximally tolerated dose of bortezomib, a tumor volume reduction was observed on days 13, 16, 20, 23, and 26 (see FIG. 18).

Figure 18:
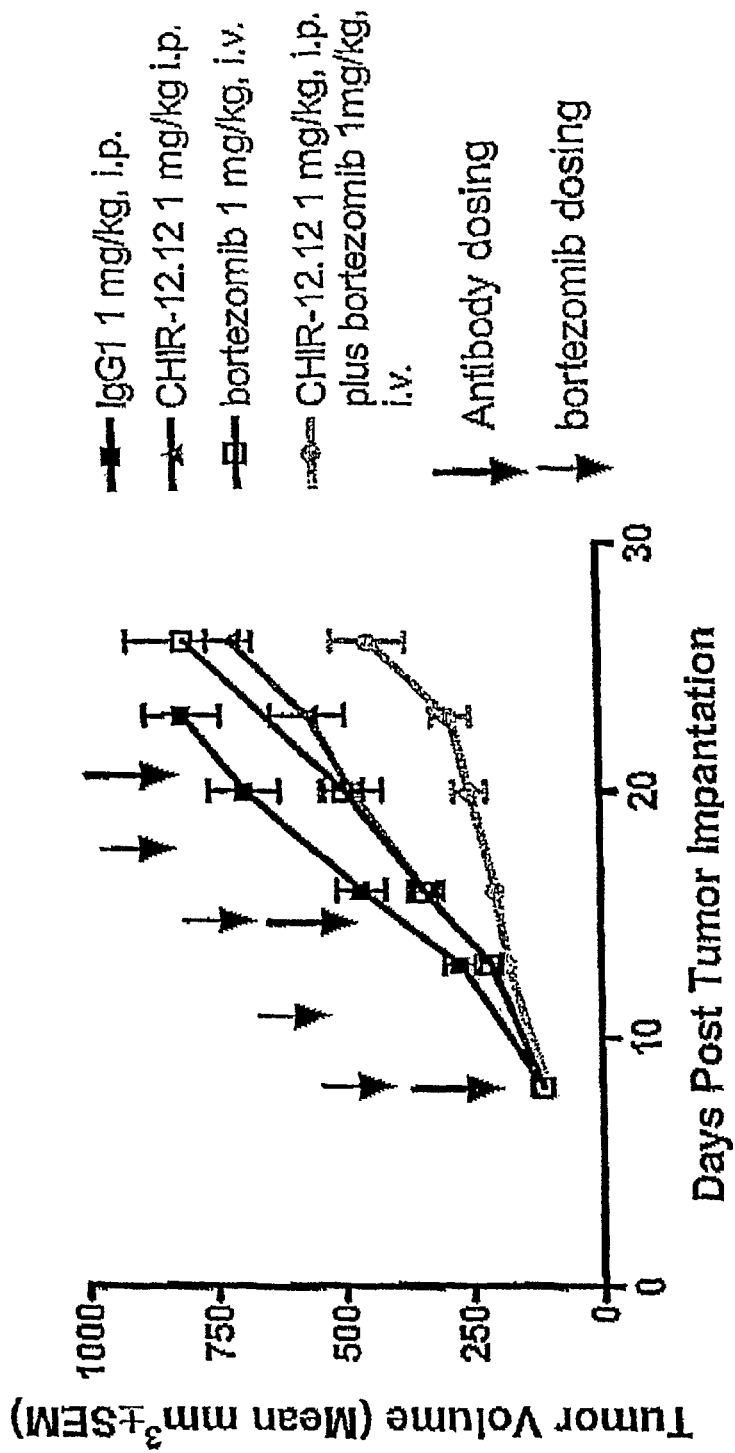
FIG. 18 shows the tumor volume in a multiple myeloma animal model over time in animals administered with control IgG$_1$ at 1 mg/kg (■), CHIR-12.12 anti-CD40 mAb at 1 mg/kg (▲), bortezomib at 1 mg/kg (□), or CHIR-12.12 anti-CD40 mAb at 1 mg/kg plus bortezomib at 1 mg/kg (○). The larger arrows indicate antibody dosing, and the smaller arrows indicate bortezomib dosing.
Figure 19:
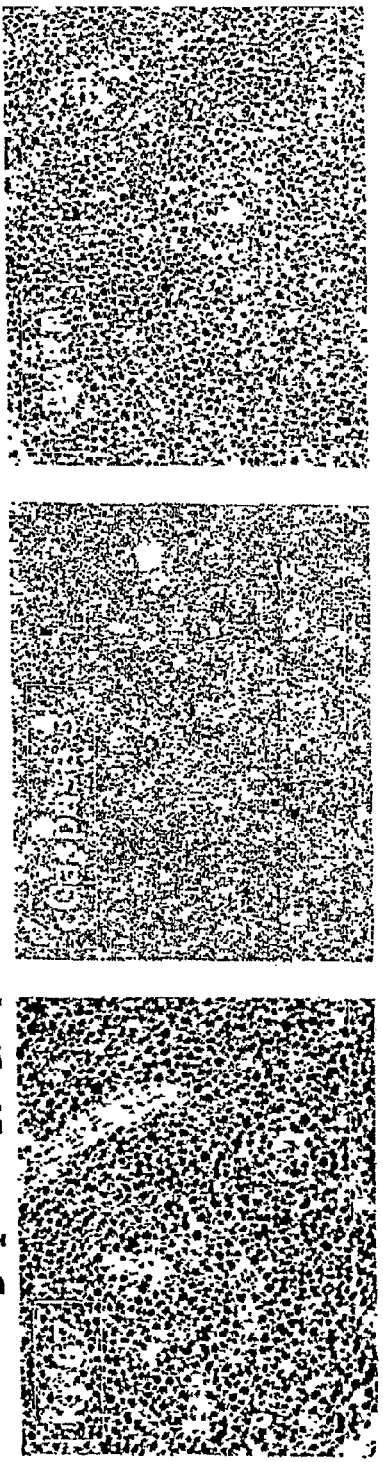
FIG. 19 shows the effect of CHIR-12.12 anti-CD40 mAb on tumor cell proliferation in the human multiple myeloma xenograft model IM-9, assayed by immunohistochemical staining for Ki67 expression, and induction of cell death as evidenced by an increased level of the apoptotic biomarkers cleaved-Caspase 3 and cleaved-PARP.
Figure 19:
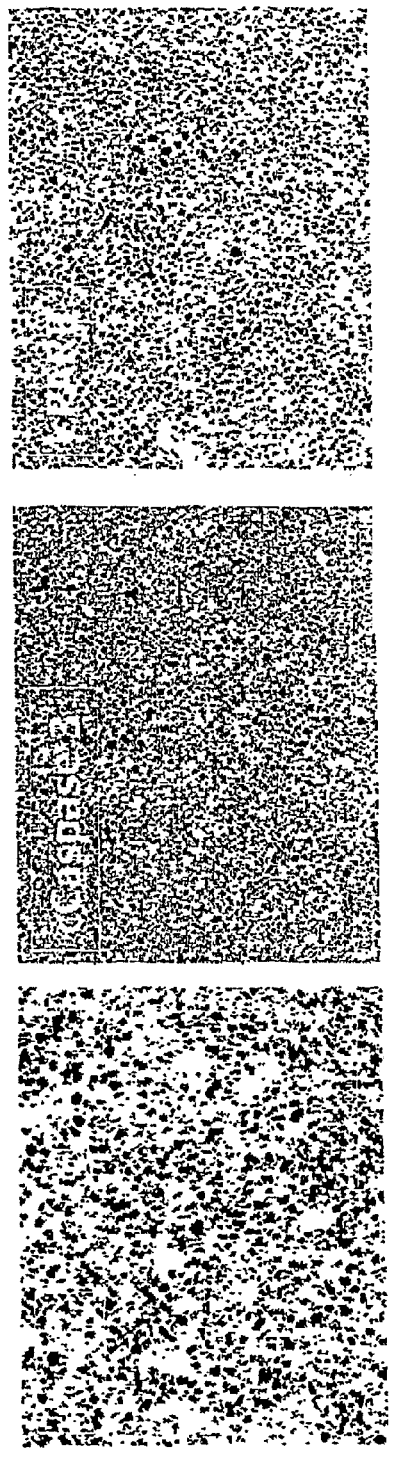

In summary, anti-CD40 mAb CHIR-12.12 administration inhibited tumor growth in experimental multiple myeloma models at 1 mg/kg and 10 mg/kg administered weekly. Bortezomib at 1 mg/kg twice a week demonstrated borderline activity as the tumor growth inhibition in one experiment was statistically significant (FIG. 17) and in the second study it was not (FIG. 18). Further, combining CHIR-12.12 with bortezomib treatment enhanced the inhibition of tumor growth. These data suggest that the anti-CD40 mAb CHIR-12.12 has potent anti-tumor activity and could be clinically effective for the treatment of multiple myeloma, either alone or in combination with other chemotherapeutic agents.

CHIR-12.12 Reduces Proliferation Rate and Increases Cell Death in IM-9 Xenografts.

When CHIR-12.12 was tested in the subcutaneous IM-9 xenograft model, histology was performed 5 days after a single dose of CHIR-12.12. CHIR-12.12 treatment significantly reduced the number of $Ki67^+$ proliferating cells and increased the level of cleaved caspase 3 and cleaved PARP, two apoptosis markers, demonstrating the inhibition of cell proliferation and induction of cell death resulted from CHIR-12.12 treatment.

CHIR-12.12 Prolongs Survival in the Unstaged or Staged Orthotopic (i.v.) IM-9 Xenograft Model.

SCID mice were inoculated subcutaneously with IM-9 tumor cells (a human multiple myeloma cell line expressing both CD40 and CD20) in 50% MATRIGEL™ at $5 \times 10^6$ cells per mouse. In unstaged models, treatment was initiated one day after tumor implantation. Tumor-bearing mice were injected with control $IgG_1$ at 10 mg/kg or anti-CD40 mAb CHIR-12.12 at 0.1 mg/kg, 1 mg/kg or 10 mg/kg intraperitoneally once a week. Alternatively, tumor-bearing mice were injected with bortezomib at 0.5 mg/kg or 1 mg/kg intravenously once a week. Data were analyzed using the log-rank test.

Figure 20:
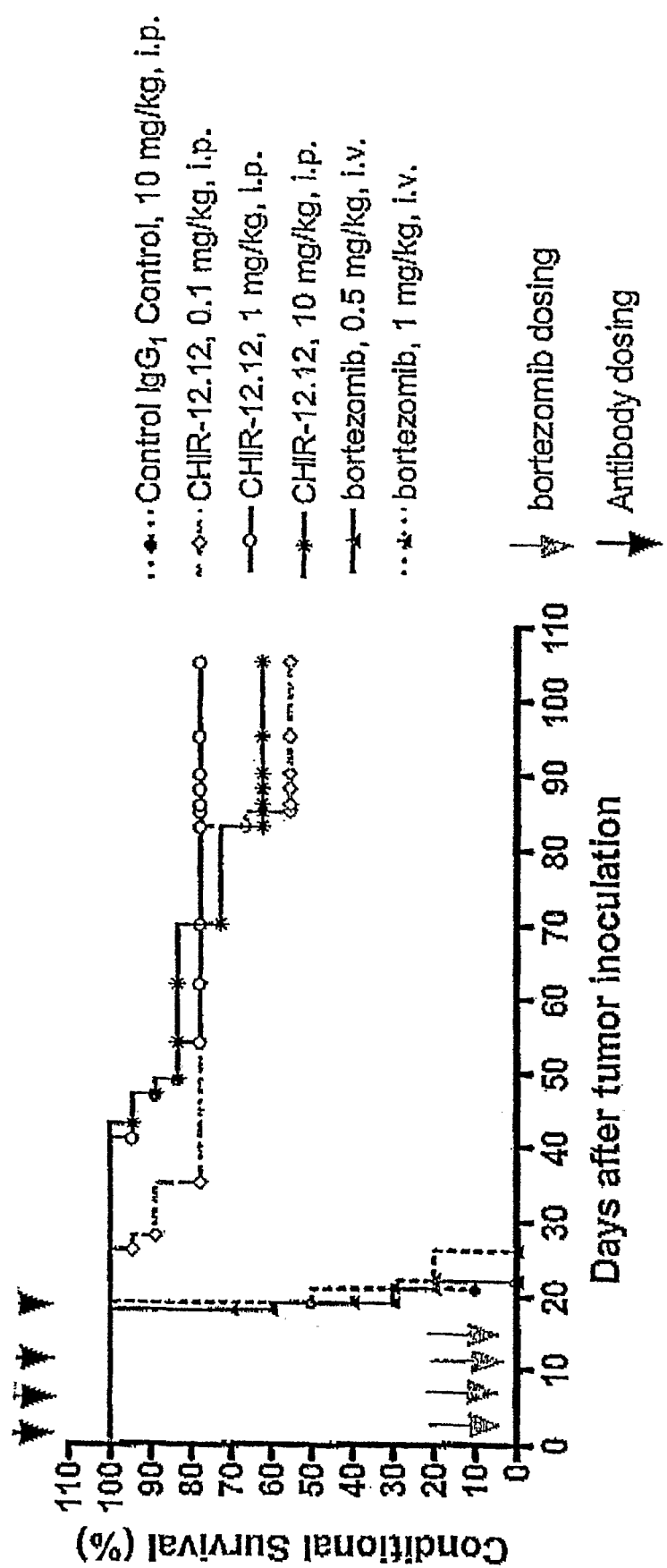
FIG. 20 shows the conditional survival rate over time in an unstaged orthotopic IM-9 xenograft model in animals administered with control IgG$_1$ at 10 mg/kg (●), anti-CD40 mAb CHIR-12.12 at 0.1 mg/kg (◇), 1 mg/kg (○), 10 mg/kg (◆), or bortezomib at 0.5 mg/kg (-▲-) or 1 mg/kg ( . . . ▲ . . . ). The shaded arrows indicate bortezomib dosing, and the solid arrows indicate antibody dosing.
Figure 21:
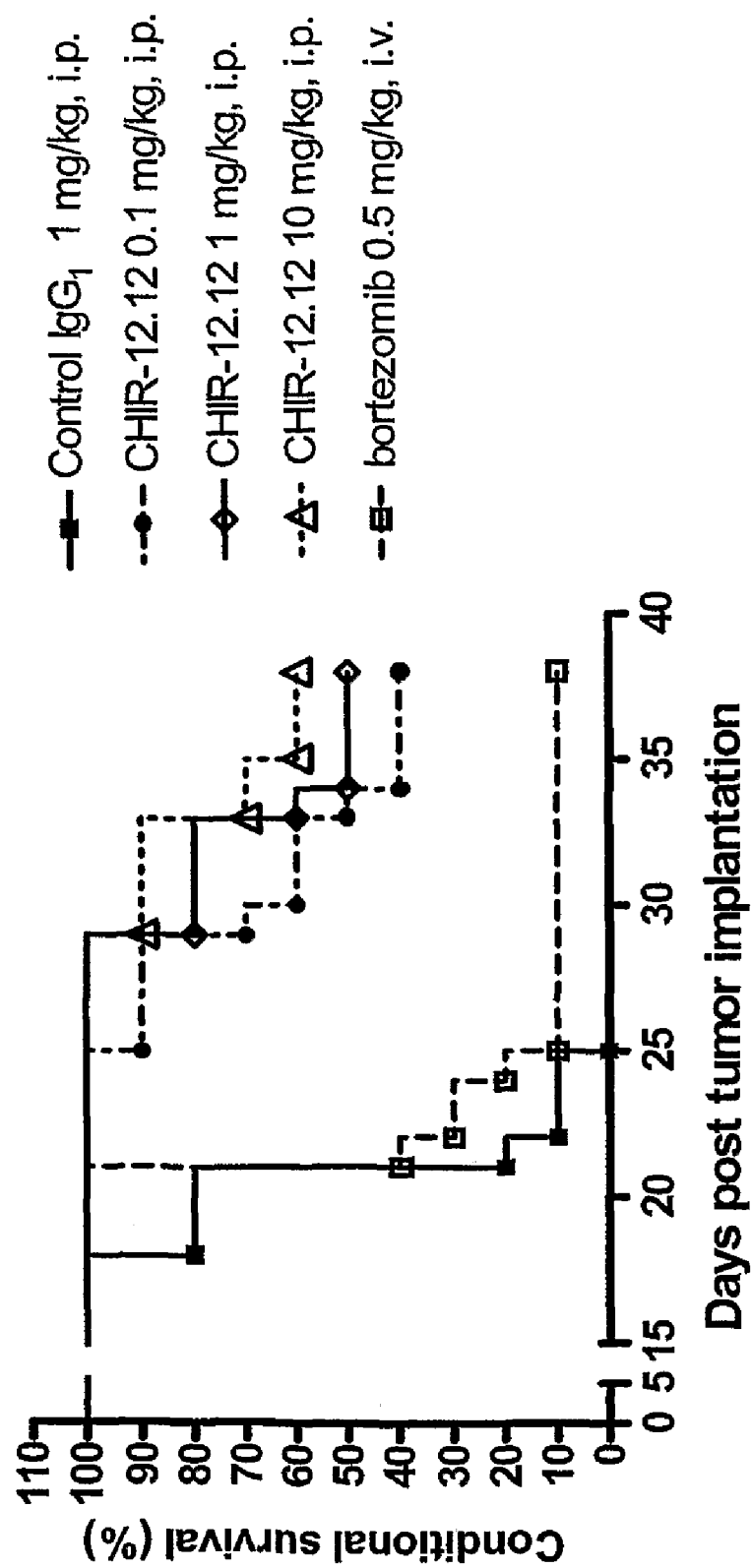
FIG. 21 shows conditional survival rate over time in a staged orthotopic IM-9 xenograft model in animals administered with control IgG$_1$ at 1 mg/kg, i.p. (■), anti-CD40 mAb CHIR-12.12 at 0.1 mg/kg, i.p (●), 1 mg/kg, i.p. (-◇-), or 10 mg/kg, i.p (Δ), or bortezomib at 0.5 mg/kg, i.v. (□).
Figure 22:
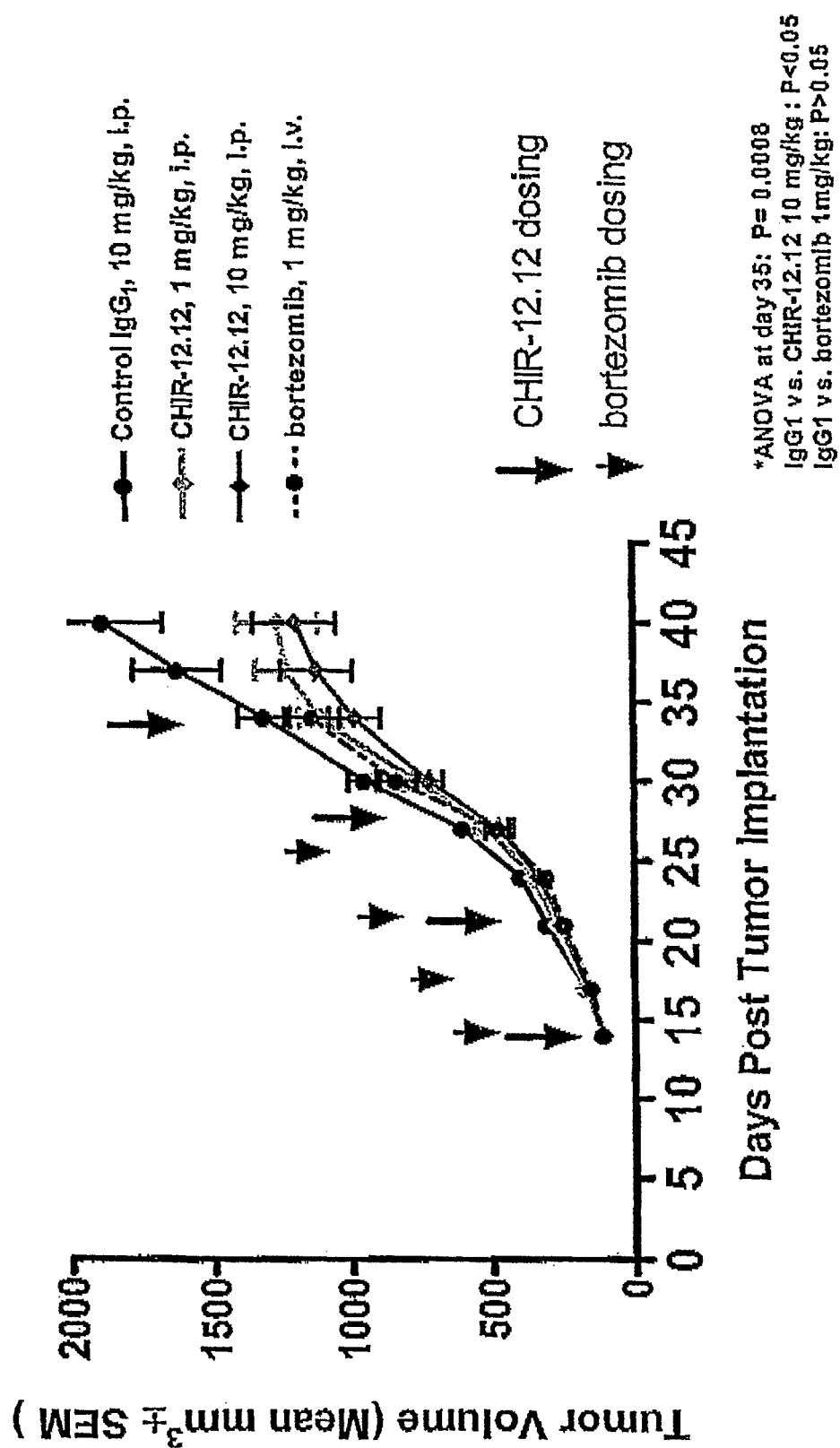
FIG. 22 shows the tumor volume in a human multiple myeloma subcutaneous xenograft model over time in animals administered with control IgG$_1$ at 10 mg/kg, i.p. (●), CHIR-12.12 anti-CD40 mAb at 1 mg/kg, i.p. (◇), CHIR-12.12 anti-CD40 mAb at 10 mg/kg, i.p. (◆), or bortezomib at 1 mg/kg, i.v. ( . . . ● . . . ). The larger arrows indicate CHIR-12.12 dosing, and the smaller arrows indicate bortezomib dosing.

In an unstaged conditional survival model, CHIR-12.12 prolonged the survival of tumor-bearing mice (FIG. 20). In staged models, treatment was initiated 7 days after tumor cell implantation. Tumor-bearing mice were injected with control IgG1 at 1 mg/kg or anti-CD40 mAb CHIR-12.12 at 0.1 mg/kg, 1 mg/kg, or 10 mg/kg intraperitoneally once a week. Alternatively, tumor-bearing mice were injected with bortezomib at 0.5 mg/kg intravenously. Data were analyzed using the log-rank test. In this staged orthotopic model, CHIR-12.12 also prolonged survival of tumor-bearing mice (FIG. 21).

CHIR-12.12 Inhibits Growth of Human KMS-12-BM Subcutaneous Xenograft Model.

Female SCID mice were treated with 3Gy irradiation one day prior to implantation of tumor cells. On the day of implantation, cells were prepared at a concentration of $5 \times 10^7$ cells/ml in 50% matrigel. Cells were implanted subcutaneously over the right flank at $5 \times 10^6$ cells/100 µl/mouse. When tumor volume reached 100~200 $mm^3$, mice were randomized and treated with either $IgG_1$ isotype control antibody at 10 mg/kg, anti-CD40 antibody CHIR-12.12 at 1 mg/kg or 10 mg/kg, or bortezomib at 1 mg/kg. Antibodies were administered intraperitoneally once a week for 4 weeks. Bortezomib was administered intravenously twice a week for two weeks.

Primary tumor growth was dose-dependently inhibited by administration of CHIR-12.12 at 42 days post cell implantation. The KMS-12-BM tumor volume was reduced 32% ($P>0.05$, Anova followed by Tukey multi-comparison test) and 35% ($P<0.05$) in 1 mg/kg and in 10 mg/kg groups, respectively. Bortezomib only showed a trend toward inhibition, with tumor volume reduction of 22% ($P>0.05$) at the maximal tolerated dose of 1 mg/kg.

Example 4

Evaluation of CD40 Ligand-Induced Cytokine Secretion in CD40+ Cells

CD40 is highly expressed in B cell malignancies. Stimulation of CD40 by its ligand provides survival and proliferative signals for normal and malignant B cells. The antagonist anti-CD40 antibody CHIR-12.12 does not induce the proliferation of human peripheral blood lymphocytes but inhibits CD40L-induced lymphocyte proliferation. CD40 signaling also induces cells to produce a variety of cytokines. In this example, the ability of CHIR-12.12 to modulate cytokine production by normal B cells and primary patient CLL cells was investigated.

Cells ($1\times10^5$ cells per well) were cultured in a 96-well plate in the presence or absence of CD40L (CD40 transfected, formaldehyde fixed CHO cells, $2\times10^5$ per well). Cells were incubated with huIgG1 (control) or CHIR-12.12 at 10 µg/ml at 37 C for 24 hours, and supernatants were harvested. Production of hIL-6, hIL-8, hIL-10, hTNF-α, hGM-CSF, hIL-1b, hIL-12p70, MCP-1, and MIP-1β was measured by Meso Scale Discovery® multi-array system (Meso Scale Discovery, Gaithersburg, Md.).

Cells cultured with CHIR-12.12 alone in the absence of CD40L did not produce any of the cytokines above background levels suggesting that CHIR-12.12 does not have an agonistic activity for cytokine production. In contrast CD40L-induced production of hIL-10, hTNF-α, hIL-8, hIL-6, MCP-1, and MIP-1β in normal B cells (n=3) (Table 2). Addition of CHIR-12.12 to these cultures inhibited production of all cytokines (see Table 3).

TABLE 2

CD40L-induced cytokine secretions from normal B cells (values are folds of induction over background).

| Cytokine | Donor 1 | Donor 2 | Donor 3 |
|---|---|---|---|
| hIL-1b | no induction | no induction | no induction |
| hIL-12p70 | no induction | ND | no induction |
| hIL-10 | 3.6 | ND | 3.6 |
| hGM-CSF | no induction | ND | no induction |
| hTNF-α | 3.7 | 4.8 | 22.8 |
| hIL-8 | 7.7 | 14.7 | 49.3 |
| hIL-6 | 5.7 | 3.8 | 20.5 |
| MCP-1 | 5.5 | not tested | 1.7 |
| MIP-1β | 2.2 | 2.6 | 17.8 |

TABLE 3

CHIR-12.12 inhibits secretion from normal B cells of all cytokines induced by CD40L (values are % inhibition).

| Cytokine | Donor 1 | Donor 2 | Donor 3 |
|---|---|---|---|
| hIL-1b | no induction | no induction | no induction |
| hIL-12p70 | no induction | ND | no induction |
| hIL-10 | 90.5 | ND | 94.4 |
| hGM-CSF | no induction | ND | no induction |
| hTNF-α | 92.8 | 97.4 | 98.5 |
| hIL-8 | 98.2 | 84.7 | 99.5 |
| hIL-6 | 92.2 | 99.9 | 99.3 |
| MCP-1 | 55.3 | not tested | 25.7 |
| MIP-1β | 54.4 | 92 | 92.5 |

In preliminary experiments with CLL patient cells, CHIR-12.12 inhibited CD40L-induced production of hIL-10, hGM-CSF, hTNF-α, hIL-8 and MCP-1 (n=1) (Table 4 versus Table 5).

TABLE 4

CD40L-induced cytokine secretions by CLL cells (values are folds of induction over background).

| Cytokine | CLL #1 |
|---|---|
| hIL-1b | no induction |
| hIL-12p70 | ND |
| hIL-10 | 9.2 |
| hGM-CSF | 7.6 |
| hTNF-α | 3.3 |
| hIL-8 | 4.0 |
| hIL-6 | no induction |
| MCP-1 | 5.5 |
| MIP-1β | no induction |

TABLE 5

CHIR-12.2 inhibits secretion by CLL cells of all cytokines induced by CD40-ligand (values are % inhibition).

| Cytokine | CLL #1 |
|---|---|
| hIL-1b | no induction |
| hIL-12p70 | ND |
| hIL-10 | 99.6 |
| hGM-CSF | 86.5 |
| hTNF-α | 89.6 |
| hIL-8 | 91.0 |
| hIL-6 | no induction |
| MCP-1 | 34.8 |
| MIP-1β | no induction |

Together, these data show that CHIR-12.12 is a potent antagonist for CD40-ligand mediated survival, proliferation, and cytokine production.

CD40 ligation can also induce the expression of VEGF in normal (Melter et al. (2000) *Blood* 96(12):3801-3808) and neoplastic cells (Farahani et al. (2005) *Leukemia* 19(4):524-530; Tai et al. (2005) *Cancer Res.* 65(13):5898-5906). VEGF has been shown to promote cell growth and migration in multiple myeloma cells (Podar et al. (2001) *Blood* 98(2):428-435) and to promote cell survival in CLL cells (Farahani et al. (2005), supra). As such, changes in VEGF levels may provide a useful cytokine marker of CD40L-mediated CD40 signaling. Because VEGF is a secreted protein, changes in VEGF protein expression can be easily detected in cell culture supernatants or in plasma obtained from patient blood samples using techniques such as Western blot or ELISA. Alternatively it can be detected from the mRNA obtained from tumor cells, using any of a number of techniques such as Northern blot or quantitative-RT-PCR.

In another experiment, CD40L-induced production of VEGF in normal B cells and CLL cells obtained from patients with CLL is examined in a manner similar to that described above. Addition of CHIR-12.12 to these cell cultures is found to inhibit CD40L-induced production of VEGF.

Example 5

Biomarkers and Prognostic Indicators

The ex vivo prognostic assays and additional prognostic assays to be used in the methods of the present invention require screening biological samples for the level of expression of biomarkers whose mature protein sequences and nucleotide sequences are known in the art. See for example, the information shown in Table 3 below. It is recognized that probes for detecting these biomarkers, either at the protein (for example, antibody probes) or nucleic acid level (for example, PCR probes), can be designed based on this sequence information, and that probes can be designed to detect variants of the sequences disclosed herein.

TABLE 6

Amino Acid and Nucleotide Sequences for Biomarkers and Prognostic Markers.

| Biomarker Name | Accession No. | Accession No. |
|---|---|---|
| AKT-1 | NM_005163 | NP_005154 |
| AKT-2 | NM_001626 | NP_001617 |
| AKT-3 | AF135794 | AAD24196 |
| PI3K | Y13892 | CAA74194 |
| PDK1 | BC006339 | AAH06339 |
| IKKα | AF012890 | AAC51662 |
| IKKβ | AF031416 | AAC64675 |
| IκB | BT006743 | Q15653 |
| NF-κB | NM_003998 | NP_003989 |
| MEK1 | L11284 | |
| | NM_002755 | NP_002746 |
| MEK2 | L11285 | |
| | NM_030662 | NP_109587 |
| MEK3 | NM_002746 | NP_002737 |
| MEK6 | U49732 | AAB05055 |
| ERK1 | NM_002746 | NP_002737 |
| ERK2 | NM_002745 | NP_002736 |
| p38 | L35253 | AAA74301 |
| Caspase 3 | NM_004346 | NP_004337 |
| Caspase 7 | BT006683 | AAP35329 |
| Caspase 9 | BT006911 | AAP35557 |
| PARP | NM_001618 | NP_001609 |
| Bcl-2 | M14745 | AAA35591 |
| Bcl-xl | Z23115 | CAA80661 |
| Mcl-1 | AF118124 | AAD13299 |
| XIAP | U45880 | AAC50373 |
| cIAP1 | U45879 | AAC50372 |
| survivin | U75285 | AAC51660 |
| TRAF-1 | NM_005658 | NP_005649 |
| Ki67 | X65550 | CAA46519 |
| ZAP70 | BC039039 | AAH39039 |
| CD38 | D84284 | BAA18966 |
| β2-microglobulin | CR457066 | CAG33347 |
| CD52 | NM_001803 | NP_001794 |
| p53 | NM_000546 | NP_000537 |

TABLE 7

Amino Acid and Nucleotide Sequences for CD40 and CD40L.

| | Nucleotide Sequence | | Amino Acid Sequence | |
|---|---|---|---|---|
| Name | Accession No. | Sequence Identifier | Accession No. | Sequence Identifier |
| CD40 short isoform | NM_152854 | SEQ ID NO: 9 | NP_690593 | SEQ ID NO: 10 |
| CD40 long isoform | X60592 | SEQ ID NO: 11 | CAA43045 | SEQ ID NO: 12 |
| CD40L | NM_000074 | SEQ ID NO: 13 | NP_000065 | SEQ ID NO: 14 |
| Soluble CD40L | NM_000074 | SEQ ID NO: 15 (nucleotides 139-786 of SEQ ID NO: 13) | NP_000065 | SEQ ID NO: 16 (residues 47-261 of SEQ ID NO: 14) |

Example 6

Assays for Antagonist Activity of Anti-CD40 Therapeutic Agents

The following assays can be used to assess the antagonist activity of an anti-CD40 antibody. Human B cells for these assays can be obtained, for example, by isolation from tonsils obtained from individuals undergoing tonsillectomies, essentially as described in De Groot et al. (1990) *Lymphokine Research* (1990) 9:321. Briefly, the tissue is dispersed with scalpel blades, phagocytic and NK cells are depleted by treatment with 5 mM L-leucine methyl ester and T cells are removed by one cycle of rosetting with sheep erythrocytes (SRBC) treated with 2-aminoethyl isothiouronium bromide. The purity of the resulting B lymphocyte preparations can be checked by indirect immunofluorescent labelling with anti-(CD20) mAb B1 (Coulter Clone, Hialeah, FA) or anti-(CD3) mAb OKT3 (Ortho, Raritan, N.J.) and a FITC-conjugated F(ab')$_2$ fragment of rabbit anti-(mouse Ig) (Zymed, San Francisco, Calif.), and FACS analysis.

B-Cell Proliferation Assay.

B cells ($4\times10^4$ per well) are cultured in 200 μl IMDM supplemented with 10% fetal calf serum in flat bottom 96-well microtiter plates. B cells are stimulated by addition of immobilized anti-(IgM) antibodies (Immunobeads; 5 μg/ml; BioRad, Richmond, Calif.). Where desired, 100 U/ml recombinant IL-2 is added. Varying concentrations of test monoclonal antibodies (mAbs) are added at the onset of the microcultures and proliferation is assessed at day 3 by measurement of the incorporation of (3H)-thymidine after 18 hour pulsing.

An antagonist anti-CD40 antibody does not significantly costimulate human B-cell proliferation in the presence of immobilized anti-IgM or in the presence of immobilized anti-IgM and IL-2.

Banchereau-Like B-Cell Proliferation Assay.

For testing the ability of anti-CD40 monoclonal antibodies to stimulate B-cell proliferation in a culture system analogous to that described by Banchereau et al. (1991) *Science* (1991) 251:70, mouse 3T6 transfectant cells expressing the HR allellic form of human FcγRII are used. B cells ($2\times10^4$ per well) are cultured in flat-bottom microwells in the presence of $1\times10^4$ transfectant cells (irradiated with 5000 Rad) in 200 μl IMDM supplemented with 10% fetal calf serum and 100 U/ml recombinant IL-4. Before addition of the B cells, the 3T6 cells are allowed to adhere to the culture plastic for at least 5 hours. Anti-CD40 mAbs are added at concentrations varying from 15 ng/ml to 2000 ng/ml and proliferation of B cells is assessed by measurement of thymidine incorporation at day 7, upon 18 hour pulsing with [$^3$H] thymidine.

Inhibition of S2C6-Stimulated B-Cell Proliferation Using Antagonist Anti-CD40 mAbs.

Antagonist anti-CD40 monoclonal antibodies (mAbs) can also be characterized by their ability to inhibit stimulation of B-cell proliferation by an anti-CD40 antibody such as S2C6 (also known as SGN-14, which is reportedly an agonist of CD40 stimulation of proliferation of normal B cells; Francisco et al. (2000) *Cancer Res.* 60:3225-3231) using the B-cell Proliferation Assay described above. Human tonsillar B cells ($4\times10^4$ per well) are cultured in 200 μl in microwells in the presence of anti-IgM coupled to Sepharose beads (5 μg/ml) and anti-CD40 mAb S2C6 (1.25 μg/ml). Varying concentrations of an anti-CD40 mAb of interest are added and [$^3$H]-thymidine incorporation is assessed after 3 days. As a control anti-(glucocerebrosidase) mAb 8E4 can be added in similar concentrations. Barneveld et al. (1983) *Eur. J. Biochem.* 134:585. An antagonist anti-CD40 antibody can inhibit the costimulation of anti-IgM induced human B-cell proliferation by mAb S2C6, for example, by at least 75% or more (i.e., S2C6-stimulated proliferation in the presence of an antagonist anti-CD40 antibody is no more than 25% of that observed in the absence of the antagonist anti-CD40 antibody). In contrast, no significant inhibition would be seen with equivalent amounts of non-relevant mAb 8E4, directed to β-glucocerebrosidase. Barneveld et al., supra. Such a result would indicate that the anti-CD40 mAbs does not deliver stimulatory signals for the proliferation of human B cells, but, conversely, can inhibit stimulatory signals exerted by triggering CD40 with another mAb.

B-Cell Activation Assay with EL4B5 Cells.

Zubler et al. (1985) *J. Immunol.* (1985) 134:3662 observed that a mutant subclone of the mouse thymoma EL-4 line, known as EL4B5, could strongly stimulate B cells of both murine and human origin to proliferate and differentiate into immunoglobulin-secreting plasma cells in vitro. This activation was found to be antigen-independent and not MHC restricted. For optimal stimulation of human B cells, the presence of supernatant from activated human T cells was needed but a B-cell response also occurred when EL4B5 cells were preactivated with phorbol-12-myristate 13-acetate (PMA) or IL-1. Zubler et al. (1987) *Immunological Reviews* 99:281; and Zhang et al. (1990) *J. Immunol.* 144:2955. B-cell activation in this culture system is efficient—limiting dilution experiments have shown that the majority of human B cells can be activated to proliferate and differentiate into antibody-secreting cells. Wen et al. (1987) *Eur. J. Immunol* 17:887.

B cells (1000 per well) are cultured together with irradiated (5000 Rad) EL4B5 cells ($5 \times 10^4$ per well) in flat bottom microtiter plates in 200 μl IMDM supplemented with 10% heat-inactivated fetal calf serum, 5 ng/ml phorbol-12-myristate 13-acetate (Sigma) and 5% human T-cell supernatant. mAbs are added at varying concentrations at the onset of the cultures and thymidine incorporation is assessed at day 6 after 18 hour pulsing with [$^3$C]-thymidine. For the preparation of T-cell supernatant, purified T cells are cultured at a density of $10^6$/ml for 36 hours in the presence of 1 μg/ml PHA and 10 ng/ml PMA. Wen et al. (1987) *Eur. J. Immunol.* (1987) 17:887. T-cell supernatant is obtained by centrifugation of the cells and stored at −20° C. The effectiveness of T-cell supernatants in enhancing proliferation of human B cells in EL4B5-B cell cultures is tested and the most effective supernatants are pooled for use in experiments. When assessing the effect of an anti-CD40 antibody on EL4B5-induced human B-cell proliferation, a monoclonal antibody such as MOPC-141 (IgG2b) can be added as a control.

An antagonist anti-CD40 antibody can inhibit B-cell proliferation stimulated by the EL4B5 cell line, for example, by at least 75% or more (i.e., EL4B5-induced B cell proliferation in the presence of an antagonist anti-CD40 antibody is no more than 25% of that observed in the absence of the antagonist anti-CD40 antibody). In contrast, a control antibody such as MOPC-141 would have no significant effect on EL4B5-induced B cell proliferation.

Human T Cell Helper Assay for Antibody Production by B Cells.

An antagonist anti-CD40 antibody can function as an antagonist of immunoglobulin production by B cells. An anti-CD40 antibody can be tested for this type of antagonist activity by assessing the antibody's ability to inhibit immunoglobulin production by B cells that have been stimulated in a contact-dependent manner with activated T cells in a T cell helper assay. In this manner, 96-well tissue culture plates are coated with a 1:500 dilution of ascites fluid of anti-CD3 mAb CLB-T3/3 (CLB, Amsterdam, The Netherlands). As indicated costimulatory mAbs are added: anti CD2 mAbs CLB-T11.1/1 and CLB-T11.2/1 (CLB, Amsterdam, The Netherlands), both ascites 1:1000 and anti-CD28 mAb CLB-28/1 (CLB, Amsterdam, The Netherlands). Subsequently, tonsillar T cells (irradiated, 3000 Rad; $10^5$ per well), tonsillar B cells ($10^4$ per well), and rIL-2 (20 U/ml) are added. The final volume of each cell culture is 200 μl. After 8 days, cells are spun down, and cell-free supernatant is harvested. The concentrations of human IgM and IgG in (diluted) samples is estimated by ELISA as described below.

In one embodiment, human tonsillar B cells ($10^4$/well) are cultured together with irradiated purified T cells (3000 rad, 105/well) in 96-well plates, coated with anti-CD3 mAb and with or without different mAbs to costimulate the T cells. After 8 days of culture the supernatants are harvested for the determination of immunoglobulin production by the B cells. Immunoglobulin production by the B cells is assessed by the ELISA assay described below. The anti-CD40 antibody of interest is added in varying concentrations from the onset of the cultures. As a control, mAb MOPC-141 can be added.

An antagonist anti-CD40 antibody can inhibit IgG and IgM antibody production of B cells stimulated by human T cells by at least 50% or more (i.e., T cell-induced antibody production by B cells in the presence of an antagonist anti-CD40 antibody is no more than 50% of that observed in the absence of the antagonist anti-CD40 antibody). In contrast, a control antibody such as MOPC-141 would have no significant effect on T cell-induced antibody production by B cells.

ELISA Assay for Immunoglobulin Quantification.

The concentrations of human IgM and IgG are estimated by ELISA. 96-well ELISA plates are coated with 4 μg/ml mouse anti-human IgG mAb MH 16-01 (CLB, Amsterdam, The Netherlands) or with 1.2 μg/ml mouse anti-human IgM mAb 4102 (Tago, Burlingame, Calif.) in 0.05 M carbonate buffer (pH=9.6), by incubation for 16 h at 4° C. Plates are washed 3 times with PBS-0.05% Tween-20 (PBS-Tween) and saturated with BSA for 1 hour. After 2 washes the plates are incubated for 1 h at 37° C. with different dilutions of the test samples. After 3 washes, bound Ig is detected by incubation for 1 h at 37° C. with 1 μg/ml peroxidase-labeled mouse anti-human IgG mAb MH 16-01 (CLB) or mouse anti-human IgM mAb MH 15-01 (CLB). Plates are washed 4 times and bound peroxidase activity is revealed by the addition of O-phenylenediamine as a substrate. Human standard serum (H00, CLB) is used to establish a standard curve for each assay.

Example 7

Comparisons of Effects of CHIR-12.12 on CD40 Ligand-Mediated CD40 Signaling in Normal B Cells and B-Chronic Lymphocytic Leukemia Cells The activation of CD40 by CD40 ligand (CD40L) can regulate the survival, proliferation, and differentiation of normal B lymphocytes. In B cells, ligation of CD40 leads to its binding with tumor necrosis factor receptor-associated factors (TRAFs) and the subsequent activation of multiple downstream signaling pathways involved in cellular proliferation and survival. The activation of this pathway can be demonstrated ex vivo, where addition of CD40L to cultured normal B cells promotes their survival and proliferation.

Similar to its activity in normal B cells in culture, CD40L promotes the survival and proliferation of B-chronic lymphocytic leukemia (CLL) cells obtained from patient samples, and this pathway is sensitive to pharmacological intervention.

The additional studies described below were undertaken to further characterize the effects of the CHIR-12.12 monoclonal antibody on CD40L-mediated CD40 survival and signaling pathways in normal human B cells and human B-CLL cells. These studies confirmed the observations outlined above. Thus, CHIR-12.12 treatment blocked CD40L binding to CD40 and inhibited CD40L-induced proliferation/survival of normal human B cells and primary B-CLL cells. CD40L-mediated survival was associated with a reduction in the levels of the apoptotic marker cPARP and induction of anti-apoptotic proteins Mcl-1 and Bcl-xl. Additionally, CD40L-induced survival was associated with the phosphorylation of Akt, p38 MAPK, ERK, and IκB kinases (IKK) α and β. In contrast, CHIR-12.12 treatment of CD40L-stimulated primary B-CLL cells ex vivo inhibited the expression of these anti-apoptotic proteins and the phosphorylation of the downstream signaling proteins, ultimately leading to B-CLL cell apoptosis. The majority of CLL samples analyzed in this study appeared to be responsive to CD40L stimulation and antibody inhibition. The few CLL samples that were insensitive are under investigation to identify the pathways in these samples that may account for their insensitivity.

CHIR-12.12 Treatment Blocks CD40 Ligand-Mediated CD40 Survival and Signaling Pathways in Normal Human B Cells.

Figure 23:
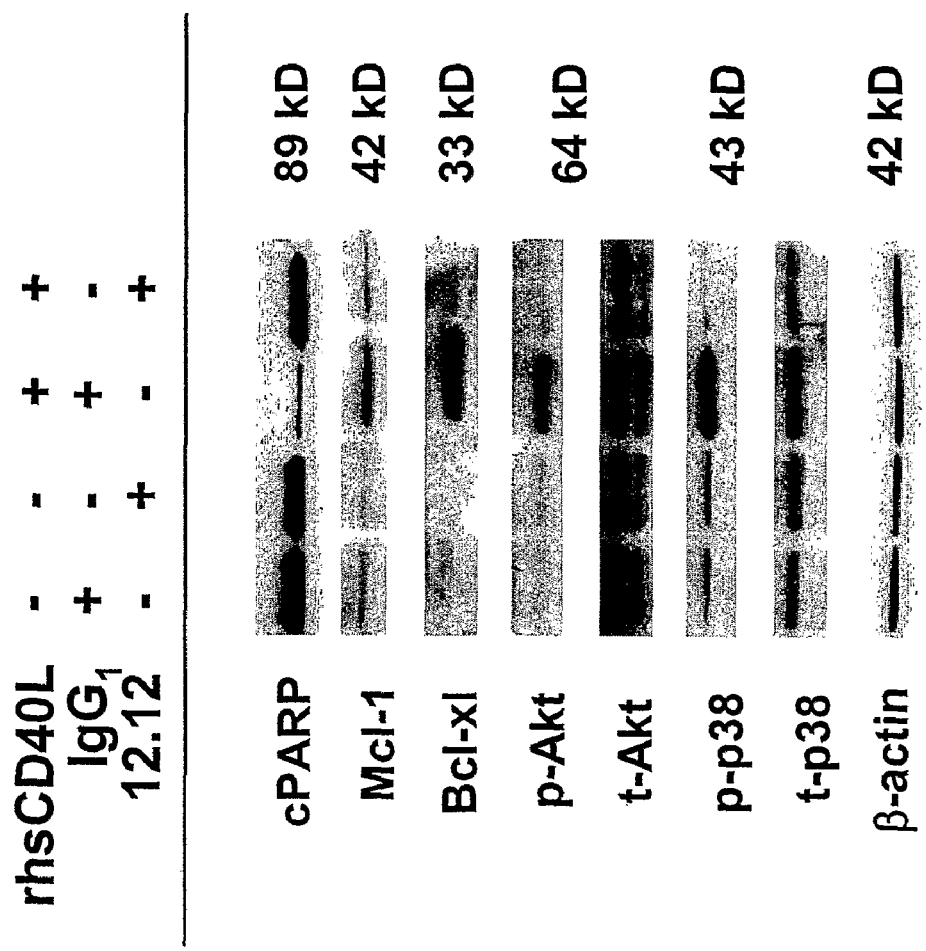
FIG. 23 shows that signaling and survival of normal human B Cells are induced by CD40L and blocked by CHIR-12.12.

Normal human B cells were purified from peripheral blood by negative selection using the MACS B cell isolation kit II (Miltenyi Biotech INC, Auburn, Calif.) and cultured for 24 hr with or without 2 μg/ml of recombinant human soluble CD40L (rhsCD40L) in the presence of 10 μg/ml of CHIR-12.12 or isotype control hIgG1. Cells were lysed and whole cell lysates resolved by SDS-PAGE and Western blotting using antibodies specific to human cPARP, Mcl-1, Bcl-xl, p-Akt, and p-p38 MAPK. All membranes were stripped and re-probed for either β-actin or AKT or p38 MAPK total protein, as appropriate. Results are shown in FIG. 23.

CD40L stimulation of normal B cells decreased levels of the apoptotic marker (cPARP), increased expression of anti-apoptotic markers (Mcl-1, Bcl-xl), and activated phosphorylation of signaling markers (p-Akt, p-p38). CHIR-12.12 treatment blocked these CD40L-mediated effects on normal B cells, leading to apoptosis of these cells.

Effects of CHIR-12.12 Treatment on CD40 Ligand-Mediated Survival and Signaling Pathways in B-CLL Cells.

In order to further assess the effects of CHIR-12.12 on survival and signaling pathways in B-CLL cells, PBMCs were isolated from peripheral blood of CLL patients using Vacutainer® CPT™ Cell Preparation Tubes with sodium citrate (BD Biosciences, San Jose, Calif.), stained for CD5, CD19, and CD40 (mouse anti-human CD5-PerCP Cy5.5 (BD Biosciences, San Jose, Calif.), mouse anti-human CD19-PE (Ancell, Bayport, Minn.), and FITC-labeled mouse anti-human CD40 antibody (FITC-CHIR-12.12, Chiron Corporation, Emeryville, Calif.)), fixed, and analyzed by flow cytometry. Patient and PBMC expression characteristics are summarized in Table 8.

TABLE 8

Patient and PBMC Characteristics of CLL Samples.

| Patient ID | Age | Gender | % Total PBMC CD5+ CD19+ | % Total PBMC CD40+ |
|---|---|---|---|---|
| M1 | 70 | M | n/a | 74 |
| M2 | 74 | M | 97 | 97 |
| M3 | 59 | F | 92 | 93 |
| M4 | 64 | F | 91 | 96 |
| M5 | 68 | M | 97 | 98 |
| M6 | 67 | F | 92 | 92 |
| M7 | 40 | F | 85 | 81 |

CHIR-12.12 treatment blocks CD40 ligand-mediated survival pathway in B-CLL cells. PBMCs (50,000/well in duplicate wells) were seeded in 96-well tissue culture plates (Corning Costar, Corning, N.Y.) in RPMI+10% FCS and pen/strep alone or in the presence of 2 μg/ml rhsCD40L+4 μg/ml CD40L enhancer with either 10 μg/ml CHIR-12.12 or control human IgG1. Cell viability was determined after 72 hours using the CellTiter-Glo® Luminescent Cell Viability Kit (Promega, Madison, Wis.), which measures cellular ATP, and expressed as Relative Luminescence Units (RLU). Percent blockade was calculated as follows:

$$\% \text{ blockade} = \left\{ 1 - \frac{[(12.12 + L) - (\text{cells alone})]}{[(IgG1 + L) - (\text{cells alone})]} \right\} \times 100.$$

cPARP analysis by flow cytometry was performed after 24 hours in culture. Cells were treated with FACSLysis buffer (BD Biosciences) and frozen. After fixation in 1% formaldehyde for 45 min, cells were washed and incubated with PE-conjugated mouse anti-human CD19 for 30 min at room temperature (RT). Cells were then permeabilized using 70% ethanol on ice for 30 min and stained for 30 min at RT with rabbit anti-human cPARP antibody or isotype control rabbit IgG along with PerCP-Cy5.5-labeled mouse anti-human CD5. This was followed by incubation with goat anti-rabbit IgG-AlexaFluor 647 for 30 min at RT before fixing with 1% formaldehyde and analyzing by flow cytometry. Percent blockade was calculated as follows:

$$\% \text{ blockade} = \left\{ 1 - \frac{[(\text{cells alone}) - (12.12 + L)]}{[(\text{cells alone}) - (IgG1 + L)]} \right\} \times 100.$$

Figure 24:
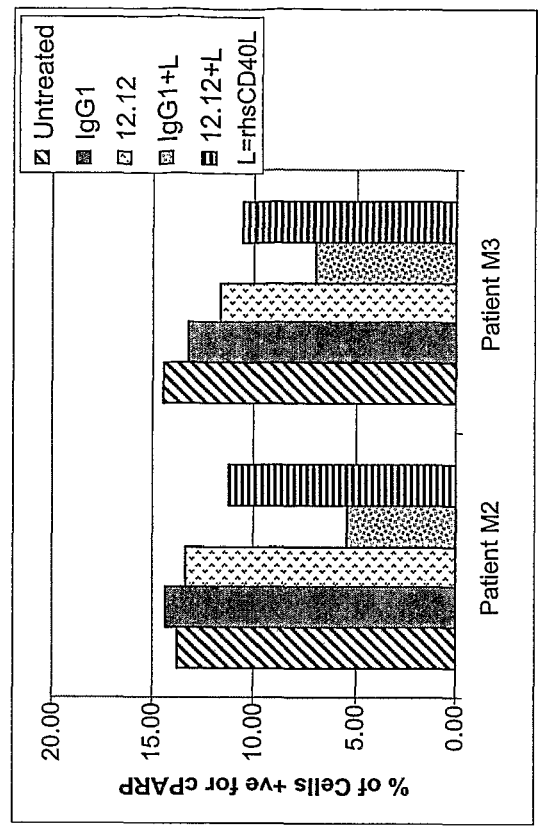
FIG. 24 shows that CD40L rescues B-CLL cells from apoptosis and CHIR-12.12 blocks this effect as determined by CellTiter-Glo viability (A) and cPARP flow cytometry (B) assays.
Figure 24:
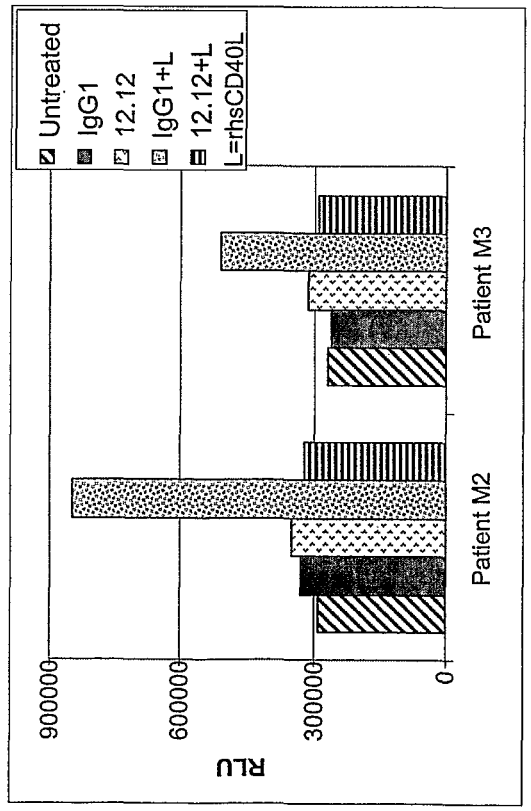

Stimulation with CD40L could promote survival/prevent apoptosis in cultured B-CLL cells, and these effects could be blocked by CHIR-12.12 (FIG. 24). In 7/7 samples in the CellTiter-Glo® assay and 6/7 samples in the cPARP flow cytometry assay, CD40L promoted survival of B-CLL cells and in each case, these effects were blocked by CHIR-12.12 (Table 9).

Table 9. Effects of CHIR-12.12 treatment on CD40L-mediated B-CLL cell survival as measured by CellTiter-Glo® assay and cPARP flow cytometry.

| | CellTiter-Glo® Assay | | | cPARP Flow Cytometry | | |
|---|---|---|---|---|---|---|
| Subject ID | Non-treated Control (RLU x 10³) | Fold Induction by rhsCD40L | % Block of rhsCD40L by CHIR-12.12 | % cPARP+ Cells in Non-treated Control | Fold Inhibition by rhsCD40L | % Block of rhsCD40L by CHIR-12.12 |
| Normal B | 100 | 3.0 | 99 | 19 | 3 | 83 |
| M1 | 200 | 3.1 | 94 | 14 | 5.8 | 77 |
| M2 | 290 | 2.9 | 95 | 14 | 2.6 | 70 |
| M3 | 270 | 1.9 | 92 | 14 | 2.1 | 48 |
| M4 | 240 | 2.3 | 87 | 22 | 3.2 | 71 |
| M5 | 110 | 3.5 | 71 | 5 | 2.3 | 48 |
| M6 | 230 | 2.6 | 72 | 7 | 0.9 | 109 |
| M7 | 75 | 3.8 | 96 | 50 | 5.2 | 80 |

Figure 25:
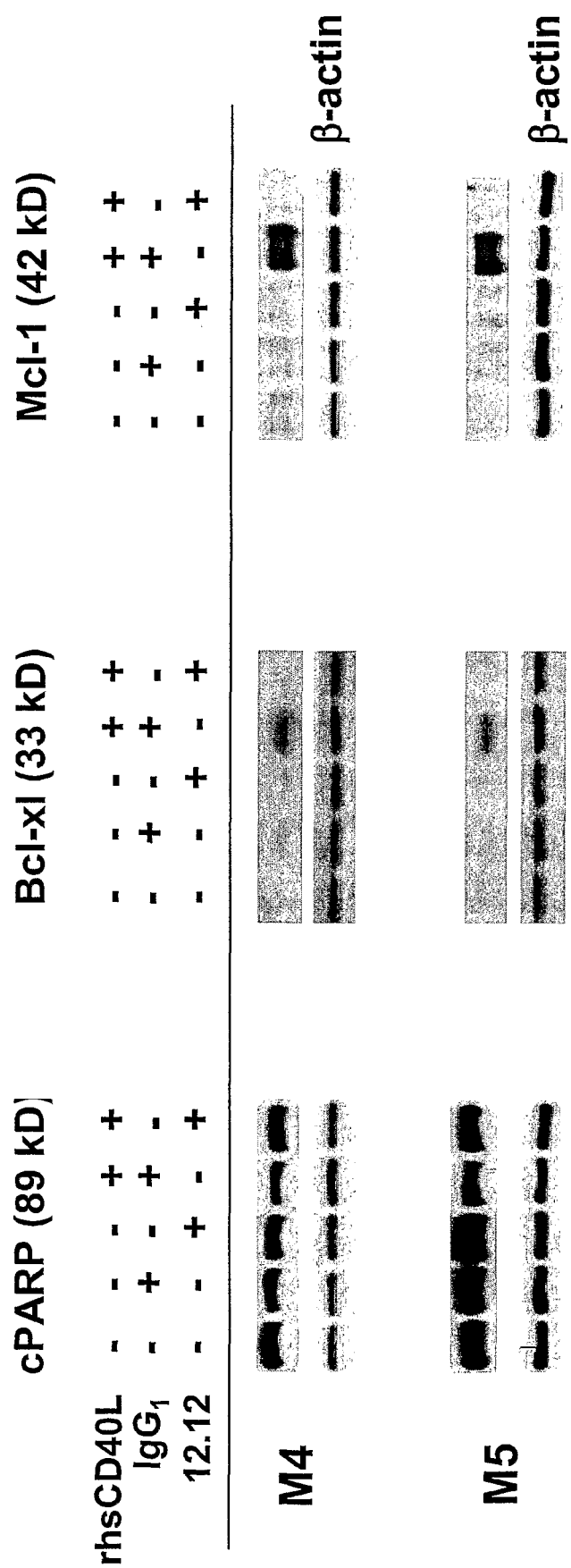
FIG. 25 shows that CHIR-12.12 blocks the CD40L-mediated decrease of cPARP and increase of Bcl-xl and Mcl-1 expression in B-CLL cells.

Effects of CHIR-12.12 treatment on expression of anti-apoptotic proteins. Following PBMC isolation, 2×10⁶ cells/ml were cultured as described above for data shown in FIG. 24. Whole cell lysates were prepared in RIPA lysis buffer (1% Nonidet P-40, 0.5% sodium deoxycholate, 0.1% Sodium dodecylsulfate in 1× phosphate buffered saline, pH 7.2). 10-20 μg of protein per sample were resolved on a 10% Tris-Glycine gel and transferred to nitrocellulose membranes, and membranes were probed using mAbs specific to human cPARP, Mcl-1, or Bcl-xl. The membranes were stripped and re-probed for β-actin and developed using ECL. Results are shown in FIG. 25. CHIR-12.12 treatment blocked the CD40L-mediated decrease of cPARP levels and CD40L-mediated increase of Mcl-1 and Bcl-xl expression in primary B-CLL cells.

Figure 26:
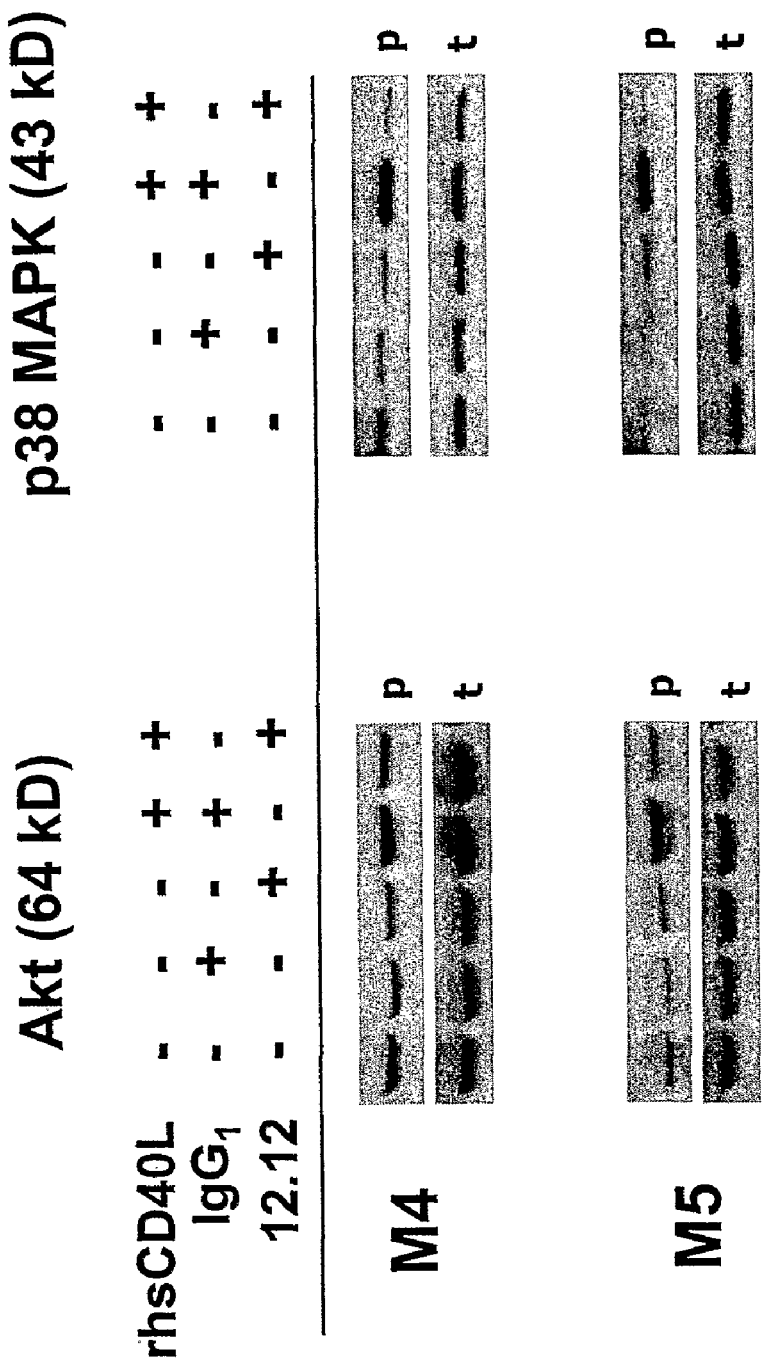
FIG. 26 shows that CHIR-12.12 inhibits the CD40L-induced phosphorylation of Akt and p38 MAPK in B-CLL cells.

Effects of CHIR-12.12 treatment on CD40 ligand-mediated signaling pathways in B-CLL cells. The effects of CHIR-12.12 on CD40 ligand-mediated signaling in the AKT and p38 MAPK signaling pathways were assessed for B-CLL cells. To evaluate phosphorylated Akt (p-Akt), PBMC were cultured as described above for data shown in FIG. 24. To detect p38 MAPK, cells were cultured for 3 hr using the previously described conditions, with rhsCD40L being added in the last 20 min of incubation. Cells were processed as described above for data shown in FIG. 25. mAbs specific to human p-Akt and p-p38 MAPK were used to probe the resultant membranes, which were re-probed for AKT and p38 total protein, respectively. Results are shown in FIG. 26. While in some samples CD40L did not appear to stimulate phosphorylation of AKT, in a number of samples, CD40L activated the AKT pathway and CHIR-12.12 blocked this effect. While the levels of p38 MAPK phosphorylation in untreated cells varied, treatment with rhsCD40L enhanced the phosphorylation of p38 MAPK and CHIR-12.12 blocked this effect.

Figure 27:
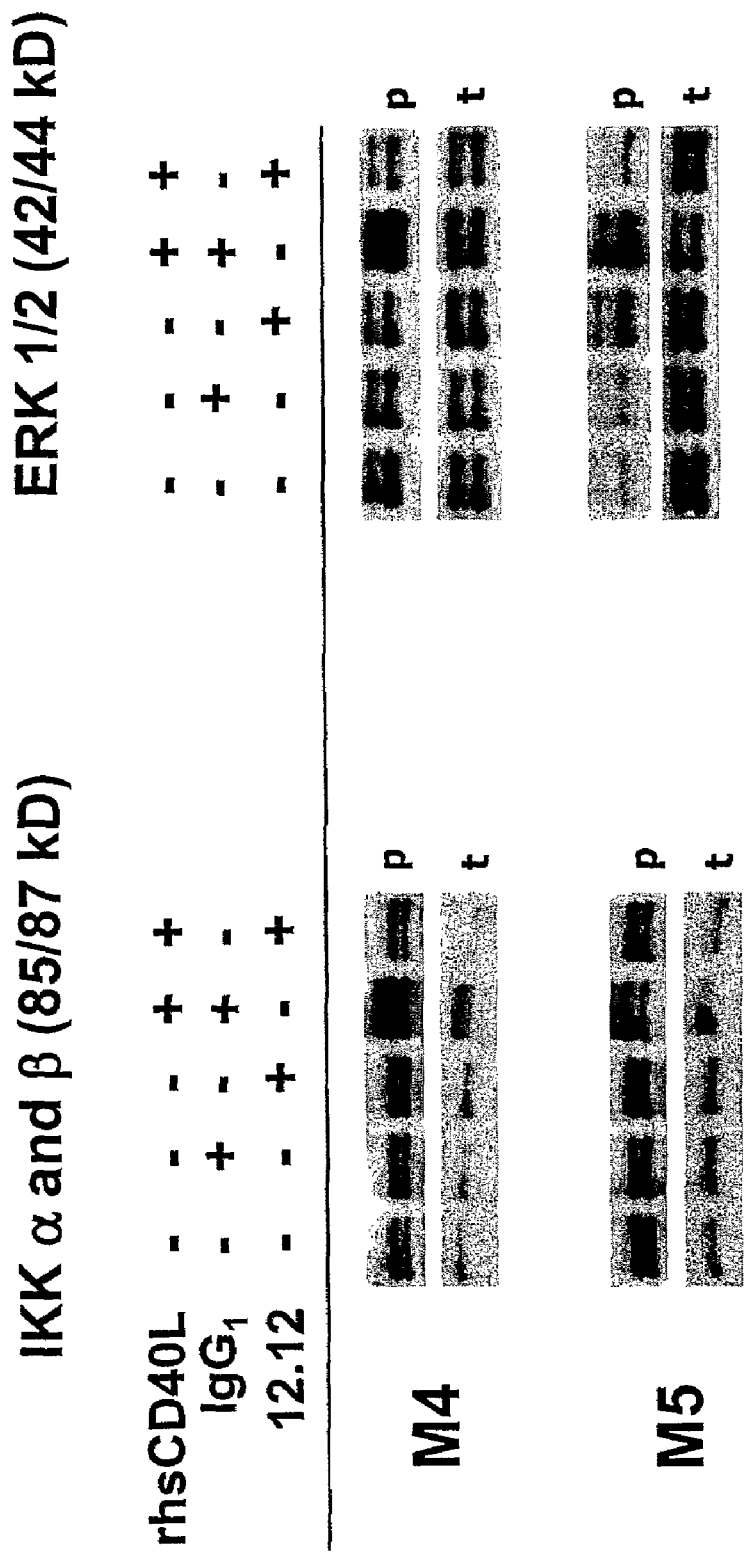
FIG. 27 shows that CHIR-12.12 inhibits the CD40L-induced phosphorylation of IKK α/β and ERK ½ in B-CLL cells.

To evaluate the effects of rhsCD40L and CHIR-12.12 on IKK α/β and ERK ½, PBMCs were cultured and processed as described for detection of p38 in FIG. 26. Resultant membranes were probed using mAbs specific to human p-IKK α/β and p-ERK. Results are shown in FIG. 27. CHIR-12.12 treatment inhibited the CD40L-induced phosphorylation of IKK α/β and ERK ½ in B-CLL cells.

Summary

When placed in culture, normal B lymphocytes undergo spontaneous apoptosis, and this can be reversed by addition of CD40L to the cultures. In the studies described herein, addition of CD40L to normal B lymphocytes resulted in upregulation of survival proteins such as Mcl-1 and Bcl-xl and activated the AKT and p38 pathways. B-CLL cells obtained from chronic lymphocytic leukemia patient samples were similarly responsive to CD40L in the described assays. In addition CD40L stimulated phosphorylation of IKK α and β and ERK ½ in B-CLL cells. These pathways were evaluated in B-CLL cells as they have been shown to be important in B cell survival and may contribute to the disregulated survival of B-CLL cells. In both normal B cells and the B-CLL cell samples responsive to CD40L stimulation, each of the described effects could be blocked by the antagonistic anti-CD40 antibody, CHIR-12.12.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

That which is claimed:

1. A method for identifying a subject having a cancer that is responsive to treatment with an anti-CD40 therapeutic agent, said method comprising:
  a) providing a test biological sample obtained from said subject and a control biological sample obtained from said subject, wherein said test biological sample and said control biological sample comprise CD40-expressing neoplastic cells that have been stimulated with a CD40 ligand;
  b) contacting said test biological sample with an effective amount of said anti-CD40 therapeutic agent;
  c) detecting the level of at least one biomarker in said test biological sample, wherein said biomarker is selected from the group consisting of:
    (i) a biomarker of cellular apoptosis, wherein said biomarker of apoptosis is selected from the group consisting of a cleaved Caspase protein, cleaved poly ADP-ribose polymerase (PARP), cell surface expression of phosphotidylserine (PS), genomic DNA fragmentation, and any combinations thereof;
    (ii) a biomarker of a CD40L-mediated CD40 signaling pathway, wherein said biomarker of said CD40L-mediated CD40 signaling pathway is selected from the group consisting of phospho-PI3K, phospho-PDK1, phospho-AKT, phospho-MEK, phospho-ERK, phospho-p38, phospho-IKKα/β, phospho-IκB protein, and activated NF-κB;
    (iii) and a biomarker of cell survival, wherein said biomarker of cell survival is selected from the group consisting of an anti-apoptotic protein that is a Bcl-2 family member, an IAP apoptosis inhibitor protein, and TNF receptor-associated factor-1 (TRAF-1); and
d) comparing the level of said at least one biomarker in said test biological sample to the level of said at least one biomarker detected in said control biological sample, wherein said control biological sample has not been contacted with said anti-CD40 therapeutic agent, wherein
   (i) at least a 20% increase in the level of at least one of said biomarkers of apoptosis, and/or
   (ii) at least a 25% reduction in the level of at least one of said biomarkers of at least one of said CD40L-mediated CD40 signaling pathways, and/or
   (iii) at least a 25% reduction in the level of at least one of said biomarkers of cell survival
in said test biological sample relative to said control biological sample is indicative of a subject who would benefit from treatment with said anti-CD40 therapeutic agent;
wherein said anti-CD40 therapeutic agent is an antagonist anti-CD40 monoclonal antibody that is capable of specifically binding to a human CD40 antigen expressed on the surface of a human B cell, said monoclonal antibody being free of significant agonist activity when bound to the CD40 antigen expressed on the surface of said B cell, wherein said anti-CD40 monoclonal antibody is selected from the group consisting of:
a) a monoclonal antibody comprising a light chain variable domain containing the complementarity determining region (CDR) residues of SEQ ID NO:2 and a heavy chain variable domain containing the CDR residues of SEQ ID NO:4;
b) a monoclonal antibody comprising a light chain variable domain containing the CDR residues of SEQ ID NO:2 and a heavy chain variable domain containing the CDR residues of SEQ ID NO:5;
c) a monoclonal antibody comprising a light chain variable domain containing the CDR residues of SEQ ID NO:6 and a heavy chain variable domain containing the CDR residues of SEQ ID NO:7;
d) a monoclonal antibody comprising a light chain variable domain containing the CDR residues of SEQ ID NO:6 and a heavy chain variable domain containing the CDR residues of SEQ ID NO:8; and
e) a monoclonal antibody that is an antigen-binding fragment of a monoclonal antibody of any one of preceding items a)-j), wherein said fragment retains the capability of specifically binding to said human CD40 antigen.

2. The method of claim 1, wherein said CD40-expressing neoplastic cells were stimulated ex vivo with a ligand of CD40 prior to said contacting step.

3. The method of claim 2, wherein said ligand of CD40 is selected from the group consisting of soluble CD40L and membrane-bound CD40L.

4. The method of claim 1, wherein said fragment is selected from the group consisting of a Fab fragment, an F(ab')$_2$ fragment, an Fv fragment, and a single-chain Fv fragment.

5. The method of claim 1, wherein said cleaved Caspase protein is selected from the group consisting of cleaved Caspase-3, cleaved Caspase-7, and cleaved Caspase-9.

6. The method of claim 1, wherein cell surface PS is detected by annexin V staining and wherein genomic DNA fragmentation is detected by TUNEL staining.

7. The method of claim 1, wherein said Bcl-2 family member is selected from the group consisting of Bcl-xl and Mcl-1.

8. The method of claim 1, wherein said IAP apoptosis inhibitor protein is selected from the group consisting of survivin, XIAP, and cIAP1.

9. The method of claim 1, further comprising detecting in said test biological sample and said control biological sample the level of at least one cytokine marker of CD40 signaling.

10. The method of claim 9, wherein said cytokine marker is selected from the group consisting of vascular endothelial growth factor (VEGF), interleukin (IL)-6, IL-8, IL-10, granulocyte monocyte colony-stimulating factor (GM-CSF), tumor necrosis factor-α (TNF-α), monocyte chemoattractant protein-1 (MCP-1), and macrophage inflammatory protein-1β (MIP-1β).

11. The method of claim 9, wherein a reduction in the level of at least one of said cytokine markers in said test biological sample relative to said control biological sample is indicative of a subject who would benefit from treatment with said anti-CD40 therapeutic agent.

12. The method of claim 1, wherein said anti-CD40 therapeutic agent is an anti-CD40 monoclonal antibody that specifically binds to a human CD40 antigen expressed on the surface of a CD40-expressing cell, thereby modulating antibody-dependent cell-mediated cytotoxity (ADCC) activity, and wherein said biomarker is said biomarker of apoptosis.

13. The method of claim 12, wherein said cleaved caspase protein is selected from the group consisting of cleaved Caspase-3, cleaved Caspase-7, and cleaved Caspase-9.

14. The method of claim 12, wherein cell surface PS is detected by annexin V staining and wherein genomic DNA fragmentation is detected by TUNEL staining.

15. The method of claim 1, wherein said cancer is selected from the group consisting of non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lympohoblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, Waldenstrom's Macroglobulinemia, mantle cell lymphoma, and heavy chain disease.

16. The method of claim 15, wherein said subject has chronic lymphocytic leukemia.

17. The method of claim 16, further comprising assaying a biological sample from said subject for at least one clinically useful prognostic marker selected from the group consisting of ZAP-70 expression level, CD38 expression level, β2 microglobulin expression level, p53 mutational status, ATM mutational status, chromosome 17p deletion, and chromosome 11q deletion.

18. The method of claim 1, wherein said cancer is a non-B cell hematological malignancy.

19. The method of claim 18, wherein said malignancy is selected from the group consisting of acute leukemias, myeloblastic leukemias, acute myelocytic leukemias, promyelocytic leukemia, myelomonocytic leukemia, monocytic leukemia, erythroleukemia, chronic myelocytic leukemia, and polycythemia vera.

20. The method of claim 1, wherein said cancer is a solid tumor comprising neoplastic cells expressing CD40 antigen.

21. The method of claim 20, wherein said solid tumor is selected from the group consisting of lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, and sarcomas.

22. The method of claim 1, further comprising detecting in a biological sample of said subject the level of expression of cell-surface CD40, the level of expression of cell-surface CD40L, or both, on CD40-expressing neoplastic cells within said biological sample.

23. The method of claim 1, further comprising detecting the level of circulating soluble CD40 or circulating soluble CD40L in a biological sample collected from subject.

24. The method of claim 1, wherein detecting the level of said biomarker comprises using an antibody to detect biomarker protein expression.

25. The method of claim 1, wherein detecting the level of said biomarker comprises nucleic acid hybridization.

26. The method of claim 1, wherein detecting the level of said biomarker comprises performing quantitative RT-PCR.

27. A method of treating a subject with a cancer or pre-malignant condition that is associated with CD40-expressing cells, said method comprising screening said patient with a method according to claim 1, and then treating said subject with said anti-CD40 therapeutic agent when said method according to claim 1 generates a result that is indicative of a positive treatment outcome with said anti-CD40 therapeutic agent.

28. A method for monitoring efficacy of an anti-CD40 therapeutic agent in treatment of a subject for a cancer that is associated with CD40-expressing neoplastic cells, said method comprising:
 a) obtaining a baseline biological sample from said subject prior to administering a dose of said anti-CD40 therapeutic agent, wherein said baseline biological sample comprises CD40-expressing neoplastic cells;
 b) detecting the level of at least one biomarker in said baseline biological sample, wherein said biomarker is selected from the group consisting of:
  (i) a biomarker of cellular apoptosis, wherein said biomarker of apoptosis is selected from the group consisting of a cleaved Caspase protein, cleaved poly ADP-ribose polymerase (PARP), cell surface expression of phosphotidylserine (PS), genomic DNA fragmentation, and any combinations thereof;
  (ii) a biomarker of a CD40L-mediated CD40 signaling pathway, wherein said biomarker of said CD40L-mediated CD40 signaling pathway is selected from the group consisting of phospho-PI3K, phospho-PDK1, phospho-AKT, phospho-MEK, phospho-ERK, phospho-p38, phospho-IKKα/β, phospho-IκB protein, and activated NF-κB;
  (iii) and a biomarker of cell survival, wherein said biomarker of cell survival is selected from the group consisting of an anti-apoptotic protein that is a Bcl-2 family member, an IAP apoptosis inhibitor protein, and TNF receptor-associated factor-1 (TRAF-1);
 c) administering said anti-CD40 therapeutic agent to said subject;
 d) obtaining from said subject at least one subsequent biological sample;
 e) detecting the level of said at least one biomarker in said at least one subsequent sample; and
 comparing the level of said at least one biomarker in said at least one subsequent sample with the level of said at least one biomarker in said baseline biological sample, wherein
  (i) at least a 20% increase in the level of at least one of said biomarkers of apoptosis, and/or
  (ii) at least a 25% reduction in the level of at least one of said biomarkers of at least one of said CD40L-mediated CD40 signaling pathways, and/or
  (iii) at least a 25% reduction in the level of at least one of said biomarkers of cell survival
 within said subsequent biological sample relative to said baseline biological sample is indicative of efficacy of treatment with said anti-CD40 therapeutic agent;
 wherein said anti-CD40 therapeutic agent is an antagonist anti-CD40 monoclonal antibody that is capable of specifically binding to a human CD40 antigen expressed on the surface of a human B cell, said monoclonal antibody being free of significant agonist activity when bound to the CD40 antigen expressed on the surface of said B cell, wherein said anti-CD40 monoclonal antibody is selected from the group consisting of:
  a) a monoclonal antibody comprising a light chain variable domain containing the complementarity determining region (CDR) residues of SEQ ID NO:2 and a heavy chain variable domain containing the CDR residues of SEQ ID NO:4;
  b) a monoclonal antibody comprising a light chain variable domain containing the CDR residues of SEQ ID NO:2 and a heavy chain variable domain containing the CDR residues of SEQ ID NO:5;
  c) a monoclonal antibody comprising a light chain variable domain containing the CDR residues of SEQ ID NO:6 and a heavy chain variable domain containing the CDR residues of SEQ ID NO:7;
  d) a monoclonal antibody comprising a light chain variable domain containing the CDR residues of SEQ ID NO:6 and a heavy chain variable domain containing the CDR residues of SEQ ID NO:8; and
  e) a monoclonal antibody that is an antigen-binding fragment of a monoclonal antibody of any one of preceding items a)-j), wherein said fragment retains the capability of specifically binding to said human CD40 antigen.

29. The method of claim 28, wherein a single dose of said anti-CD40 therapeutic agent is administered to said subject.

30. The method of claim 28, wherein multiple doses of said anti-CD40 therapeutic agent are administered to said subject.

31. The method of claim 28, wherein said fragment is selected from the group consisting of a Fab fragment, an F(ab')$_2$ fragment, an Fv fragment, and a single-chain Fv fragment.

32. The method of claim 28, wherein said cleaved Caspase protein is selected from the group consisting of cleaved Caspase-3, cleaved Caspase-7, and cleaved Caspase-9.

33. The method of claim 28, wherein cell surface PS is detected by annexin V staining and wherein genomic DNA fragmentation is detected by TUNEL staining.

34. The method of claim 28, wherein said Bcl-2 family member is selected from the group consisting of Bcl-xl and Mcl-1.

35. The method of claim 28, wherein said IAP apoptosis inhibitor protein is selected from the group consisting of survivin, XIAP, and cIAP1.

36. The method of claim 28, further comprising detecting in said subsequent biological sample and said baseline biological sample the level of at least one cytokine marker of CD40 signaling.

37. The method of claim 36, wherein said cytokine marker is selected from the group consisting of vascular endothelial growth factor (VEGF), interleukin (IL)-6, IL-8, IL-10, granulocyte monocyte colony-stimulating factor (GM-CSF), tumor necrosis factor-α (TNF-α), monocyte chemoattractant protein-1 (MCP-1), and macrophage inflammatory protein-1β (MIP-1β).

38. The method of claim 36, wherein a reduction in the level of at least one of said cytokine markers in said subsequent biological sample relative to said baseline biological sample is indicative of efficacy of treatment with said anti-CD40 therapeutic agent.

39. The method of claim 28, wherein said anti-CD40 therapeutic agent is an anti-CD40 monoclonal antibody that specifically binds to a human CD40 antigen expressed on the surface of a CD40-expressing cell, thereby modulating antibody-dependent cell-mediated cytotoxicity (ADCC), and wherein said biomarker is said biomarker of apoptosis.

40. The method of claim 39, wherein said biomarker of apoptosis is selected from the group consisting of a cleaved caspase protein, cleaved poly ADP-ribose polymerase (PARP), cell surface expression of phosphotidylserine (PS), genomic DNA fragmentation, and any combinations thereof.

41. The method of claim 40, wherein said cleaved caspase protein is selected from the group consisting of cleaved Caspase-3, cleaved Caspase-7, and cleaved Caspase-9.

42. The method of claim 40, wherein cell surface PS is detected by annexin V staining and wherein genomic DNA fragmentation is detected by TUNEL staining.

43. The method of claim 28, wherein said cancer is characterized by neoplastic B cell growth.

44. The method of claim 43, wherein said cancer is selected from the group consisting of non-Hodgkin's lymphoma, chronic lymphocytic leukemia, multiple myeloma, B cell lymphoma, high-grade B cell lymphoma, intermediate-grade B cell lymphoma, low-grade B cell lymphoma, B cell acute lymphoblastic leukemia, Hodgkin's disease, plasmacytoma, follicular lymphoma, follicular small cleaved lymphoma, follicular large cell lymphoma, follicular mixed small cleaved lymphoma, diffuse small cleaved cell lymphoma, diffuse small lymphocytic lymphoma, prolymphocytic leukemia, lymphoplasmacytic lymphoma, marginal zone lymphoma, mucosal associated lymphoid tissue lymphoma, monocytoid B cell lymphoma, splenic lymphoma, hairy cell leukemia, diffuse large cell lymphoma, mediastinal large B cell lymphoma, lymphomatoid granulomatosis, intravascular lymphomatosis, diffuse mixed cell lymphoma, diffuse large cell lymphoma, immunoblastic lymphoma, Burkitt's lymphoma, AIDS-related lymphoma, Waldenstrom's Macroglobulinemia, mantle cell lymphoma, and heavy chain disease.

45. The method of claim 28, wherein said cancer is a non-B cell hematological malignancy.

46. The method of claim 45, wherein said malignancy is selected from the group consisting of acute leukemias, myeloblastic leukemias, acute myelocytic leukemias, promyelocytic leukemia, myelomonocytic leukemia, monocytic leukemia, erythroleukemia, chronic myelocytic leukemia, and polycythemia vera.

47. The method of claim 28, wherein said cancer is a solid tumor comprising neoplastic cells expressing CD40 antigen.

48. The method of claim 47, wherein said solid tumor is selected from the group consisting of lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, and sarcomas.

49. The method of claim 28, further comprising detecting in said subsequent biological sample and said baseline biological sample the level of expression of at least one CD40-related factor selected from the group consisting of cell-surface CD40, cell-surface CD40L, and both cell-surface CD40 and cell-surface CD40L on CD40-expressing neoplastic cells within said subsequent and baseline biological samples, wherein a reduction in the level of expression of at least one of said CD40-related factors within said subsequent biological sample relative to said baseline biological sample is indicative of efficacy of treatment with said anti-CD40 therapeutic agent.

50. The method of claim 28, further comprising collecting from said subject a baseline sample of blood or a blood component and a subsequent sample of blood or said blood component, and detecting the level of circulating soluble CD40 or circulating soluble CD40L in said baseline sample and said subsequent sample, wherein a reduction in the level of expression of at least one of said circulating soluble CD40 or circulating soluble CD40L within said subsequent sample relative to said baseline sample is indicative of efficacy of treatment with said anti-CD40 therapeutic agent.

51. The method of claim 1, wherein said antagonist anti-CD40 monoclonal antibody is a monoclonal antibody comprising an amino acid sequence selected from the group consisting of:
  (i) SEQ ID NO:2;
  (ii) SEQ ID NO:4;
  (iii) SEQ ID NO:5;
  (iv) SEQ ID NO:2 and SEQ ID NO:4; and
  (v) SEQ ID NO:2 and SEQ ID NO:5
  (vi) SEQ ID NO:6;
  (vii) SEQ ID NO:7;
  (viii) SEQ ID NO:8;
  (ix) SEQ ID NO:6 and SEQ ID NO:7; and
  (x) SEQ ID NO:6 and SEQ ID NO:8.

52. The method of claim 1, wherein said antagonist anti-CD40 antibody is selected from the group consisting of:
  (i) a monoclonal antibody comprising the variable and constant region sequences shown in SEQ ID NO:2;
  (ii) a monoclonal antibody comprising the variable and constant region sequences shown in SEQ ID NO:4;
  (iii) a monoclonal antibody comprising the variable and constant region sequences shown in SEQ ID NO:5;
  (iv) a monoclonal antibody comprising the variable and constant region sequences shown in SEQ ID NO:2 and the variable and constant region sequences shown SEQ ID NO:4;
  (v) a monoclonal antibody comprising the variable and constant region sequences shown in SEQ ID NO:2 and the variable and constant region sequences shown SEQ ID NO:5;
  (vi) a monoclonal antibody comprising the variable and constant region sequences shown in SEQ ID NO:6;
  (vii) a monoclonal antibody comprising the variable and constant region sequences shown in SEQ ID NO:7;
  (viii) a monoclonal antibody comprising the variable and constant region sequences shown in SEQ ID NO:8;
  (ix) a monoclonal antibody comprising the variable and constant region sequences shown in SEQ ID NO:6 and the variable and constant region sequences shown SEQ ID NO:7; and
  (x) a monoclonal antibody comprising the variable and constant region sequences shown in SEQ ID NO:6 and the variable and constant region sequences shown SEQ ID NO:8.

53. The method of claim 1, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

54. The method of claim 12, wherein said antagonist anti-CD40 monoclonal antibody is a monoclonal antibody comprising an amino acid sequence selected from the group consisting of:
(i) SEQ ID NO:2;
(ii) SEQ ID NO:4;
(iii) SEQ ID NO:5;
(iv) SEQ ID NO:2 and SEQ ID NO:4; and
(vi) SEQ ID NO:2 and SEQ ID NO:5
(vi) SEQ ID NO:6;
(vii) SEQ ID NO:7;
(viii) SEQ ID NO:8;
(ix) SEQ ID NO:6 and SEQ ID NO:7; and
(x) SEQ ID NO:6 and SEQ ID NO:8.

55. The method of claim 12, wherein said antagonist anti-CD40 antibody is selected from the group consisting of:
(i) a monoclonal antibody comprising the variable and constant region sequences shown in SEQ ID NO:2;
(ii) a monoclonal antibody comprising the variable and constant region sequences shown in SEQ ID NO:4;
(iii) a monoclonal antibody comprising the variable and constant region sequences shown in SEQ ID NO:5;
(iv) a monoclonal antibody comprising the variable and constant region sequences shown in SEQ ID NO:2 and the variable and constant region sequences shown SEQ ID NO:4; and
(v) a monoclonal antibody comprising the variable and constant region sequences shown in SEQ ID NO:2 and the variable and constant region sequences shown SEQ ID NO:5;
(vi) a monoclonal antibody comprising the variable and constant region sequences shown in SEQ ID NO:6;
(vii) a monoclonal antibody comprising the variable and constant region sequences shown in SEQ ID NO:7;
(viii) a monoclonal antibody comprising the variable and constant region sequences shown in SEQ ID NO:8;
(ix) a monoclonal antibody comprising the variable and constant region sequences shown in SEQ ID NO:6 and the variable and constant region sequences shown SEQ ID NO:7; and
(x) a monoclonal antibody comprising the variable and constant region sequences shown in SEQ ID NO:6 and the variable and constant region sequences shown SEQ ID NO:8.

56. The method of claim 12, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

57. The method of claim 28, wherein said antagonist anti-CD40 monoclonal antibody is a monoclonal antibody comprising an amino acid sequence selected from the group consisting of:
(i) SEQ ID NO:2;
(ii) SEQ ID NO:4;
(iii) SEQ ID NO:5;
(iv) SEQ ID NO:2 and SEQ ID NO:4; and
(vii) SEQ ID NO:2 and SEQ ID NO:5
(vi) SEQ ID NO:6;
(vii) SEQ ID NO:7;
(viii) SEQ ID NO:8;
(ix) SEQ ID NO:6 and SEQ ID NO:7; and
(x) SEQ ID NO:6 and SEQ ID NO:8.

58. The method of claim 28, wherein said antagonist anti-CD40 antibody is selected from the group consisting of:
(i) a monoclonal antibody comprising the variable and constant region sequences shown in SEQ ID NO:2;
(ii) a monoclonal antibody comprising the variable and constant region sequences shown in SEQ ID NO:4;
(iii) a monoclonal antibody comprising the variable and constant region sequences shown in SEQ ID NO:5;
(iv) a monoclonal antibody comprising the variable and constant region sequences shown in SEQ ID NO:2 and the variable and constant region sequences shown SEQ ID NO:4;
(v) a monoclonal antibody comprising the variable and constant region sequences shown in SEQ ID NO:2 and the variable and constant region sequences shown SEQ ID NO:5;
(vi) a monoclonal antibody comprising the variable and constant region sequences shown in SEQ ID NO:6;
(vii) a monoclonal antibody comprising the variable and constant region sequences shown in SEQ ID NO:7;
(viii) a monoclonal antibody comprising the variable and constant region sequences shown in SEQ ID NO:8;
(ix) a monoclonal antibody comprising the variable and constant region sequences shown in SEQ ID NO:6 and the variable and constant region sequences shown SEQ ID NO:7; and
(x) a monoclonal antibody comprising the variable and constant region sequences shown in SEQ ID NO:6 and the variable and constant region sequences shown SEQ ID NO:8.

59. The method of claim 28, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

60. The method of claim 39, wherein said antagonist anti-CD40 monoclonal antibody is a monoclonal antibody comprising an amino acid sequence selected from the group consisting of:
(i) SEQ ID NO:2;
(ii) SEQ ID NO:4;
(iii) SEQ ID NO:5;
(iv) SEQ ID NO:2 and SEQ ID NO:4; and
(viii) SEQ ID NO:2 and SEQ ID NO:5
(vi) SEQ ID NO:6;
(vii) SEQ ID NO:7;
(viii) SEQ ID NO:8;
(ix) SEQ ID NO:6 and SEQ ID NO:7; and
(x) SEQ ID NO:6 and SEQ ID NO:8.

61. The method of claim 39, wherein said antagonist anti-CD40 antibody is selected from the group consisting of:
(i) a monoclonal antibody comprising the variable and constant region sequences shown in SEQ ID NO:2;
(ii) a monoclonal antibody comprising the variable and constant region sequences shown in SEQ ID NO:4;
(iii) a monoclonal antibody comprising the variable and constant region sequences shown in SEQ ID NO:5;

(iv) a monoclonal antibody comprising the variable and constant region sequences shown in SEQ ID NO:2 and the variable and constant region sequences shown SEQ ID NO:4;

(v) a monoclonal antibody comprising the variable and constant region sequences shown in SEQ ID NO:2 and the variable and constant region sequences shown SEQ ID NO:5;

(vi) a monoclonal antibody comprising the variable and constant region sequences shown in SEQ ID NO:6;

(vii) a monoclonal antibody comprising the variable and constant region sequences shown in SEQ ID NO:7;

(viii) a monoclonal antibody comprising the variable and constant region sequences shown in SEQ ID NO:8;

(ix) a monoclonal antibody comprising the variable and constant region sequences shown in SEQ ID NO:6 and the variable and constant region sequences shown SEQ ID NO:7; and (x) a monoclonal antibody comprising the variable and constant region sequences shown in SEQ ID NO:6 and the variable and constant region sequences shown SEQ ID NO:8.

62. The method of claim 39, wherein said antagonist anti-CD40 antibody is selected from the group consisting of the antibody CHIR-5.9 produced by the hybridoma cell line deposited with the ATCC as Patent Deposit No. PTA-5542 and the antibody CHIR-12.12 produced by the hybridoma cell line deposited with the ATCC as Patent Deposit No. PTA-5543.

* * * * *

UNITED STATES PATENT AND TRADEMARK OFFICE
CERTIFICATE OF CORRECTION

PATENT NO. : 8,337,851 B2
APPLICATION NO. : 11/914714
DATED : December 25, 2012
INVENTOR(S) : Aukerman et al.

Page 1 of 2

It is certified that error appears in the above-identified patent and that said Letters Patent is hereby corrected as shown below:

IN THE SPECIFICATION

Column 22, line 51, delete "LAP" and insert --IAP-- therefor.

Column 22, line 56, delete "Dierlamrn" and insert --Dierlamm-- therefor.

Column 23, line 24, delete "LAP" and insert --IAP-- therefor.

Column 27, line 17, delete "P2" and insert --$\beta$2-- therefor.

Column 33, line 20, delete "mM" and insert --nM-- therefor.

Column 44, line 22, delete "Hunan" and insert --Human-- therefor.

Column 49, line 32, delete "K" and insert --$\kappa$-- therefor.

IN THE CLAIMS

In Claim 28, at Column 110, line 1, before "comparing" insert --f)--.

In Claim 51, at Column 112, line 31, at the end of item (iv), delete "and".

In Claim 51, at Column 112, line 32, at the end of item (v), insert --;--.

In Claim 54, at Column 113, line 15, at the end of item (iv), delete "and".

In Claim 54, at Column 113, line 16, delete "(vi)" and insert --(v)-- therefor.

In Claim 54, at Column 113, at the end of line 16, insert --;--.

In Claim 55, at Column 113, line 33, at the end of item (iv), delete "and".

In Claim 57, at Column 113, line 66, at the end of item (iv), delete "and".

In Claim 57, at Column 113, line 67, delete "(vii)" and insert --(v)-- therefor.

In Claim 57, at Column 113, at the end of line 67, insert --;--.

Signed and Sealed this
Sixteenth Day of July, 2013

Teresa Stanek Rea
*Acting Director of the United States Patent and Trademark Office*

IN THE CLAIMS

In Claim 60, at Column 114, line 52, at the end of item (iv), delete "and".

In Claim 60, at Column 114, line 53, delete "(viii)" and insert --(v)-- therefor.

In Claim 60, at Column 114, at the end of line 53, insert --;--.

SEQUENCE LISTING

<160> NUMBER OF SEQ ID NOS: 16

<210> SEQ ID NO 1
<211> LENGTH: 720
<212> TYPE: DNA
<213> ORGANISM: Artificial Sequence
<220> FEATURE:
<223> OTHER INFORMATION: Coding sequence for light chain of 12.12 human -continued

```
        anti-CD40 antibody
<221> NAME/KEY: CDS
<222> LOCATION: (1)...(720)

<400> SEQUENCE: 1 atg gcg ctc cct gct cag ctc ctg ggg ctg cta atg ctc tgg gtc tct     48
Met Ala Leu Pro Ala Gln Leu Leu Gly Leu Leu Met Leu Trp Val Ser
 1               5                  10                  15 gga tcc agt ggg gat att gtg atg act cag tct cca ctc tcc ctg acc     96
Gly Ser Ser Gly Asp Ile Val Met Thr Gln Ser Pro Leu Ser Leu Thr
             20                  25                  30 gtc acc cct gga gag ccg gcc tcc atc tcc tgc agg tcc agt cag agc    144
Val Thr Pro Gly Glu Pro Ala Ser Ile Ser Cys Arg Ser Ser Gln Ser
         35                  40                  45 ctc ctg tat agt aat gga tac aac tat ttg gat tgg tac ctg cag aag    192
Leu Leu Tyr Ser Asn Gly Tyr Asn Tyr Leu Asp Trp Tyr Leu Gln Lys
     50                  55                  60 cca ggg cag tct cca cag gtc ctg atc tct ttg ggt tct aat cgg gcc    240
Pro Gly Gln Ser Pro Gln Val Leu Ile Ser Leu Gly Ser Asn Arg Ala
 65                  70                  75                  80 tcc ggg gtc cct gac agg ttc agt ggc agt gga tca ggc aca gat ttt    288
Ser Gly Val Pro Asp Arg Phe Ser Gly Ser Gly Ser Gly Thr Asp Phe
                 85                  90                  95 aca ctg aaa atc agc aga gtg gag gct gag gat gtt ggg gtt tat tac    336
Thr Leu Lys Ile Ser Arg Val Glu Ala Glu Asp Val Gly Val Tyr Tyr
            100                 105                 110 tgc atg caa gct cga caa act cca ttc act ttc ggc cct ggg acc aaa    384
Cys Met Gln Ala Arg Gln Thr Pro Phe Thr Phe Gly Pro Gly Thr Lys
        115                 120                 125 gtg gat atc aga cga act gtg gct gca cca tct gtc ttc atc ttc ccg    432
Val Asp Ile Arg Arg Thr Val Ala Ala Pro Ser Val Phe Ile Phe Pro
    130                 135                 140 cca tct gat gag cag ttg aaa tct gga act gcc tct gtt gtg tgc ctg    480
Pro Ser Asp Glu Gln Leu Lys Ser Gly Thr Ala Ser Val Val Cys Leu
145                 150                 155                 160 ctg aat aac ttc tat ccc aga gag gcc aaa gta cag tgg aag gtg gat    528
Leu Asn Asn Phe Tyr Pro Arg Glu Ala Lys Val Gln Trp Lys Val Asp
                165                 170                 175 aac gcc ctc caa tcg ggt aac tcc cag gag agt gtc aca gag cag gac    576
Asn Ala Leu Gln Ser Gly Asn Ser Gln Glu Ser Val Thr Glu Gln Asp
            180                 185                 190 agc aag gac agc acc tac agc ctc agc agc acc ctg acg ctg agc aaa    624
Ser Lys Asp Ser Thr Tyr Ser Leu Ser Ser Thr Leu Thr Leu Ser Lys
        195                 200                 205 gca gac tac gag aaa cac aaa gtc tac gcc tgc gaa gtc acc cat cag    672
Ala Asp Tyr Glu Lys His Lys Val Tyr Ala Cys Glu Val Thr His Gln
    210                 215                 220 ggc ctg agc tcg ccc gtc aca aag agc ttc aac agg gga gag tgt tag    720
Gly Leu Ser Ser Pro Val Thr Lys Ser Phe Asn Arg Gly Glu Cys  *
225                 230                 235

<210> SEQ ID NO 2
<211> LENGTH: 239
<212> TYPE: PRT
<213> ORGANISM: Artificial Sequence
<220> FEATURE:
<223> OTHER INFORMATION: Coding sequence for light chain of 12.12 human
      anti-CD40 antibody

<400> SEQUENCE: 2

Met Ala Leu Pro Ala Gln Leu Leu Gly Leu Leu Met Leu Trp Val Ser
 1               5                  10                  15
```

```
Gly Ser Ser Gly Asp Ile Val Met Thr Gln Ser Pro Leu Ser Leu Thr
            20                  25                  30

Val Thr Pro Gly Glu Pro Ala Ser Ile Ser Cys Arg Ser Ser Gln Ser
        35                  40                  45

Leu Leu Tyr Ser Asn Gly Tyr Asn Tyr Leu Asp Trp Tyr Leu Gln Lys
    50                  55                  60

Pro Gly Gln Ser Pro Gln Val Leu Ile Ser Leu Gly Ser Asn Arg Ala
65              70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Met Gln Ala Arg Gln Thr Pro Phe Thr Phe Gly Pro Gly Thr Lys
        115                 120                 125

Val Asp Ile Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 3
<211> LENGTH: 2016
<212> TYPE: DNA
<213> ORGANISM: Artificial Sequence
<220> FEATURE:
<223> OTHER INFORMATION: Coding sequence for heavy chain of 12.12 human
      anti-CD40 antibody (with introns)

<400> SEQUENCE: 3
atggagtttg ggctgagctg ggttttcctt gttgctattt taagaggtgt ccagtgtcag      60
gtgcagttgg tggagtctgg gggaggcgtg gtccagcctg gaggtccct gagactctcc     120 tgtgcagcct ctggattcac cttcagtagc tatggcatgc actgggtccg ccaggctcca    180
ggcaaggggc tggagtgggt ggcagttata tcatatgagg aaagtaatag ataccatgca    240
gactccgtga agggccgatt caccatctcc agagacaatt ccaagatcac gctgtatctg    300
caaatgaaca gcctcagaac tgaggacacg gctgtgtatt actgtgcgag agatgggggt    360
atagcagcac ctgggcctga ctactggggc caggaacccc tggtcaccgt ctcctcagca    420
agtaccaagg gcccatccgt cttccccctg gcgcccgcta gcaagagcac ctctggggc    480 acagcggccc tgggctgcct ggtcaaggac tacttccccg aaccggtgac ggtgtcgtgg    540
aactcaggcg ccctgaccag cggcgtgcac accttcccgg ctgtcctaca gtcctcagga    600
ctctactccc tcagcagcgt ggtgaccgtg ccctccagca gcttgggcac ccagacctac    660
atctgcaacg tgaatcacaa gcccagcaac accaaggtgg acaagagagt tggtgagagg    720
ccagcacagg gagggagggt gtctgctgga agccaggctc agcgctcctg cctggacgca    780
tcccggctat gcagtcccag tccagggcag caaggcaggc cccgtctgcc tcttcacccg    840
```

```
gaggcctctg cccgcccac tcatgctcag ggagagggtc ttctggcttt ttccccaggc    900
tctgggcagg cacaggctag gtgccctaa cccaggccct gcacacaaag gggcaggtgc    960
tgggctcaga cctgccaaga gccatatccg ggaggaccct gcccctgacc taagcccacc   1020
ccaaaggcca aactctccac tccctcagct cggacacctt ctctcctccc agattccagt   1080
aactcccaat cttctctctg cagagccaa atcttgtgac aaaactcaca catgcccacc    1140
gtgcccaggt aagccagccc aggcctcgcc ctccagctca aggcgggaca ggtgccctag   1200
agtagcctgc atccagggac aggccccagc cgggtgctga cacgtccacc tccatctctt   1260
cctcagcacc tgaactcctg gggggaccgt cagtcttcct cttcccccca aaacccaagg   1320
acaccctcat gatctcccgg acccctgagg tcacatgcgt ggtggtggac gtgagccacg   1380
aagaccctga ggtcaagttc aactggtacg tggacggcgt ggaggtgcat aatgccaaga   1440
caaagccgcg ggaggagcag tacaacagca cgtaccgtgt ggtcagcgtc ctcaccgtcc   1500
tgcaccagga ctggctgaat ggcaaggagt acaagtgcaa ggtctccaac aaagccctcc   1560
cagcccccat cgagaaaacc atctccaaag ccaaaggtgg acccgtgggg gtgcgagggc   1620
cacatggaca gaggccggct cggcccaccc tctgccctga gagtgaccgc tgtaccaacc   1680
tctgtcccta cagggcagcc ccgagaacca caggtgtaca ccctgccccc atcccgggag   1740
gagatgacca gaaccaggt cagcctgacc tgcctggtca aaggcttcta tcccagcgac   1800
atcgccgtgg agtgggagag caatgggcag ccggagaaca actacaagac cacgcctccc   1860
gtgctggact ccgacggctc cttcttcctc tatagcaagc tcaccgtgga caagagcagg   1920
tggcagcagg ggaacgtctt ctcatgctcc gtgatgcatg aggctctgca caaccactac   1980
acgcagaaga gcctctccct gtctccgggt aaatga                             2016
```

```
<210> SEQ ID NO 4
<211> LENGTH: 469
<212> TYPE: PRT
<213> ORGANISM: Artificial Sequence
<220> FEATURE:
<223> OTHER INFORMATION: Heavy chain of 12.12 human anti-CD40 antibody

<400> SEQUENCE: 4

Met Glu Phe Gly Leu Ser Trp Val Phe Leu Val Ala Ile Leu Arg Gly
 1               5                  10                  15

Val Gln Cys Gln Val Gln Leu Val Glu Ser Gly Gly Val Val Gln
                20                  25                  30

Pro Gly Arg Ser Leu Arg Leu Ser Cys Ala Ala Ser Gly Phe Thr Phe
            35                  40                  45

Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ala Ser Lys Ser Thr Ser Gly Gly
145                 150                 155                 160
```

Thr Ala Ala Leu Gly Cys Leu Val Lys Asp Tyr Phe Pro Glu Pro Val
165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
                195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
                260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
                340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 5
<211> LENGTH: 469
<212> TYPE: PRT
<213> ORGANISM: Artificial Sequence
<220> FEATURE:
<223> OTHER INFORMATION: Heavy chain of variant of 12.12 human anti-CD40
      antibody

<400> SEQUENCE: 5

Met Glu Phe Gly Leu Ser Trp Val Phe Leu Val Ala Ile Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
            35                  40                  45

```
Ser Ser Tyr Gly Met His Trp Val Arg Gln Ala Pro Gly Lys Gly Leu
    50                  55                  60

Glu Trp Val Ala Val Ile Ser Tyr Glu Glu Ser Asn Arg Tyr His Ala
65                  70                  75                  80

Asp Ser Val Lys Gly Arg Phe Thr Ile Ser Arg Asp Asn Ser Lys Ile
                85                  90                  95

Thr Leu Tyr Leu Gln Met Asn Ser Leu Arg Thr Glu Asp Thr Ala Val
            100                 105                 110

Tyr Tyr Cys Ala Arg Asp Gly Gly Ile Ala Ala Pro Gly Pro Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
```

<210> SEQ ID NO 6
<211> LENGTH: 239
<212> TYPE: PRT
<213> ORGANISM: Artificial Sequence
<220> FEATURE:
<223> OTHER INFORMATION: Light chain of 5.9 human anti-CD40 antibody

<400> SEQUENCE: 6

```
Met Ala Leu Leu Ala Gln Leu Gly Leu Leu Met Leu Trp Val Pro
1               5                   10                  15

Gly Ser Ser Gly Ala Ile Val Met Thr Gln Pro Pro Leu Ser Ser Pro
            20                  25                  30

Val Thr Leu Gly Gln Pro Ala Ser Ile Ser Cys Arg Ser Ser Gln Ser
        35                  40                  45

Leu Val His Ser Asp Gly Asn Thr Tyr Leu Asn Trp Leu Gln Gln Arg
    50                  55                  60

Pro Gly Gln Pro Pro Arg Leu Leu Ile Tyr Lys Phe Phe Arg Arg Leu
65                  70                  75                  80

Ser Gly Val Pro Asp Arg Phe Ser Gly Ser Gly Ala Gly Thr Asp Phe
                85                  90                  95

Thr Leu Lys Ile Ser Arg Val Glu Ala Glu Asp Val Gly Val Tyr Tyr
            100                 105                 110

Cys Met Gln Val Thr Gln Phe Pro His Thr Phe Gly Gln Gly Thr Arg
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235
```

<210> SEQ ID NO 7
<211> LENGTH: 474
<212> TYPE: PRT
<213> ORGANISM: Artificial Sequence
<220> FEATURE:
<223> OTHER INFORMATION: Heavy chain of 5.9 human anti-CD40 antibody

<400> SEQUENCE: 7

```
Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
```

```
            65                  70                  75                  80
        Pro Ser Phe Gln Gly Gln Val Thr Ile Ser Ala Asp Lys Ser Ile Ser
                         85                  90                  95

Thr Ala Tyr Leu Gln Trp Ser Ser Leu Lys Ala Ser Asp Thr Ala Met
                        100                 105                 110

Tyr Tyr Cys Ala Arg Gly Thr Ala Ala Gly Arg Asp Tyr Tyr Tyr Tyr
                        115                 120                 125

Tyr Gly Met Asp Val Trp Gly Gln Gly Thr Thr Val Thr Val Ser Ser
                    130                 135                 140

Ala Ser Thr Lys Gly Pro Ser Val Phe Pro Leu Ala Pro Ala Ser Lys
        145                 150                 155                 160

Ser Thr Ser Gly Gly Thr Ala Ala Leu Gly Cys Leu Val Lys Asp Tyr
                        165                 170                 175

Phe Pro Glu Pro Val Thr Val Ser Trp Asn Ser Gly Ala Leu Thr Ser
                        180                 185                 190

Gly Val His Thr Phe Pro Ala Val Leu Gln Ser Ser Gly Leu Tyr Ser
                        195                 200                 205

Leu Ser Ser Val Val Thr Val Pro Ser Ser Ser Leu Gly Thr Gln Thr
                    210                 215                 220

Tyr Ile Cys Asn Val Asn His Lys Pro Ser Asn Thr Lys Val Asp Lys
        225                 230                 235                 240

Arg Val Glu Pro Lys Ser Cys Asp Lys Thr His Thr Cys Pro Pro Cys
                        245                 250                 255

Pro Ala Pro Glu Leu Leu Gly Gly Pro Ser Val Phe Leu Phe Pro Pro
                        260                 265                 270

Lys Pro Lys Asp Thr Leu Met Ile Ser Arg Thr Pro Glu Val Thr Cys
                        275                 280                 285

Val Val Val Asp Val Ser His Glu Asp Pro Glu Val Lys Phe Asn Trp
                    290                 295                 300

Tyr Val Asp Gly Val Glu Val His Asn Ala Lys Thr Lys Pro Arg Glu
        305                 310                 315                 320

Glu Gln Tyr Asn Ser Thr Tyr Arg Val Val Ser Val Leu Thr Val Leu
                        325                 330                 335

His Gln Asp Trp Leu Asn Gly Lys Glu Tyr Lys Cys Lys Val Ser Asn
                        340                 345                 350

Lys Ala Leu Pro Ala Pro Ile Glu Lys Thr Ile Ser Lys Ala Lys Gly
                        355                 360                 365

Gln Pro Arg Glu Pro Gln Val Tyr Thr Leu Pro Pro Ser Arg Glu Glu
                    370                 375                 380

Met Thr Lys Asn Gln Val Ser Leu Thr Cys Leu Val Lys Gly Phe Tyr
        385                 390                 395                 400

Pro Ser Asp Ile Ala Val Glu Trp Glu Ser Asn Gly Gln Pro Glu Asn
                        405                 410                 415

Asn Tyr Lys Thr Thr Pro Pro Val Leu Asp Ser Asp Gly Ser Phe Phe
                        420                 425                 430

Leu Tyr Ser Lys Leu Thr Val Asp Lys Ser Arg Trp Gln Gln Gly Asn
                        435                 440                 445

Val Phe Ser Cys Ser Val Met His Glu Ala Leu His Asn His Tyr Thr
                    450                 455                 460

Gln Lys Ser Leu Ser Leu Ser Pro Gly Lys
        465                 470

<210> SEQ ID NO 8
<211> LENGTH: 474
```

<212> TYPE: PRT
<213> ORGANISM: Artificial Sequence
<220> FEATURE:
<223> OTHER INFORMATION: Heavy chain of variant of 5.9 human anti-CD40
      antibody

<400> SEQUENCE: 8

Met Gly Ser Thr Ala Ile Leu Ala Leu Leu Ala Val Leu Gln Gly
 1               5                  10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Gly Thr Ala Ala Gly Arg Asp Tyr Tyr Tyr Tyr
        115                 120                 125

Tyr Gly Met Asp Val Trp Gly Gln Gly Thr Thr Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Arg Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

```
Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 9
<211> LENGTH: 612
<212> TYPE: DNA
<213> ORGANISM: Homo sapiens
<220> FEATURE:
<221> NAME/KEY: CDS
<222> LOCATION: (1)...(612)
<221> NAME/KEY: misc_feature
<222> LOCATION: (0)...(0)
<223> OTHER INFORMATION: Coding sequence for short isoform of human CD40

<400> SEQUENCE: 9 atg gtt cgt ctg cct ctg cag tgc gtc ctc tgg ggc tgc ttg ctg acc      48
Met Val Arg Leu Pro Leu Gln Cys Val Leu Trp Gly Cys Leu Leu Thr
 1               5                  10                  15 gct gtc cat cca gaa cca ccc act gca tgc aga gaa aaa cag tac cta      96
Ala Val His Pro Glu Pro Pro Thr Ala Cys Arg Glu Lys Gln Tyr Leu
                20                  25                  30 ata aac agt cag tgc tgt tct ttg tgc cag cca gga cag aaa ctg gtg     144
Ile Asn Ser Gln Cys Cys Ser Leu Cys Gln Pro Gly Gln Lys Leu Val
            35                  40                  45 agt gac tgc aca gag ttc act gaa acg gaa tgc ctt cct tgc ggt gaa     192
Ser Asp Cys Thr Glu Phe Thr Glu Thr Glu Cys Leu Pro Cys Gly Glu
        50                  55                  60 agc gaa ttc cta gac acc tgg aac aga gag aca cac tgc cac cag cac     240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc     288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg     336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc     384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag     432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa     480
Pro Cys Pro Val Gly Phe Phe Ser Asn Val Ser Ser Ala Phe Glu Lys
145                 150                 155                 160 tgt cac cct tgg aca agg tcc cca gga tcg gct gag agc cct ggt ggt     528
Cys His Pro Trp Thr Arg Ser Pro Gly Ser Ala Glu Ser Pro Gly Gly
                165                 170                 175 gat ccc cat cat ctt cgg gat cct gtt tgc cat cct ctt ggt gct ggt     576
Asp Pro His His Leu Arg Asp Pro Val Cys His Pro Leu Gly Ala Gly
            180                 185                 190
```

```
ctt tat caa aaa ggt ggc caa gaa gcc aac caa taa         612
Leu Tyr Gln Lys Gly Gly Gln Glu Ala Asn Gln *
        195                 200
```

<210> SEQ ID NO 10
<211> LENGTH: 203
<212> TYPE: PRT
<213> ORGANISM: Homo sapiens

<400> SEQUENCE: 10

```
Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Arg Ser Pro Gly Ser Ala Glu Ser Pro Gly Gly
                165                 170                 175

Asp Pro His His Leu Arg Asp Pro Val Cys His Pro Leu Gly Ala Gly
            180                 185                 190

Leu Tyr Gln Lys Gly Gly Gln Glu Ala Asn Gln
        195                 200
```

<210> SEQ ID NO 11
<211> LENGTH: 834
<212> TYPE: DNA
<213> ORGANISM: Homo sapiens
<220> FEATURE:
<221> NAME/KEY: CDS
<222> LOCATION: (1)...(834)
<221> NAME/KEY: misc_feature
<222> LOCATION: (0)...(0)
<223> OTHER INFORMATION: Coding sequence for long isoform of human CD40

<400> SEQUENCE: 11

```
atg gtt cgt ctg cct ctg cag tgc gtc ctc tgg ggc tgc ttg ctg acc    48
Met Val Arg Leu Pro Leu Gln Cys Val Leu Trp Gly Cys Leu Leu Thr
 1               5                  10                  15 gct gtc cat cca gaa cca ccc act gca tgc aga gaa aaa cag tac cta    96
Ala Val His Pro Glu Pro Pro Thr Ala Cys Arg Glu Lys Gln Tyr Leu
                20                  25                  30 ata aac agt cag tgc tgt tct ttg tgc cag cca gga cag aaa ctg gtg    144
Ile Asn Ser Gln Cys Cys Ser Leu Cys Gln Pro Gly Gln Lys Leu Val
            35                  40                  45 agt gac tgc aca gag ttc act gaa acg gaa tgc ctt cct tgc ggt gaa    192
Ser Asp Cys Thr Glu Phe Thr Glu Thr Glu Cys Leu Pro Cys Gly Glu
        50                  55                  60
```

```
agc gaa ttc cta gac acc tgg aac aga gag aca cac tgc cac cag cac      240
Ser Glu Phe Leu Asp Thr Trp Asn Arg Glu Thr His Cys His Gln His
 65                  70                  75                  80 aaa tac tgc gac ccc aac cta ggg ctt cgg gtc cag cag aag ggc acc      288
Lys Tyr Cys Asp Pro Asn Leu Gly Leu Arg Val Gln Gln Lys Gly Thr
                 85                  90                  95 tca gaa aca gac acc atc tgc acc tgt gaa gaa ggc tgg cac tgt acg      336
Ser Glu Thr Asp Thr Ile Cys Thr Cys Glu Glu Gly Trp His Cys Thr
            100                 105                 110 agt gag gcc tgt gag agc tgt gtc ctg cac cgc tca tgc tcg ccc ggc      384
Ser Glu Ala Cys Glu Ser Cys Val Leu His Arg Ser Cys Ser Pro Gly
        115                 120                 125 ttt ggg gtc aag cag att gct aca ggg gtt tct gat acc atc tgc gag      432
Phe Gly Val Lys Gln Ile Ala Thr Gly Val Ser Asp Thr Ile Cys Glu
    130                 135                 140 ccc tgc cca gtc ggc ttc ttc tcc aat gtg tca tct gct ttc gaa aaa      480
Pro Cys Pro Val Gly Phe Phe Ser Asn Val Ser Ser Ala Phe Glu Lys
145                 150                 155                 160 tgt cac cct tgg aca agc tgt gag acc aaa gac ctg gtt gtg caa cag      528
Cys His Pro Trp Thr Ser Cys Glu Thr Lys Asp Leu Val Val Gln Gln
                165                 170                 175 gca ggc aca aac aag act gat gtt gtc tgt ggt ccc cag gat cgg ctg      576
Ala Gly Thr Asn Lys Thr Asp Val Val Cys Gly Pro Gln Asp Arg Leu
            180                 185                 190 aga gcc ctg gtg gtg atc ccc atc atc ttc ggg atc ctg ttt gcc atc      624
Arg Ala Leu Val Val Ile Pro Ile Ile Phe Gly Ile Leu Phe Ala Ile
        195                 200                 205 ctc ttg gtg ctg gtc ttt atc aaa aag gtg gcc aag aag cca acc aat      672
Leu Leu Val Leu Val Phe Ile Lys Lys Val Ala Lys Lys Pro Thr Asn
    210                 215                 220 aag gcc ccc cac ccc aag cag gaa ccc cag gag atc aat ttt ccc gac      720
Lys Ala Pro His Pro Lys Gln Glu Pro Gln Glu Ile Asn Phe Pro Asp
225                 230                 235                 240 gat ctt cct ggc tcc aac act gct gct cca gtg cag gag act tta cat      768
Asp Leu Pro Gly Ser Asn Thr Ala Ala Pro Val Gln Glu Thr Leu His
                245                 250                 255 gga tgc caa ccg gtc acc cag gag gat ggc aaa gag agt cgc atc tca      816
Gly Cys Gln Pro Val Thr Gln Glu Asp Gly Lys Glu Ser Arg Ile Ser
            260                 265                 270 gtg cag gag aga cag tga                                              834
Val Gln Glu Arg Gln *
        275

<210> SEQ ID NO 12
<211> LENGTH: 277
<212> TYPE: PRT
<213> ORGANISM: Homo sapiens

<400> SEQUENCE: 12

Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
 65                 70                  75                  80
```

```
Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 13
<211> LENGTH: 786
<212> TYPE: DNA
<213> ORGANISM: Homo sapiens
<220> FEATURE:
<221> NAME/KEY: CDS
<222> LOCATION: (1)...(786)
<221> NAME/KEY: misc_feature
<222> LOCATION: (0)...(0)
<223> OTHER INFORMATION: CD40L

<400> SEQUENCE: 13 atg atc gaa aca tac aac caa act tct ccc cga tct gcg gcc act gga      48
Met Ile Glu Thr Tyr Asn Gln Thr Ser Pro Arg Ser Ala Ala Thr Gly
1               5                   10                  15 ctg ccc atc agc atg aaa att ttt atg tat tta ctt act gtt ttt ctt     96
Leu Pro Ile Ser Met Lys Ile Phe Met Tyr Leu Leu Thr Val Phe Leu
            20                  25                  30 atc acc cag atg att ggg tca gca ctt ttt gct gtg tat ctt cat aga    144
Ile Thr Gln Met Ile Gly Ser Ala Leu Phe Ala Val Tyr Leu His Arg
        35                  40                  45 agg ttg gac aag ata gaa gat gaa agg aat ctt cat gaa gat ttt gta    192
Arg Leu Asp Lys Ile Glu Asp Glu Arg Asn Leu His Glu Asp Phe Val
    50                  55                  60 ttc atg aaa acg ata cag aga tgc aac aca gga gaa aga tcc tta tcc    240
Phe Met Lys Thr Ile Gln Arg Cys Asn Thr Gly Glu Arg Ser Leu Ser
65                  70                  75                  80 tta ctg aac tgt gag gag att aaa agc cag ttt gaa ggc ttt gtg aag    288
Leu Leu Asn Cys Glu Glu Ile Lys Ser Gln Phe Glu Gly Phe Val Lys
                85                  90                  95 gat ata atg tta aac aaa gag gag acg aag aaa gaa aac agc ttt gaa    336
Asp Ile Met Leu Asn Lys Glu Glu Thr Lys Lys Glu Asn Ser Phe Glu
            100                 105                 110
```

-continued

```
atg caa aaa ggt gat cag aat cct caa att gcg gca cat gtc ata agt    384
Met Gln Lys Gly Asp Gln Asn Pro Gln Ile Ala Ala His Val Ile Ser
        115                 120                 125 gag gcc agc agt aaa aca aca tct gtg tta cag tgg gct gaa aaa gga    432
Glu Ala Ser Ser Lys Thr Thr Ser Val Leu Gln Trp Ala Glu Lys Gly
    130                 135                 140 tac tac acc atg agc aac aac ttg gta acc ctg gaa aat ggg aaa cag    480
Tyr Tyr Thr Met Ser Asn Asn Leu Val Thr Leu Glu Asn Gly Lys Gln
145                 150                 155                 160 ctg acc gtt aaa aga caa gga ctc tat tat atc tat gcc caa gtc acc    528
Leu Thr Val Lys Arg Gln Gly Leu Tyr Tyr Ile Tyr Ala Gln Val Thr
                165                 170                 175 ttc tgt tcc aat cgg gaa gct tcg agt caa gct cca ttt ata gcc agc    576
Phe Cys Ser Asn Arg Glu Ala Ser Ser Gln Ala Pro Phe Ile Ala Ser
            180                 185                 190 ctc tgc cta aag tcc ccc ggt aga ttc gag aga atc tta ctc aga gct    624
Leu Cys Leu Lys Ser Pro Gly Arg Phe Glu Arg Ile Leu Leu Arg Ala
        195                 200                 205 gca aat acc cac agt tcc gcc aaa cct tgc ggg caa caa tcc att cac    672
Ala Asn Thr His Ser Ser Ala Lys Pro Cys Gly Gln Gln Ser Ile His
    210                 215                 220 ttg gga gga gta ttt gaa ttg caa cca ggt gct tcg gtg ttt gtc aat    720
Leu Gly Gly Val Phe Glu Leu Gln Pro Gly Ala Ser Val Phe Val Asn
225                 230                 235                 240 gtg act gat cca agc caa gtg agc cat ggc act ggc ttc acg tcc ttt    768
Val Thr Asp Pro Ser Gln Val Ser His Gly Thr Gly Phe Thr Ser Phe
                245                 250                 255 ggc tta ctc aaa ctc tga                                            786
Gly Leu Leu Lys Leu *
            260
```

<210> SEQ ID NO 14
<211> LENGTH: 261
<212> TYPE: PRT
<213> ORGANISM: Homo sapiens

<400> SEQUENCE: 14

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
```

```
                            165                 170                 175
Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
                260

<210> SEQ ID NO 15
<211> LENGTH: 648
<212> TYPE: DNA
<213> ORGANISM: Homo sapiens
<220> FEATURE:
<221> NAME/KEY: CDS
<222> LOCATION: (1)...(648)
<221> NAME/KEY: misc_feature
<222> LOCATION: (0)...(0)
<223> OTHER INFORMATION: Soluble CD40L

<400> SEQUENCE: 15 cat aga agg ttg gac aag ata gaa gat gaa agg aat ctt cat gaa gat         48
His Arg Arg Leu Asp Lys Ile Glu Asp Glu Arg Asn Leu His Glu Asp
  1               5                  10                  15 ttt gta ttc atg aaa acg ata cag aga tgc aac aca gga gaa aga tcc         96
Phe Val Phe Met Lys Thr Ile Gln Arg Cys Asn Thr Gly Glu Arg Ser
             20                  25                  30 tta tcc tta ctg aac tgt gag gag att aaa agc cag ttt gaa ggc ttt        144
Leu Ser Leu Leu Asn Cys Glu Glu Ile Lys Ser Gln Phe Glu Gly Phe
         35                  40                  45 gtg aag gat ata atg tta aac aaa gag gag acg aag aaa gaa aac agc        192
Val Lys Asp Ile Met Leu Asn Lys Glu Glu Thr Lys Lys Glu Asn Ser
     50                  55                  60 ttt gaa atg caa aaa ggt gat cag aat cct caa att gcg gca cat gtc        240
Phe Glu Met Gln Lys Gly Asp Gln Asn Pro Gln Ile Ala Ala His Val
 65                  70                  75                  80 ata agt gag gcc agc agt aaa aca aca tct gtg tta cag tgg gct gaa        288
Ile Ser Glu Ala Ser Ser Lys Thr Thr Ser Val Leu Gln Trp Ala Glu
                 85                  90                  95 aaa gga tac tac acc atg agc aac aac ttg gta acc ctg gaa aat ggg        336
Lys Gly Tyr Tyr Thr Met Ser Asn Asn Leu Val Thr Leu Glu Asn Gly
            100                 105                 110 aaa cag ctg acc gtt aaa aga caa gga ctc tat tat atc tat gcc caa        384
Lys Gln Leu Thr Val Lys Arg Gln Gly Leu Tyr Tyr Ile Tyr Ala Gln
        115                 120                 125 gtc acc ttc tgt tcc aat cgg gaa gct tcg agt caa gct cca ttt ata        432
Val Thr Phe Cys Ser Asn Arg Glu Ala Ser Ser Gln Ala Pro Phe Ile
    130                 135                 140 gcc agc ctc tgc cta aag tcc ccc ggt aga ttc gag aga atc tta ctc        480
Ala Ser Leu Cys Leu Lys Ser Pro Gly Arg Phe Glu Arg Ile Leu Leu
145                 150                 155                 160 aga gct gca aat acc cac agt tcc gcc aaa cct tgc ggg caa caa tcc        528
Arg Ala Ala Asn Thr His Ser Ser Ala Lys Pro Cys Gly Gln Gln Ser
                165                 170                 175 att cac ttg gga gga gta ttt gaa ttg caa cca ggt gct tcg gtg ttt        576
Ile His Leu Gly Gly Val Phe Glu Leu Gln Pro Gly Ala Ser Val Phe
```

```
                    180                 185                 190
gtc aat gtg act gat cca agc caa gtg agc cat ggc act ggc ttc acg         624
Val Asn Val Thr Asp Pro Ser Gln Val Ser His Gly Thr Gly Phe Thr
        195                 200                 205 tcc ttt ggc tta ctc aaa ctc tga                                         648
Ser Phe Gly Leu Leu Lys Leu *
        210                 215

<210> SEQ ID NO 16
<211> LENGTH: 215
<212> TYPE: PRT
<213> ORGANISM: Homo sapiens

<400> SEQUENCE: 16

His Arg Arg Leu Asp Lys Ile Glu Asp Glu Arg Asn Leu His Glu Asp
 1               5                  10                  15

Phe Val Phe Met Lys Thr Ile Gln Arg Cys Asn Thr Gly Glu Arg Ser
                20                  25                  30

Leu Ser Leu Leu Asn Cys Glu Glu Ile Lys Ser Gln Phe Glu Gly Phe
            35                  40                  45

Val Lys Asp Ile Met Leu Asn Lys Glu Glu Thr Lys Lys Glu Asn Ser
50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
            115                 120                 125

Val Thr Phe Cys Ser Asn Arg Glu Ala Ser Ser Gln Ala Pro Phe Ile
130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
            195                 200                 205

Ser Phe Gly Leu Leu Lys Leu
            210                 215
```